US012558426B2

(12) United States Patent
Liu et al.

(10) Patent No.: US 12,558,426 B2
(45) Date of Patent: Feb. 24, 2026

(54) METHOD OF DELIVERING PROTEINS INTO CELLS

(71) Applicant: GUANGZHOU LIDE BIOMEDICINE TECHNOLOGY CO., LTD., Guangdong (CN)

(72) Inventors: Zhijia Liu, Guangdong (CN); Zhicheng Le, Guangdong (CN); Yongming Chen, Guangdong (CN)

(73) Assignee: GUANGZHOU LIDE BIOMEDICINE TECHNOLOGY CO., LTD., Guangzhou (CN)

( * ) Notice: Subject to any disclaimer, the term of this patent is extended or adjusted under 35 U.S.C. 154(b) by 385 days.

(21) Appl. No.: 18/232,339

(22) Filed: Aug. 9, 2023

(65) Prior Publication Data

US 2024/0261415 A1 Aug. 8, 2024

Related U.S. Application Data

(63) Continuation of application No. PCT/CN2021/136179, filed on Dec. 7, 2021.

(30) Foreign Application Priority Data

Feb. 9, 2021 (CN) ........................ 202110183487.1

(51) Int. Cl.
*A61K 47/54* (2017.01)
*A61K 9/14* (2006.01)

(52) U.S. Cl.
CPC ............ *A61K 47/543* (2017.08); *A61K 9/146* (2013.01)

(58) Field of Classification Search
CPC .............................. A61K 47/543; A61K 9/146
See application file for complete search history.

(56) References Cited

FOREIGN PATENT DOCUMENTS

CN 111087332 A * 5/2020 ........... C07C 323/25

OTHER PUBLICATIONS

English Translation of CN-111087332-A from EPO (Year: 2025).*

* cited by examiner

*Primary Examiner* — Michael P Cohen

(57) ABSTRACT

The present application discloses a method of delivering a protein drug into a cell, including utilization of a cationic lipid analog material. The cationic lipid analog material of the present application has an efficient intracellular delivery of a protein, and is effective for proteins of different molecular weights and charges. Moreover, the biological activity of the protein can still be maintained when the protein is delivered into the cell. At the same time, the ionizable cationic lipid analog material has low toxicity to cells and good biocompatibility, and can be used as delivery carriers for protein drugs.

18 Claims, 13 Drawing Sheets

METHOD OF DELIVERING PROTEINS INTO CELLS

CROSS-REFERENCE TO RELATED APPLICATIONS

The present application is a continuation application of PCT application No. PCT/CN2021/136179 filed on Dec. 7, 2021, which claims the benefit of Chinese Patent Application No. 202110183487.1 filed on Feb. 9, 2021. The contents of all of the aforementioned applications are incorporated by reference herein in their entirety.

TECHNICAL FIELD

The present application relates to the technical field of biomedicine, and in particular to a method of delivering a protein drug into a cell using an ionizable cationic lipid analog material.

BACKGROUND

Due to the advantages of high specificity, low toxic side effects, and relatively short cycles for drug development, protein drugs have maintained a rapid growth momentum in the market. Although there are more and more efficient targets in the cells, most of the current protein drugs available on the market are developed based on extracellular targets. This is due to the natural hydrophilicity and high molecular weight of protein drugs, which make them difficult to cross cell membranes. Therefore, vector materials need to be developed to help protein drugs penetrate cell membranes, escape or avoid endosomes, and ultimately achieve the release of protein drugs in the cytoplasm.

At present, the methods or delivery carriers for intracellular delivery of proteins mainly include electroporation, microfluidics, inorganic nanocarriers, polymer carriers, lipid nanocarriers, etc. Lipid nanomaterials have many advantages as drug delivery carriers, such as controllable structural design and synthesis, good biocompatibility, and high loading efficiency. Therefore, lipid nanocarriers are also the most common drug carriers approved by FDA, and they have great application prospects in the field of intracellular protein delivery. At present, there are many types of cationic lipid nanomaterials. However, their limitation is that they are only suitable for proteins that are negatively charged under physiological pH conditions or contain concentrated super-negatively-charged regions on the surface, their universality is not strong, their binding to proteins is weak, and their delivery efficiency is not high. Therefore, it is necessary to further develop a cationic lipid analog carrier material with high delivery efficiency of protein drugs and good universality to meet the application needs in biology, medicine or pharmacy.

SUMMARY

An objective of the present application is to overcome the shortcomings of the prior art and provide a method of delivering a protein drug into a cell using an ionizable cationic lipid analog material.

To achieve the above objective, the present application adopts the following technical solutions:

A method of delivering a protein drug into a cell, comprising utilization of a cationic lipid analog material, wherein the cationic lipid analog material is an ionizable cationic lipid analog material with a structure shown in formula (I):

I

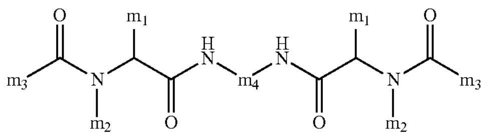

in formula (I), $m_1$ is independently selected from the group consisting of a branched alkyl, phenyl, or a heteroatom-containing aryl;

$m_2$ is

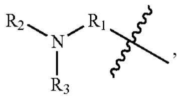

, $R_1$ is an alkyl, $R_2$ is an alkyl, $R_3$ is an alkyl or phenyl, or $R_2$ and $R_3$ are connected as a cyclic group or a heterocyclic group;

$m_3$ is independently selected from the group consisting of a linear alkyl, a linear alkenyl, or

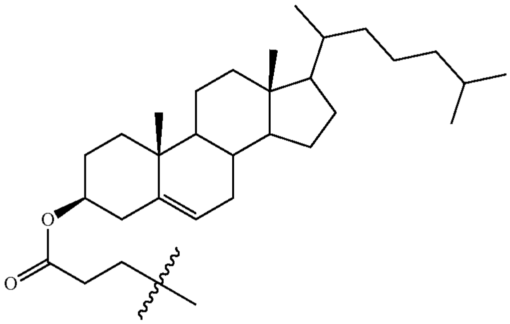

;

In the present application, the wavy line in the structural formula represents different configurations, which may be trans, cis, or a mixture of trans and cis.

$m_4$ is independently selected from the group consisting of a linear alkyl, an ether bond-containing linear alkyl, or an N-heterocycle-containing alkyl.

In the cationic lipid analog material of the present application, $m_2$ includes a tertiary amino group, ensuring the unique pH-dependent charge-tunable characteristics of the material, that is, the material shows positive charge under the acidic condition and electrically neutral or weak positive charge under the physiological condition; and $m_3$ includes a linear alkyl, a linear alkenyl, or

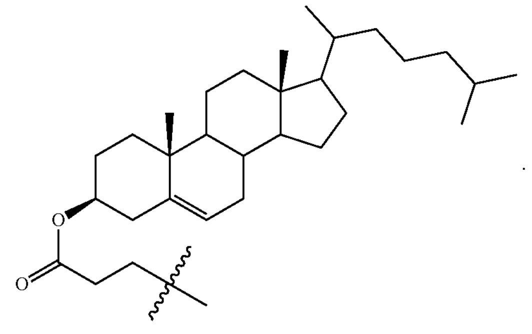 [SMILES: *CCC(=O)O[C@H]1CC[C@@]2(C)C(=CCC3C4CCC(C(C)CCCC(C)C)[C@@]4(C)CCC32)C1]

By controlling its chain length, the hydrophobicity of the material can be adjusted, and in turn, the intracellular delivery efficiency for protein drugs can be adjusted.

The cationic lipid analog material of the present application is able to form a stable complex by interacting with a variety of protein drugs. The complex efficiently crosses the cell membrane through pathways such as cell fusion and/or endocytosis, and avoids and/or escapes the endosomal barrier, ultimately enabling the release of protein drugs in the cytoplasm. Moreover, the protein drugs delivered to the cell retain their activity. At the same time, the cationic lipid analog material is not toxic to cells during delivery, and has high biological safety.

It should be noted that the term "delivery" or "intracellular delivery" as used herein refers to the entry of proteins from the outside of the cell into the inside of the cell, such that proteins are confined to the cytosol or in the organelles of the cell.

As used herein, the term "complexing" of the cationic lipid analog material with a protein or "complex" formed by the cationic lipid analog material and a protein refers to the interaction between the cationic lipid analog material and the protein, which is stable enough to bind the protein to the cationic lipid analog material to deliver the protein into the cell.

In addition, $m_1$ is selected from the group consisting of an alkyl, phenyl, or a heteroatom-containing aryl substituted by a substituent α, and the substituent includes methyl; and preferably, $m_1$ is selected from the group consisting of

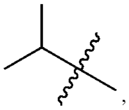,
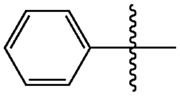, or
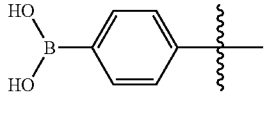.

In addition, $m_2$ is selected from the group consisting of

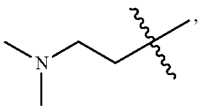,
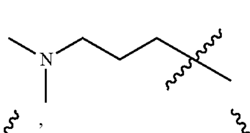,
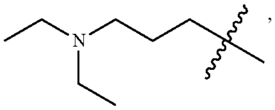,
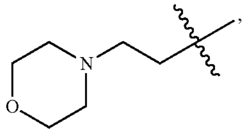,

-continued

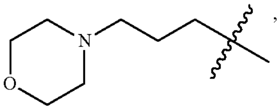,
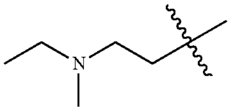,
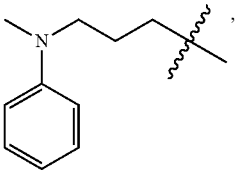,
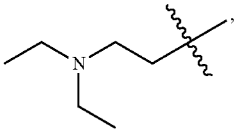,
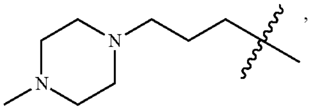,
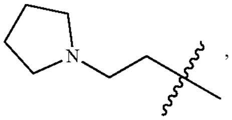, or
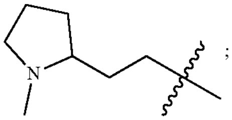;

and preferably, $m_2$ is selected from the group consisting of

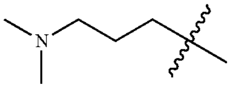,
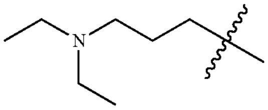, or
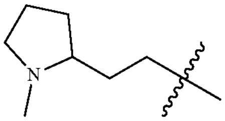, the obtained cationic lipid analog material has high intracellular delivery efficiency for proteins.

In addition, $m_3$ is selected from the group consisting of a linear alkyl with 7 to 19 carbon atoms, a linear alkenyl with 17 carbon atoms, or

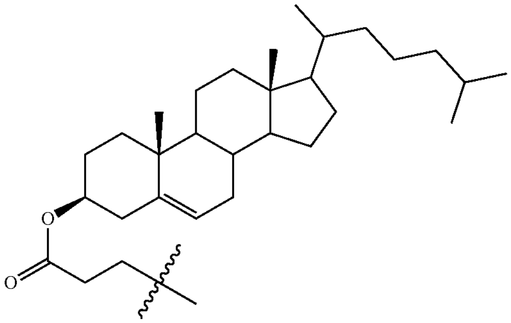.

In addition, $m_3$ is selected from the group consisting of

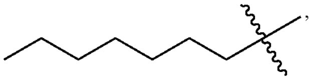,
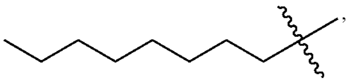,

-continued

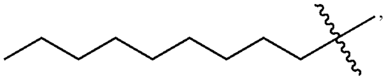
,
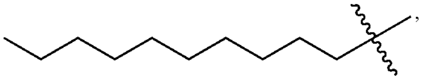
,
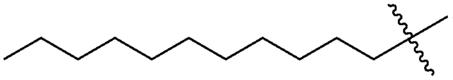
,
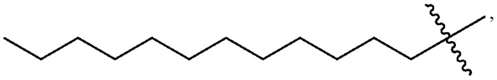
,
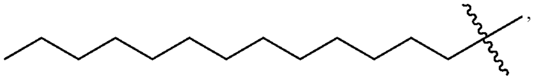
,
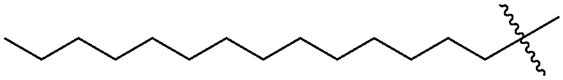
,
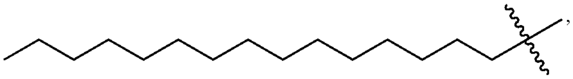
,
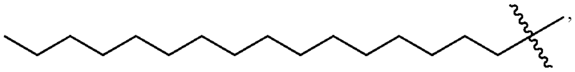
,
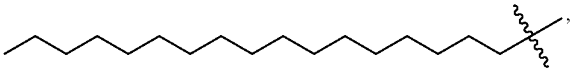
,
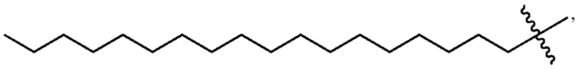
,
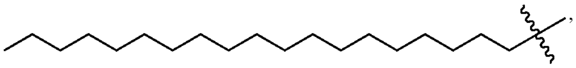
,
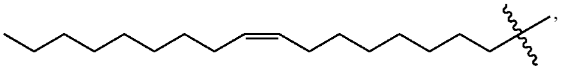
,
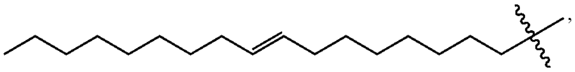
,
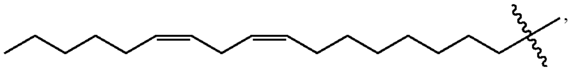
,
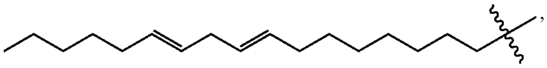
, or
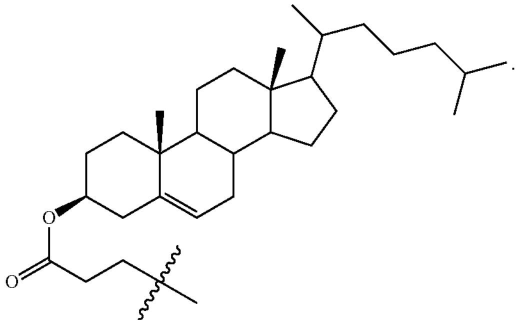 [SMILES: *CCC(=O)O[C@H]1CC[C@@]2(C)C(=CCC3C4CCC(C(C)CCCC(C)C)[C@@]4(C)CCC32)C1]
.

The present application may adjust the hydrophobicity of the cationic lipid analog material by increasing the alkyl chain length of $m_3$. Furthermore, the intracellular delivery efficiency for proteins of the cationic lipid analog material also increases with increasing alkyl chain length. To further improve the protein delivery efficiency of the material, $m_3$ is more preferably selected from the group consisting of

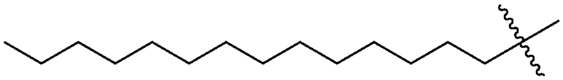
,
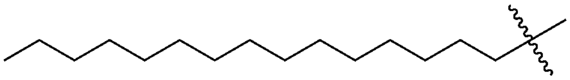
,
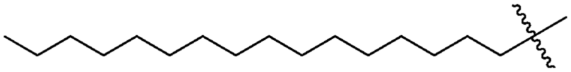
,
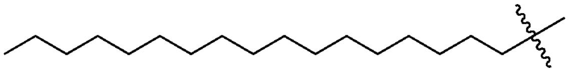
,
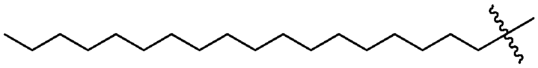
, or
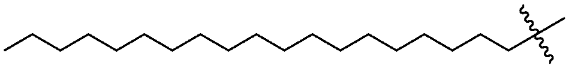
.

In addition, $m_4$ is selected from the group consisting of a linear alkyl with 6 carbon atoms, an ether bond-containing linear alkyl with 4 to 8 carbon atoms, or an N-heterocycle-containing alkyl.

In addition, $m_4$ is selected from the group consisting of

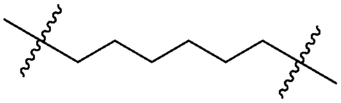
,
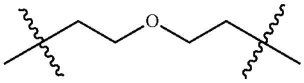
,
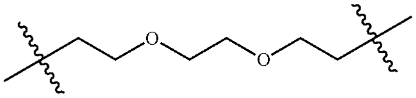
,
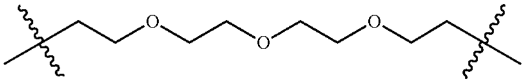
, or
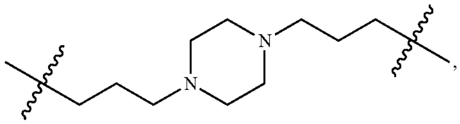
, and more preferably, $m_4$ is

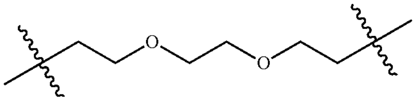
, the obtained cationic lipid analog material has high intracellular delivery efficiency for proteins.

In addition, the cationic lipid analog material has a structure selected from the group consisting of the following 72 structures:

I1R1C12A1
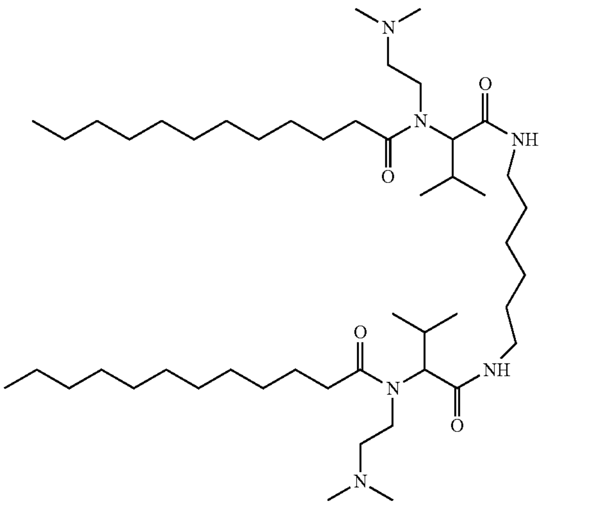
I1R1C14A1
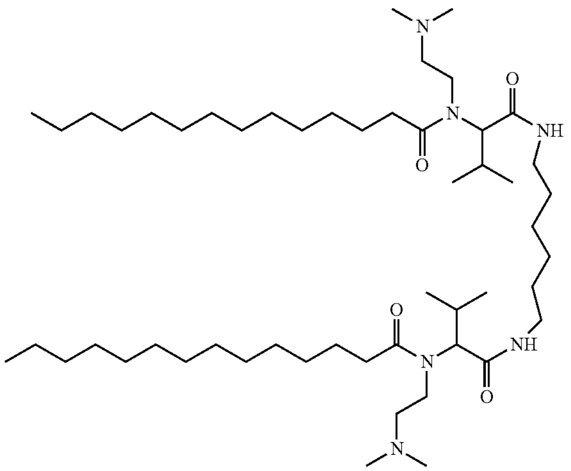
I1R1C16A1
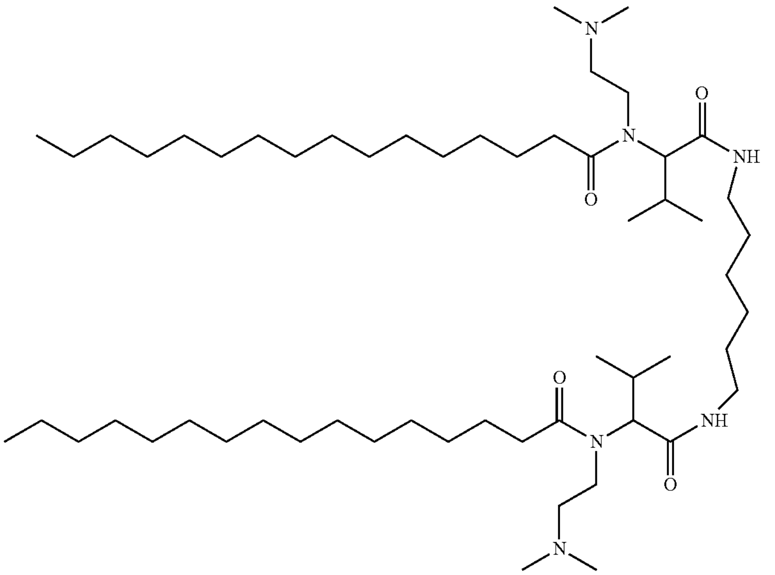
I1R1C18A1
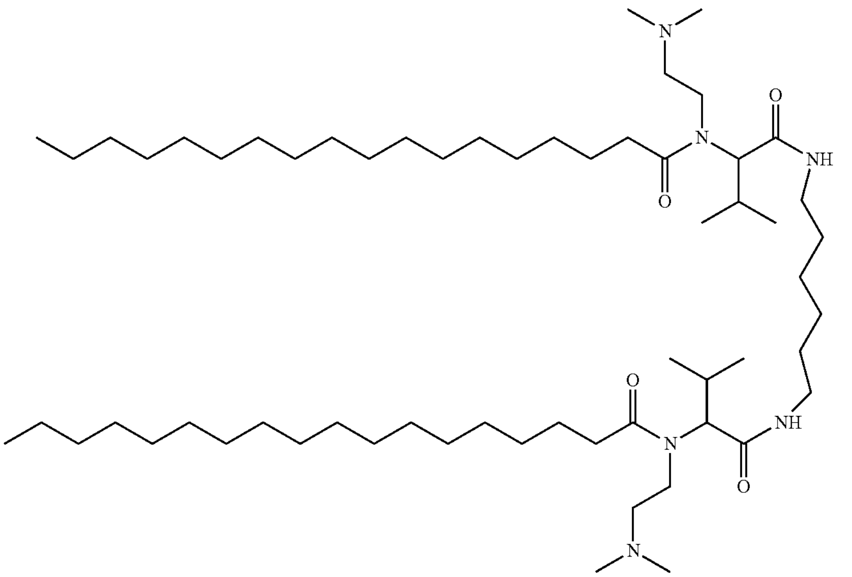

-continued
I1R1C20A1
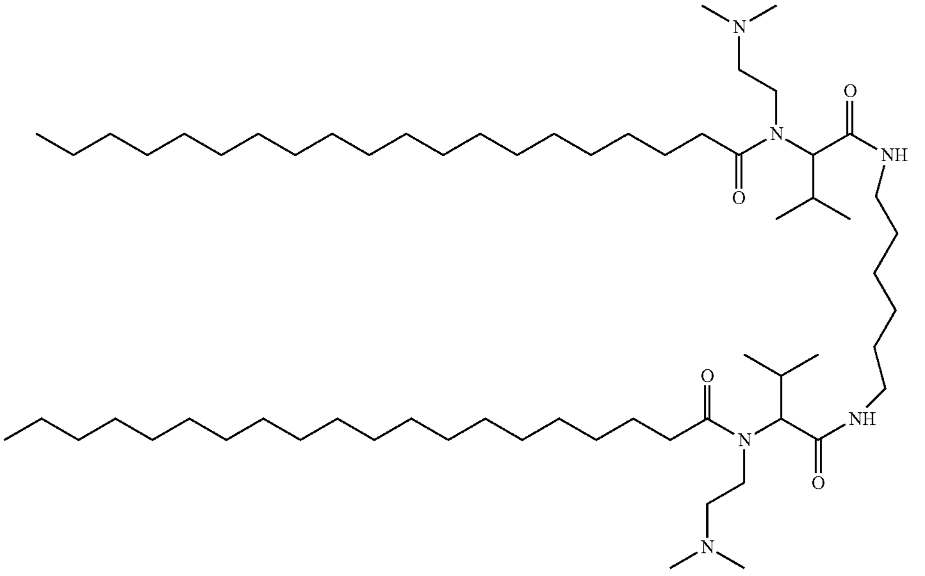
I1R1C18-1A1
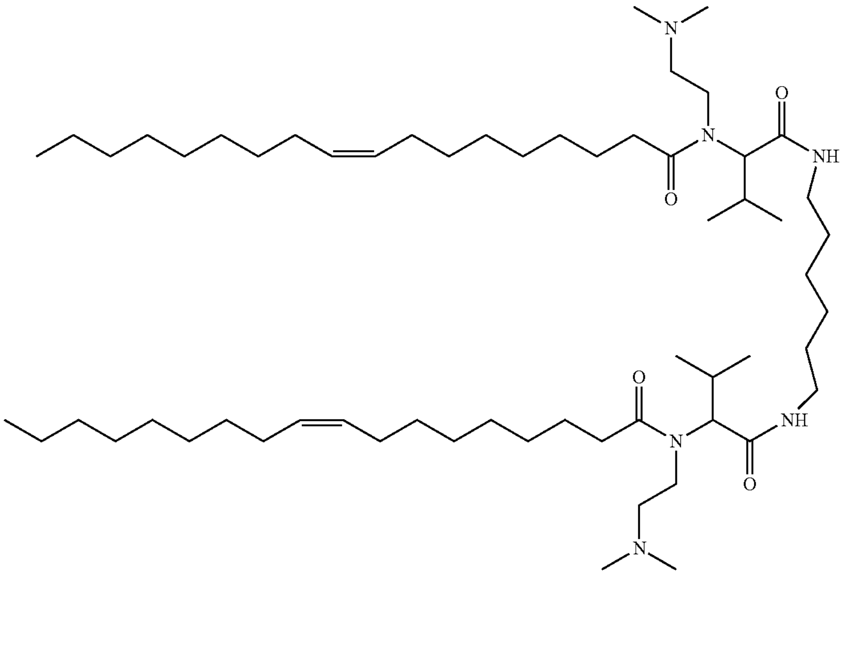

-continued
I1R3C14A1
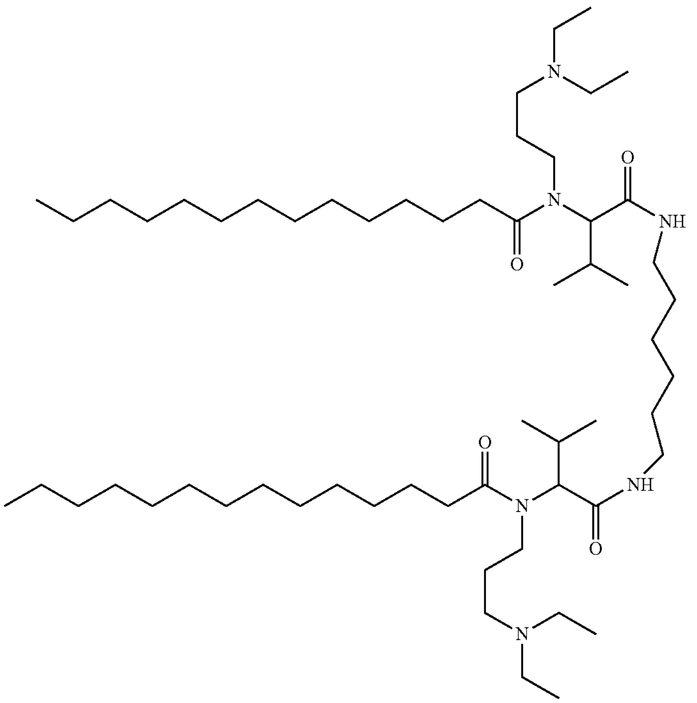
I1R1C18-2A1
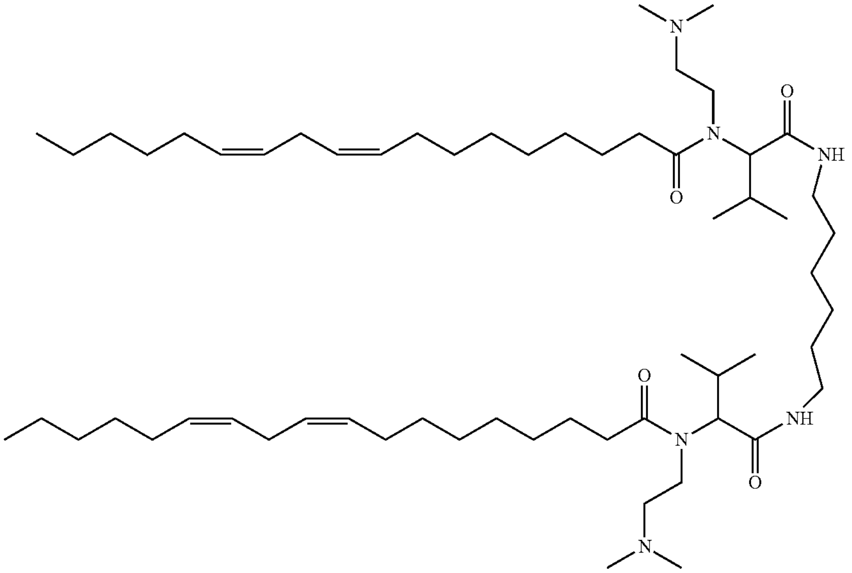

-continued
I1R2C12A1
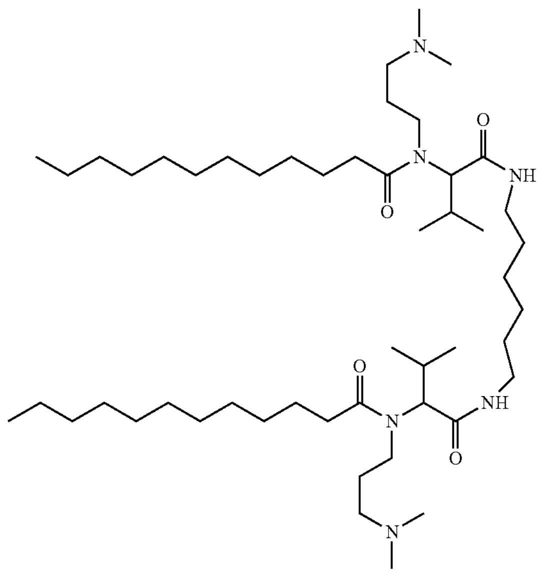
I1R2C14A1
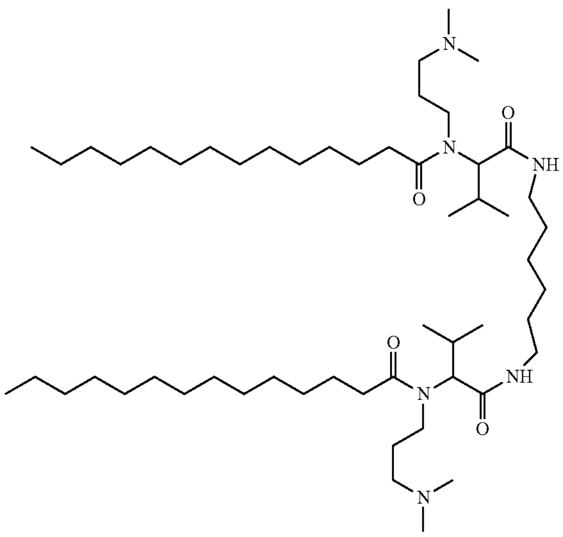
I1R2C16A1
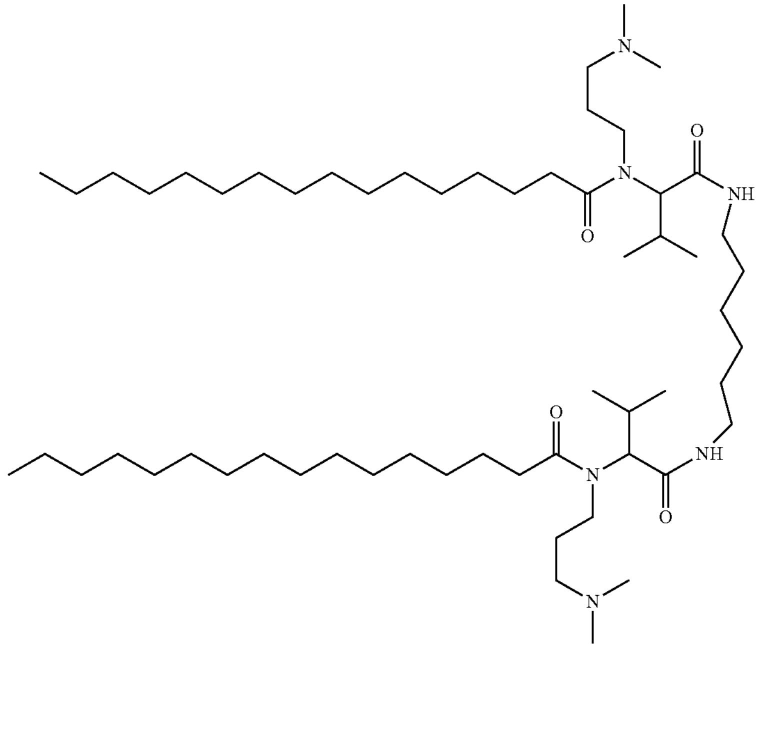

-continued
I1R2C18A1
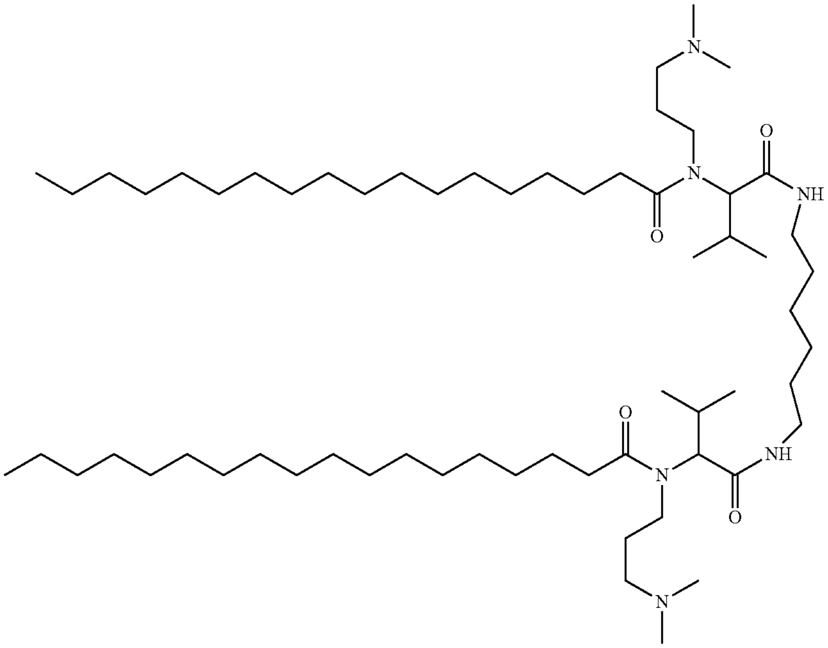
I1R2C20A1
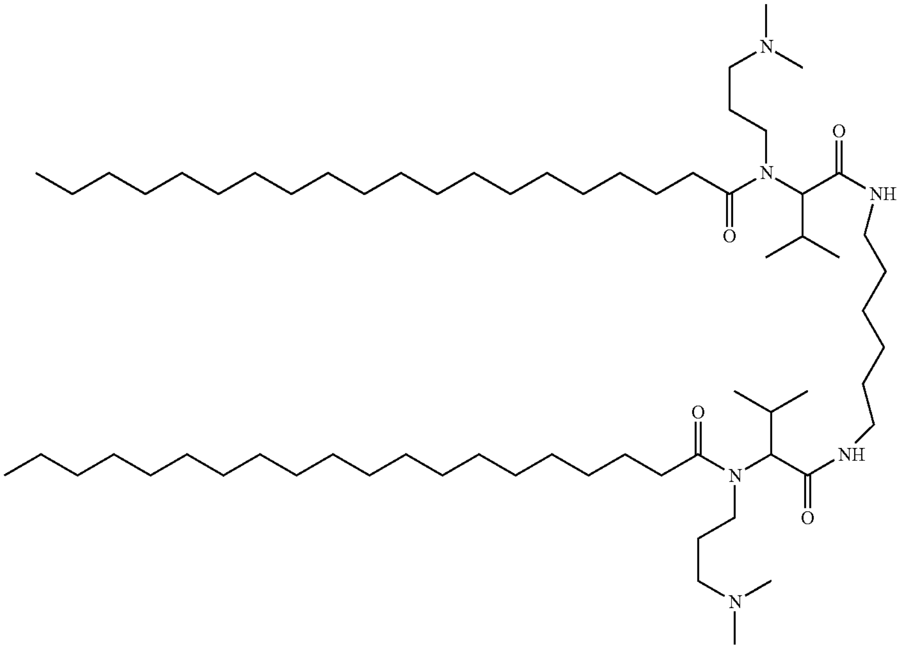

-continued
I1R2C18-1A1
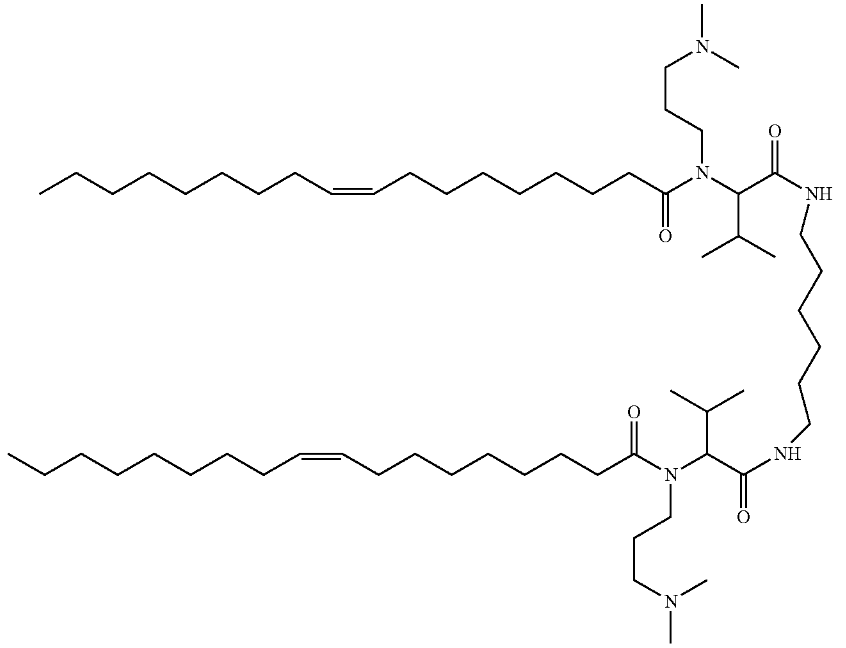
I1R2C18-2A1
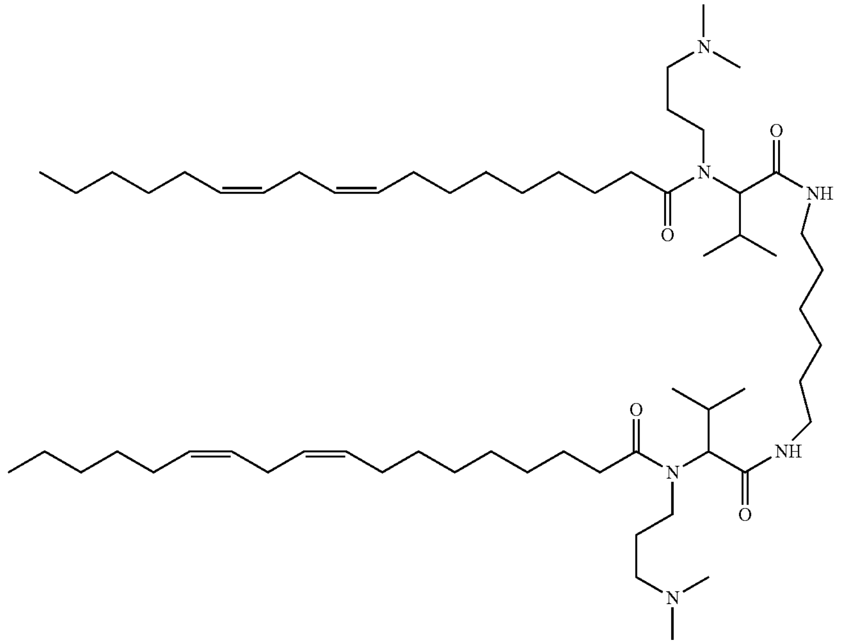

-continued
I1R3C12A1
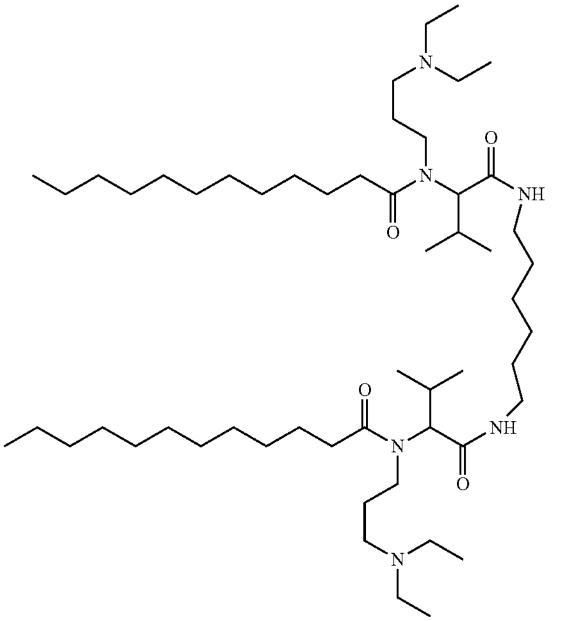
I1R3C16A1
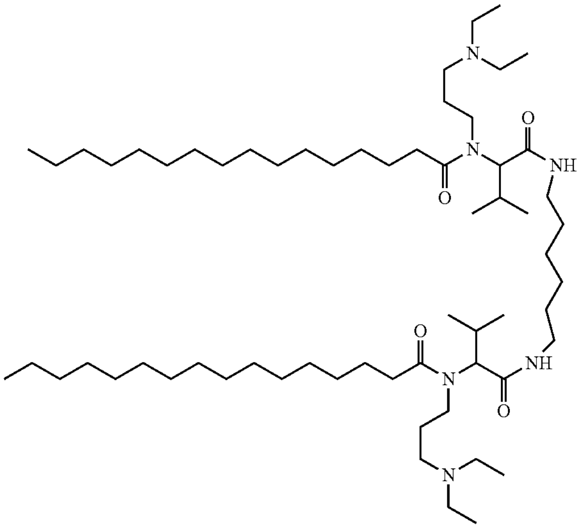
I1R3C18A1
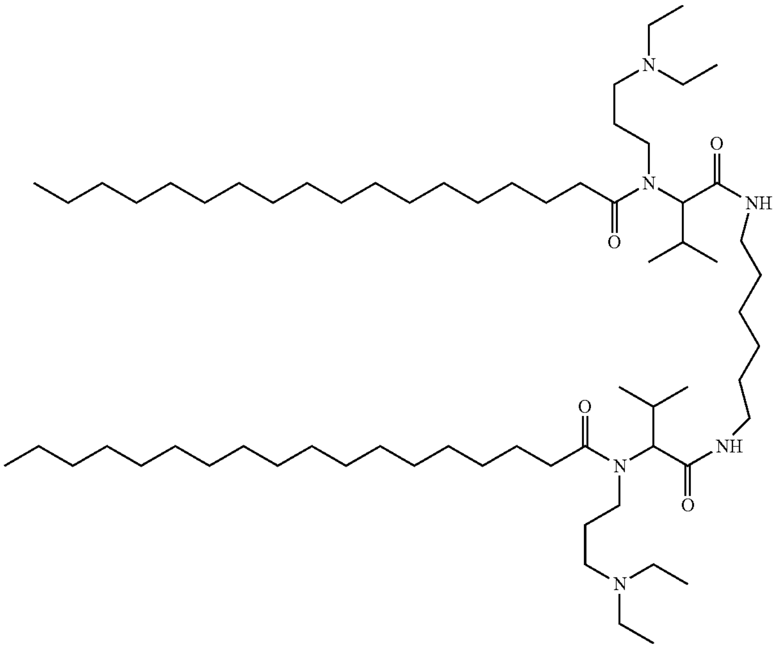

-continued
I1R3C20A1
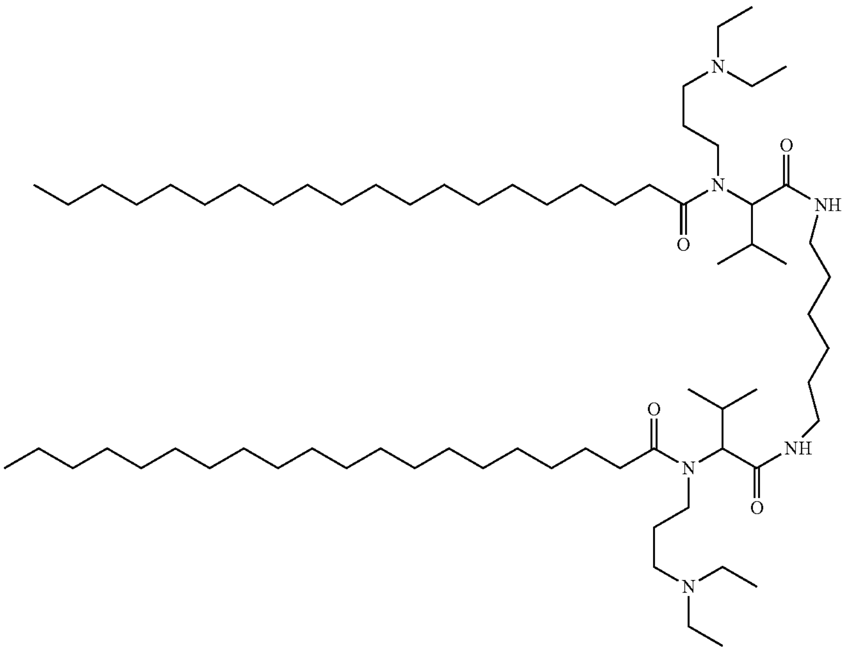
I1R3C18-1A1
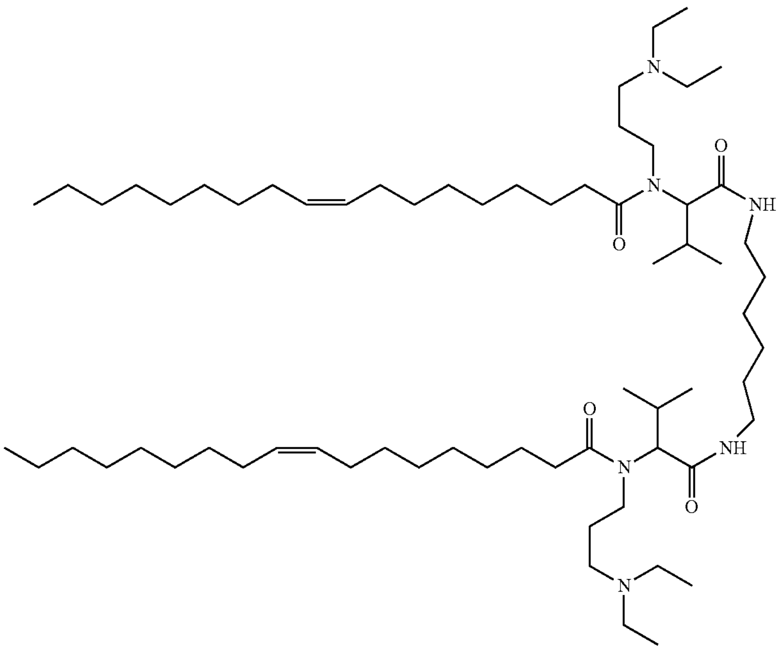

-continued
I1R3C18-2A1
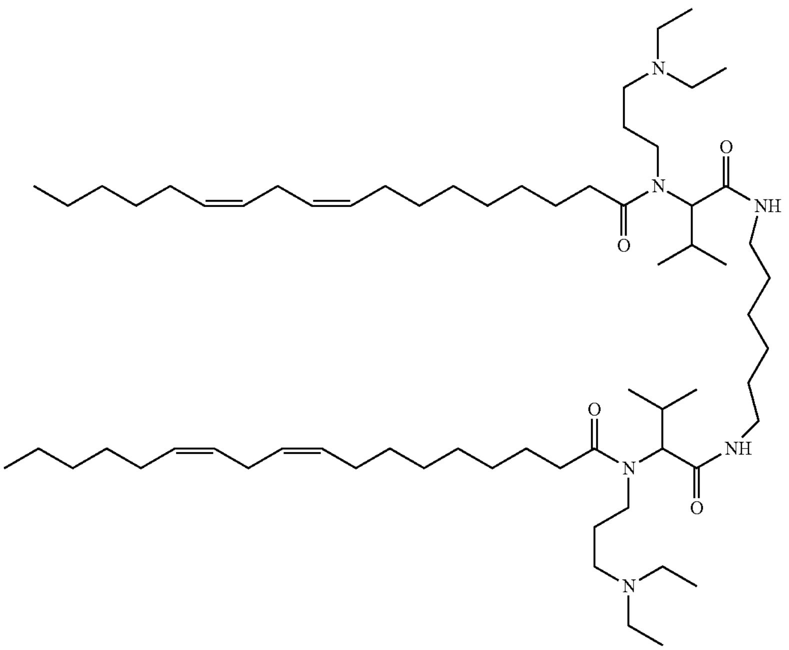
I1R5C12A1
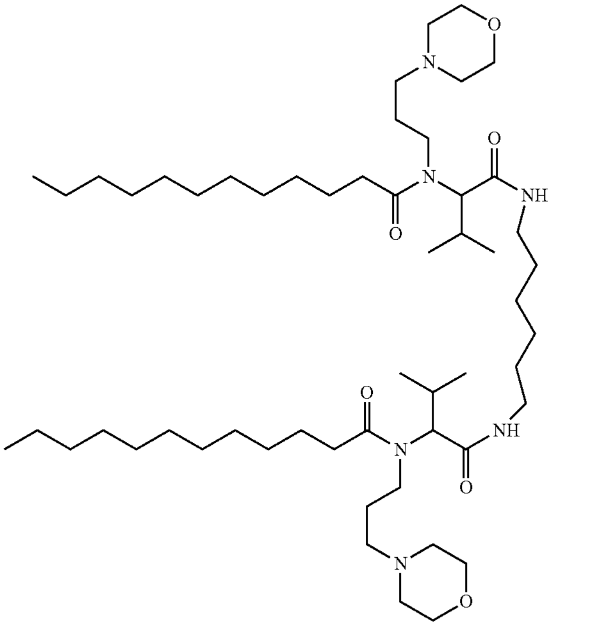
I1R5C14A1
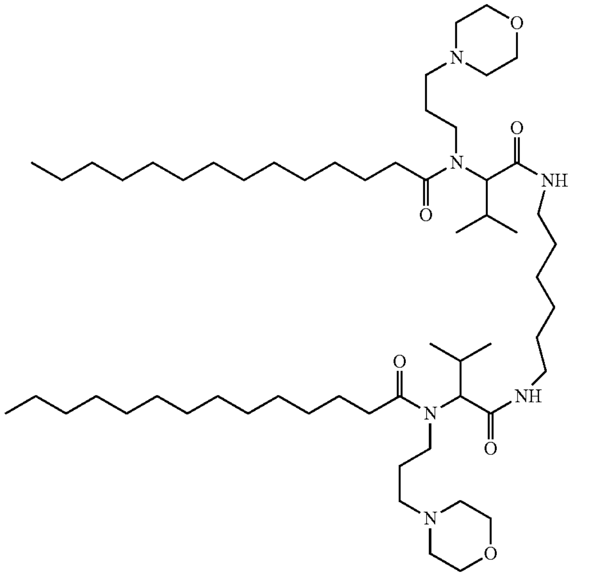

-continued
I1R5C16A1
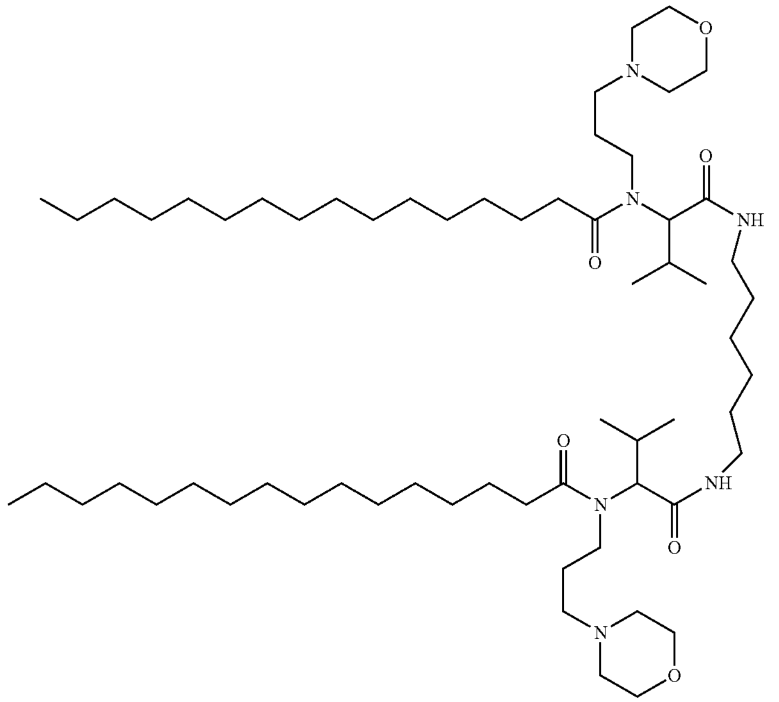
I1R5C18A1
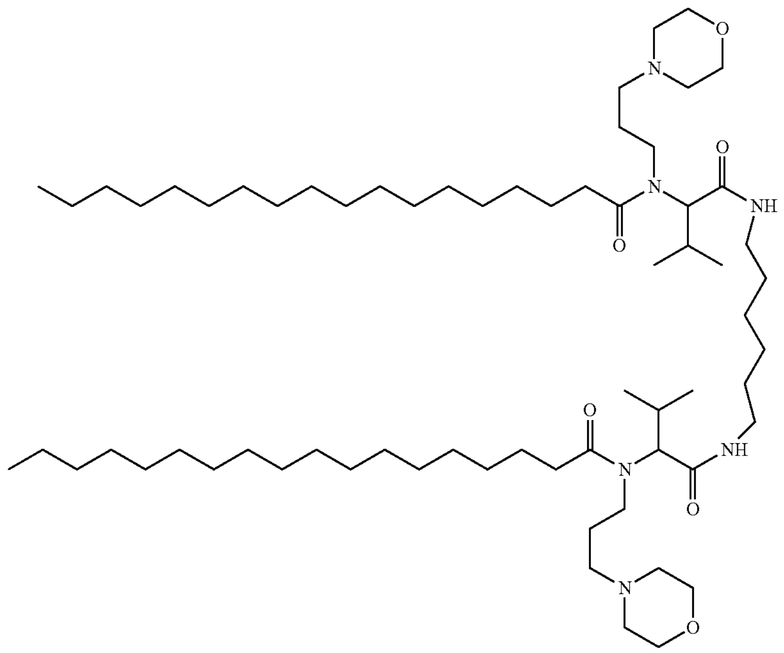

-continued
I1R5C20A1
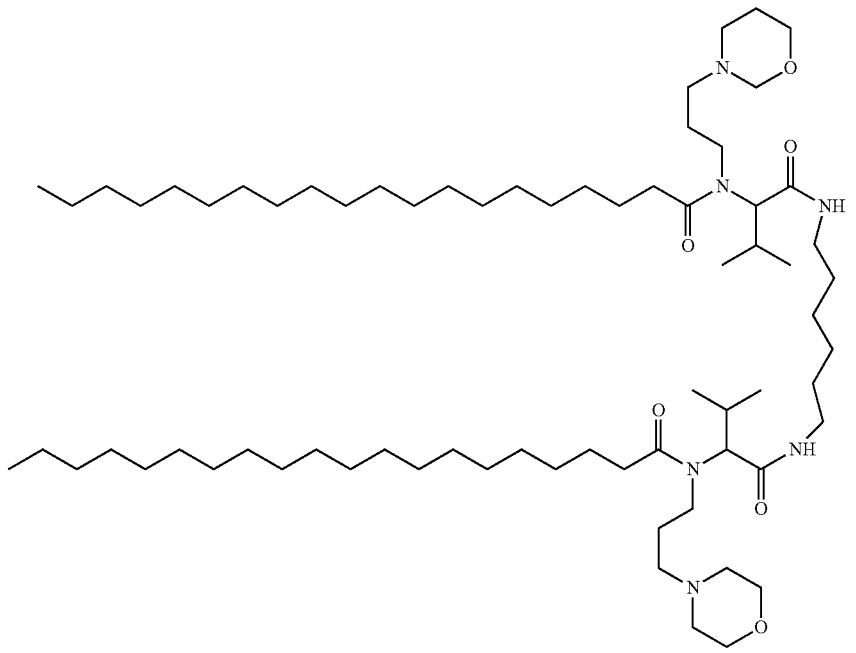
I1R5C18-1A1
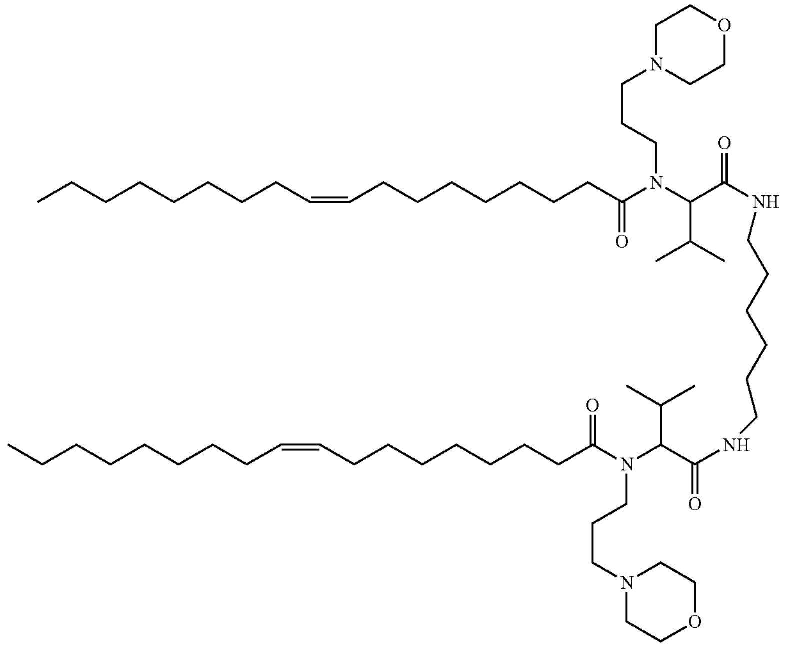

-continued
I1R5C18-2A1
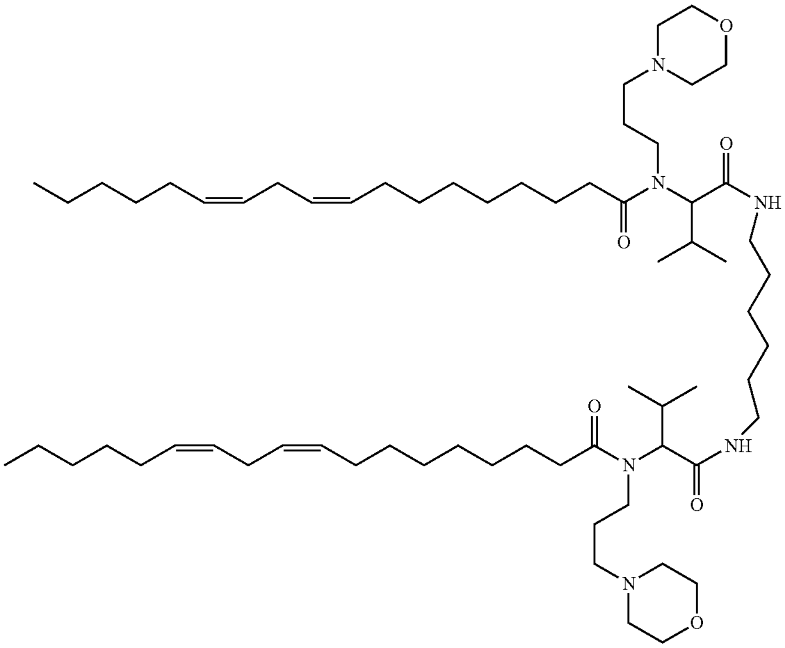
I1R11C12A1
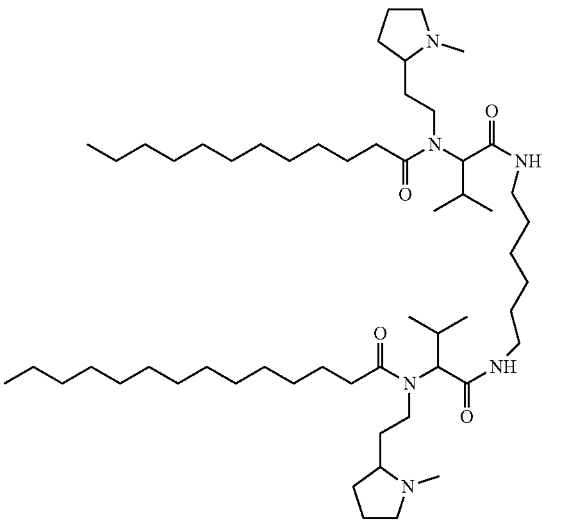
I1R11C14A1
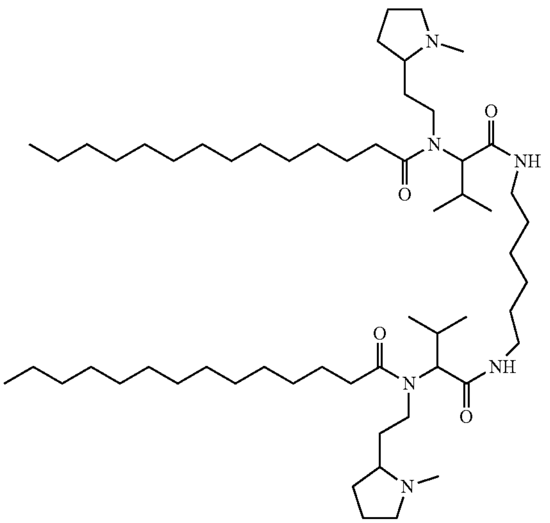

-continued
I1R11C16A1
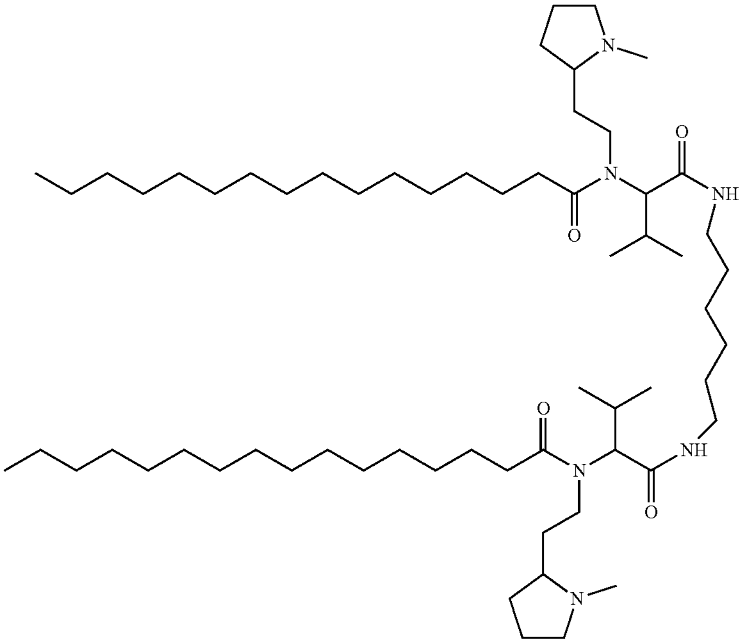
I1R11C18A1
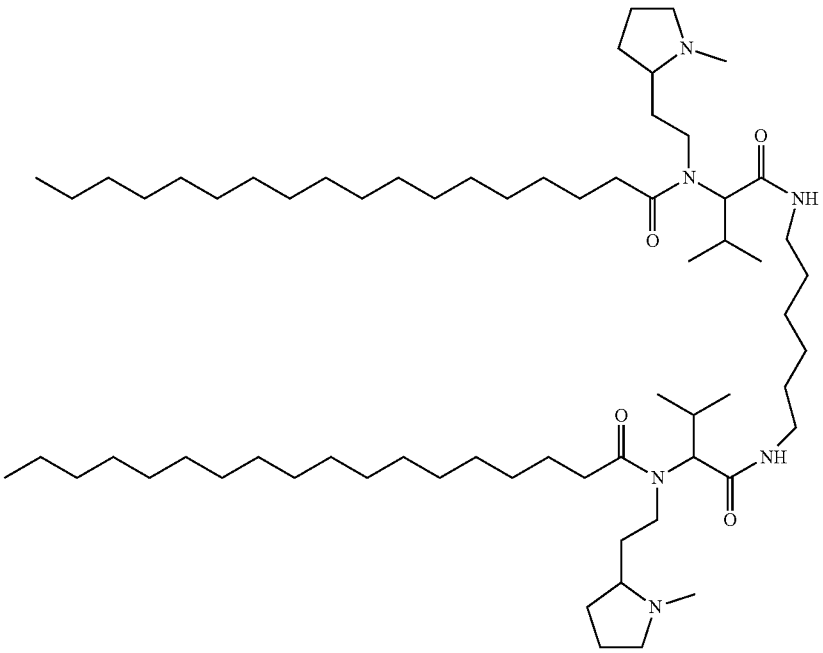

-continued
I1R11C20A1
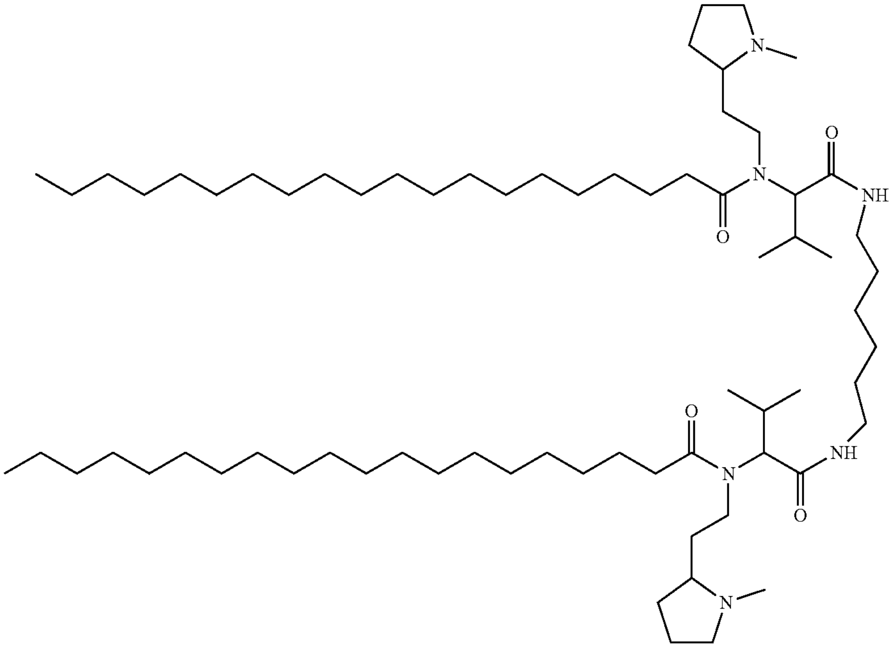
I1R11C18-1A1
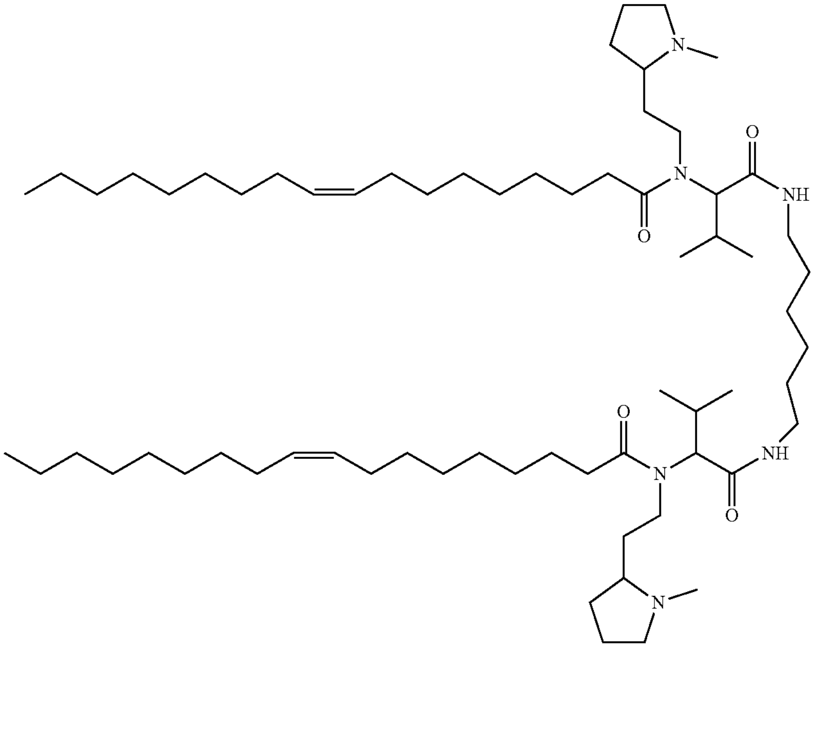

-continued
I1R11C18-2A1
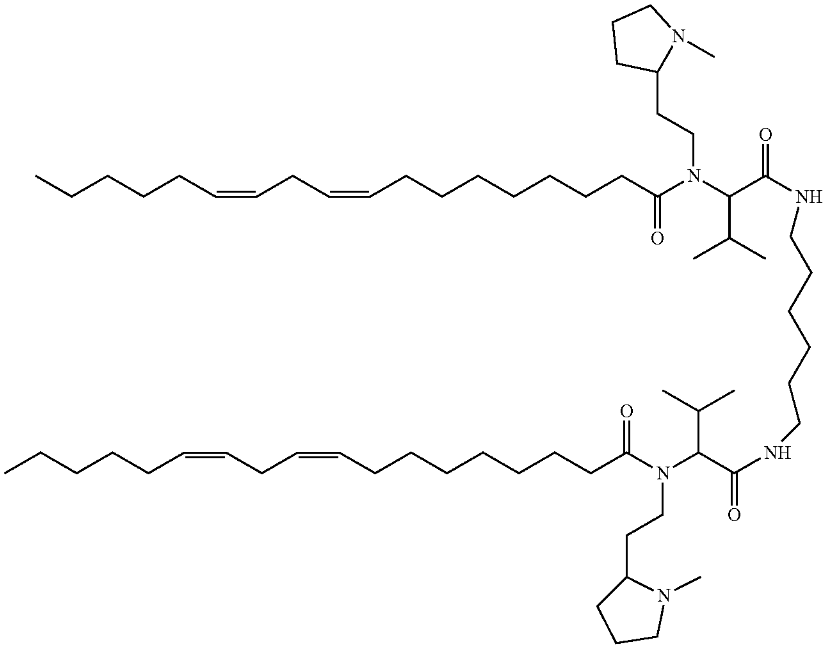
I2R1C12A1
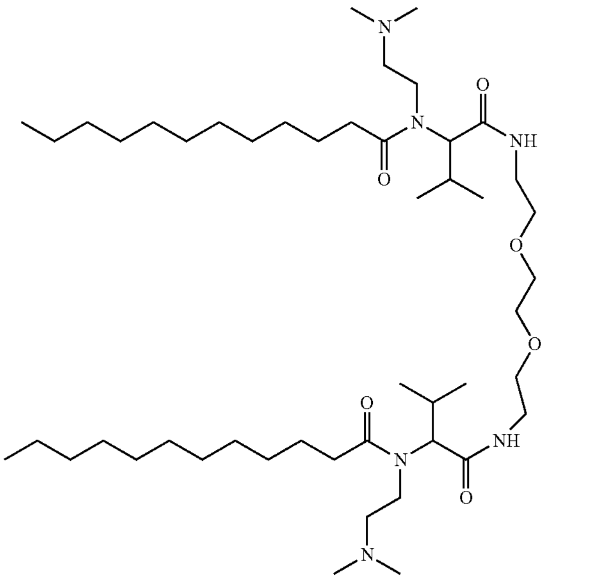
I2R1C14A1
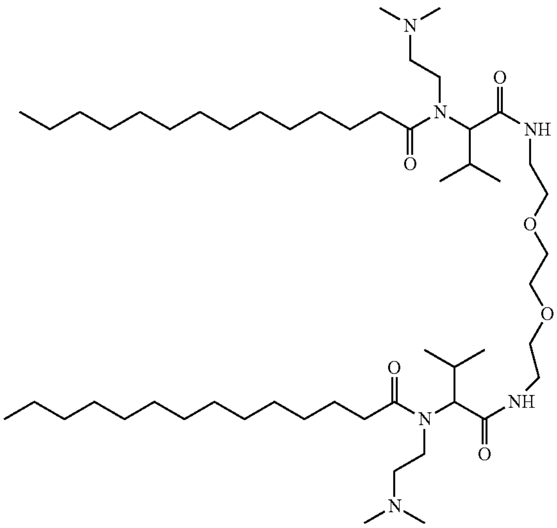

-continued
I2R1C16A1
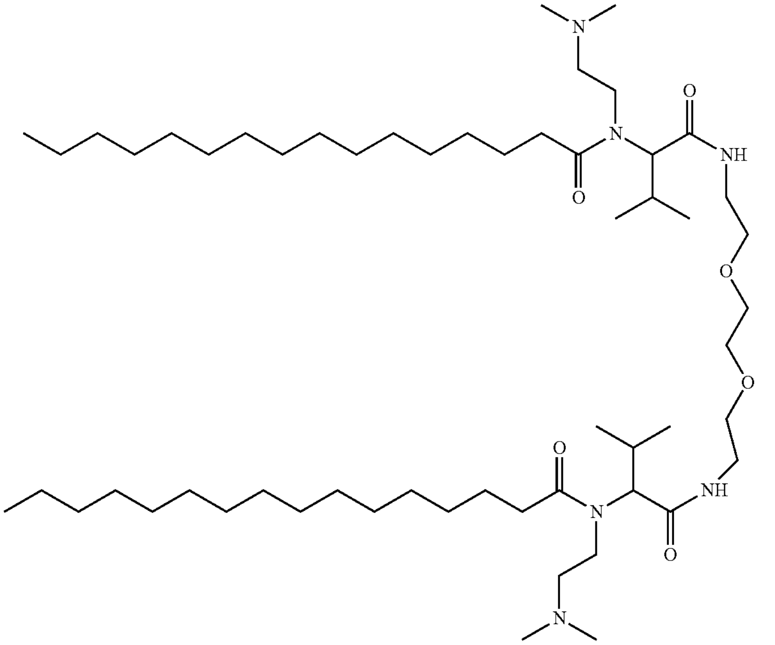
I2R1C18A1
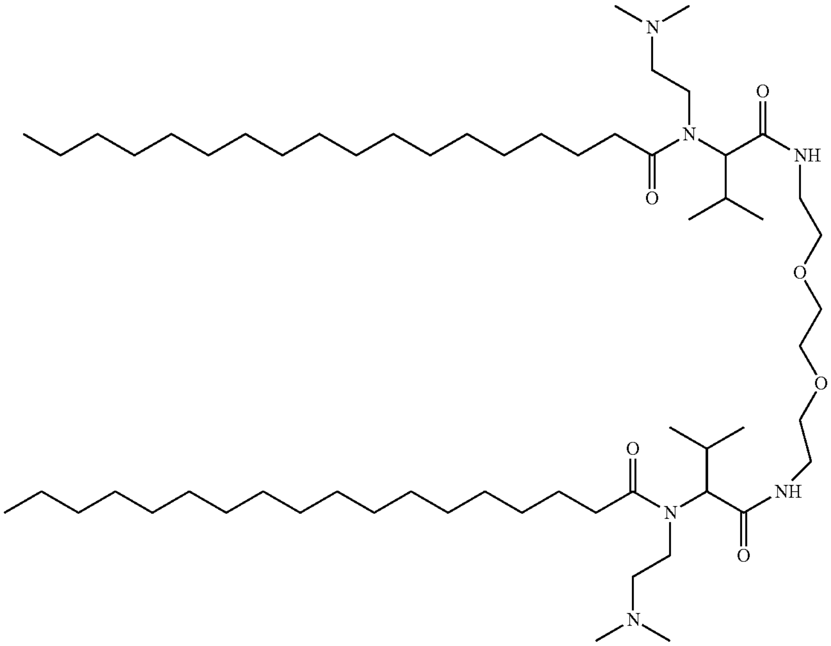

-continued
I2R1C20A1
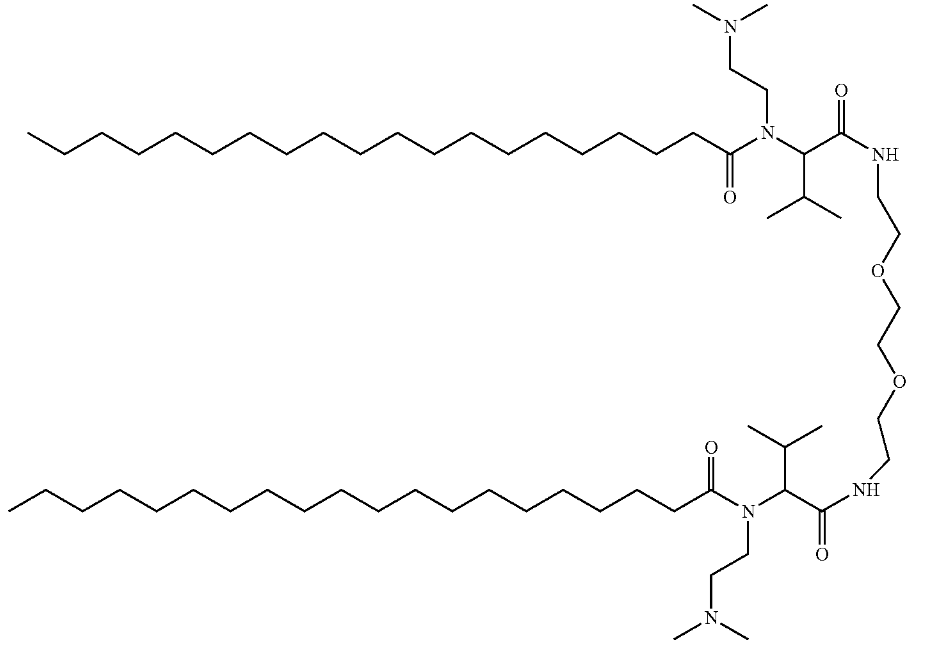
I2R1C18-1A1
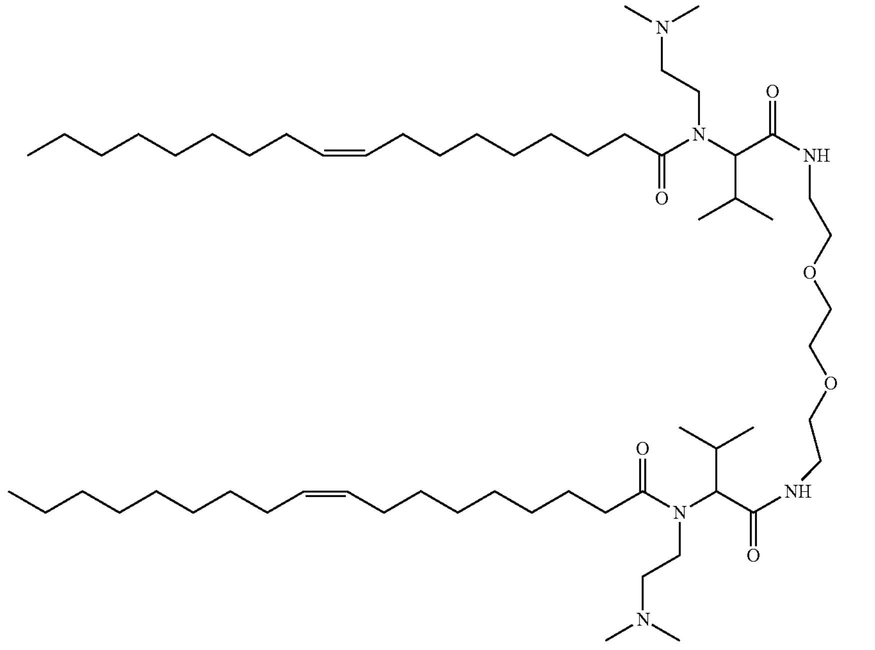

-continued
I2R1C18-2A1
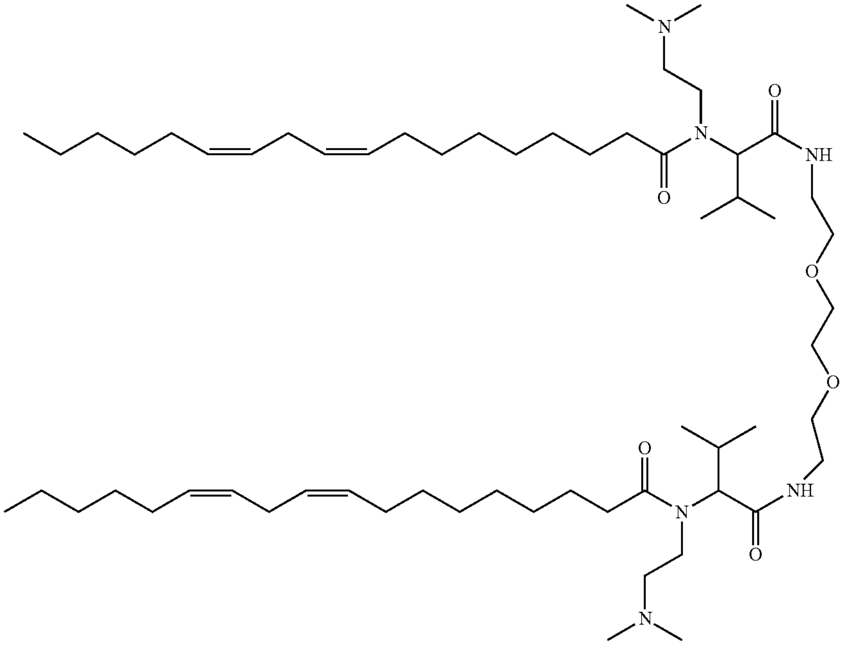
I2R2C12A1
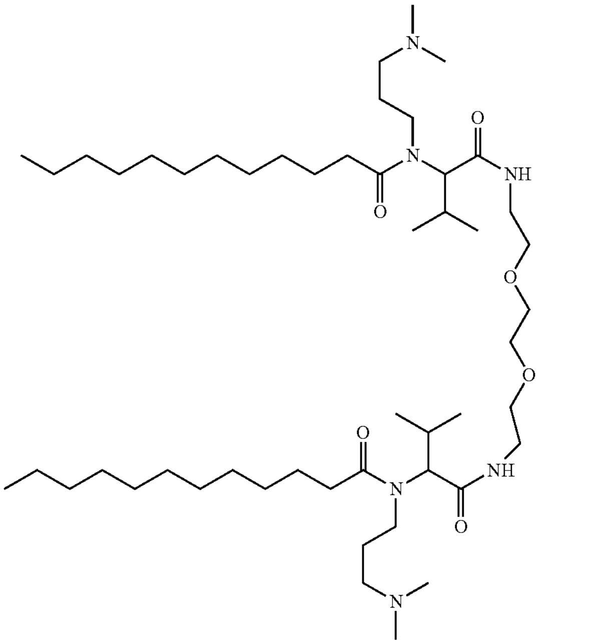
I2R2C14A1
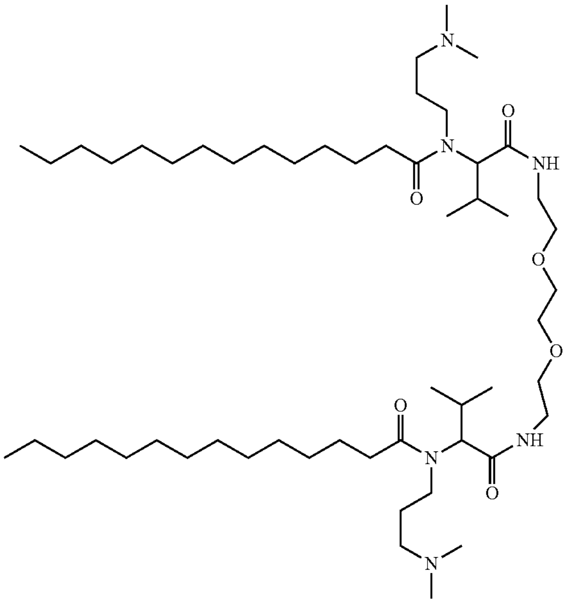

-continued
I2R2C16A1
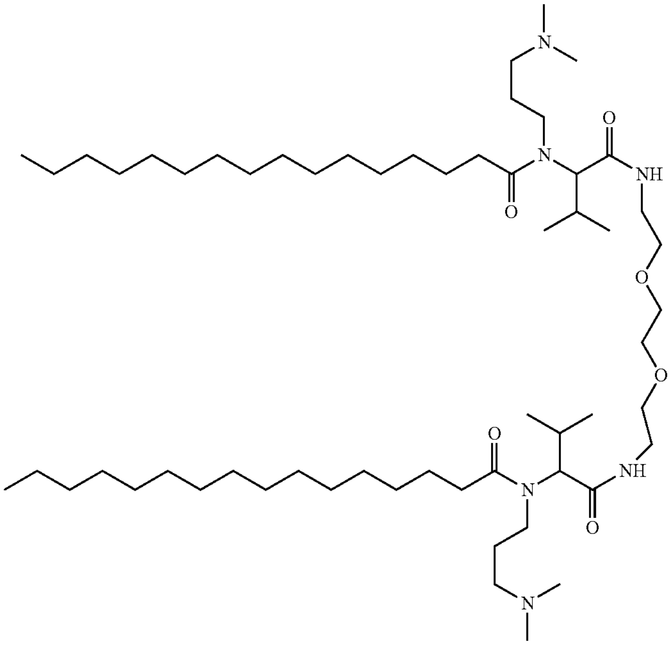
I2R2C18A1
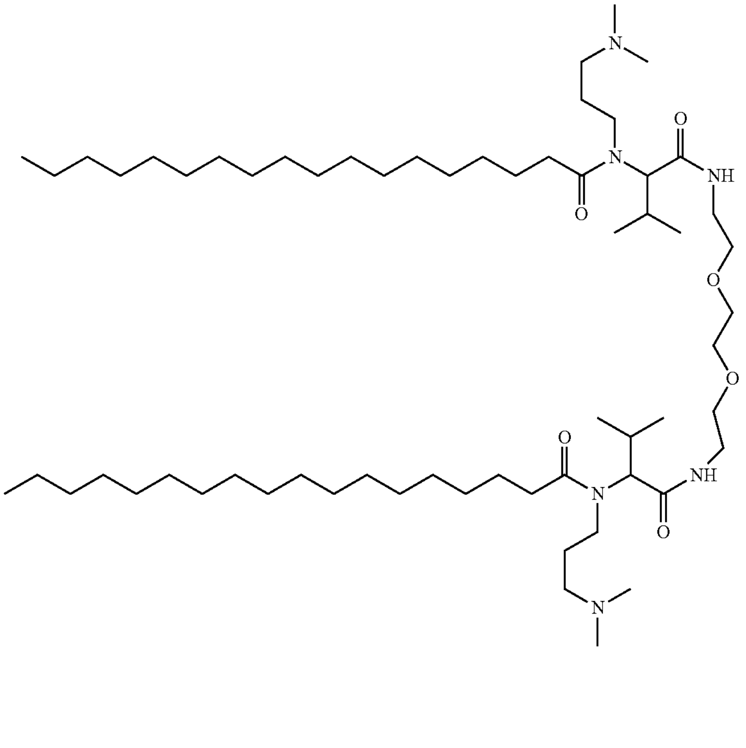

-continued
I2R2C20A1
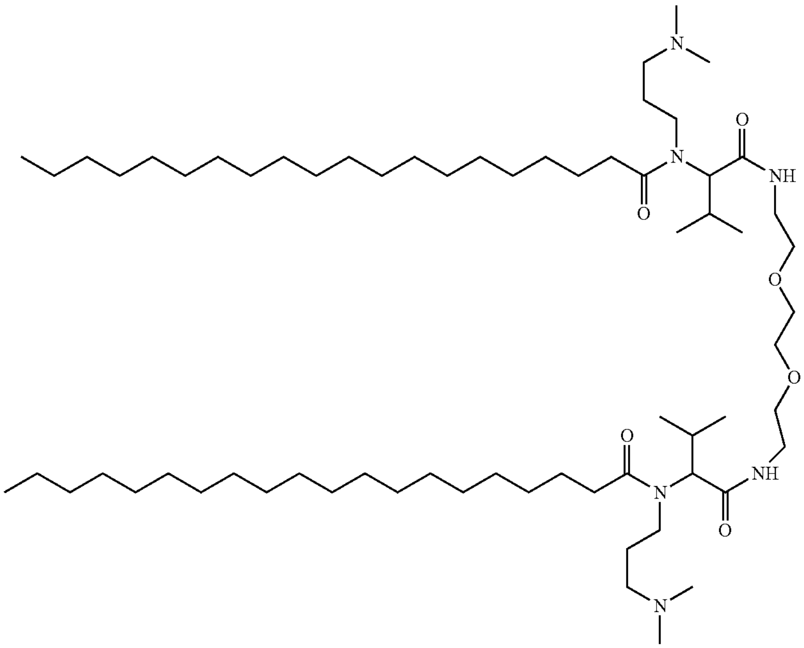
I2R2C18-1A1
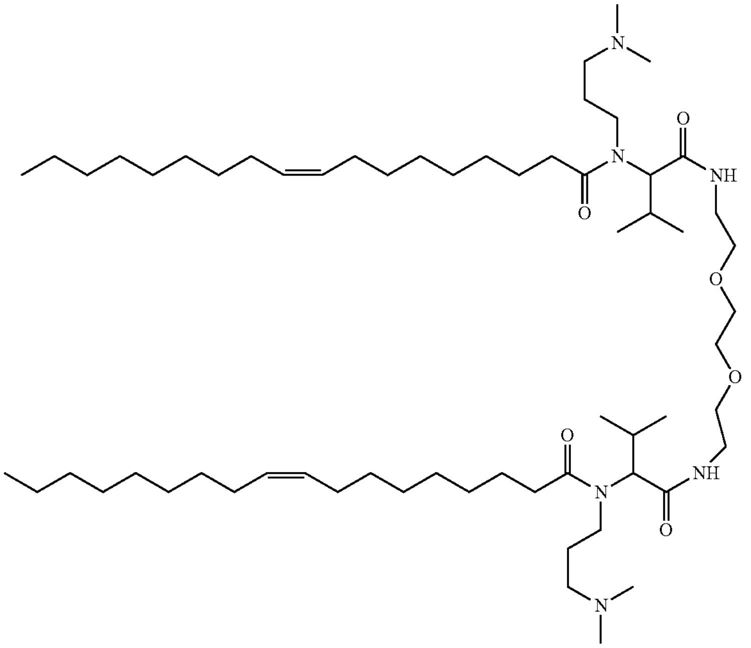

-continued
I2R2C18-2A1
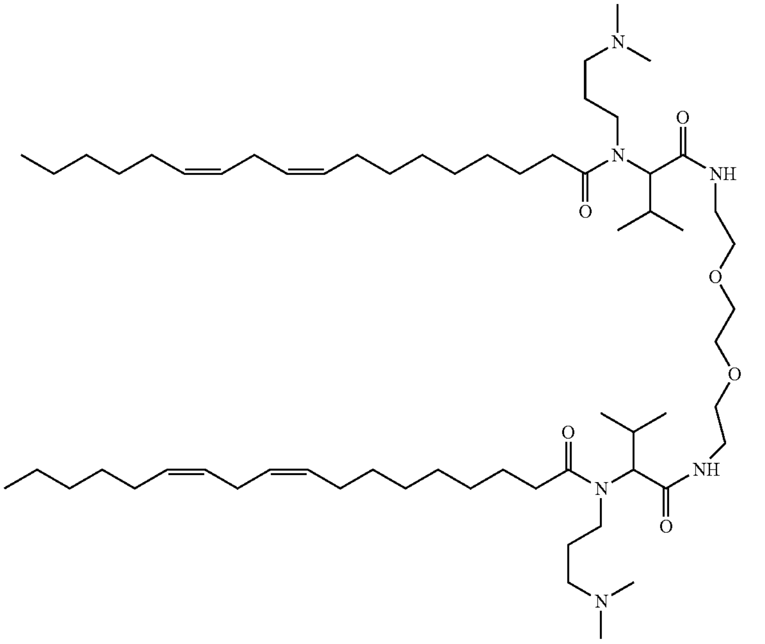
I2R3C12A1
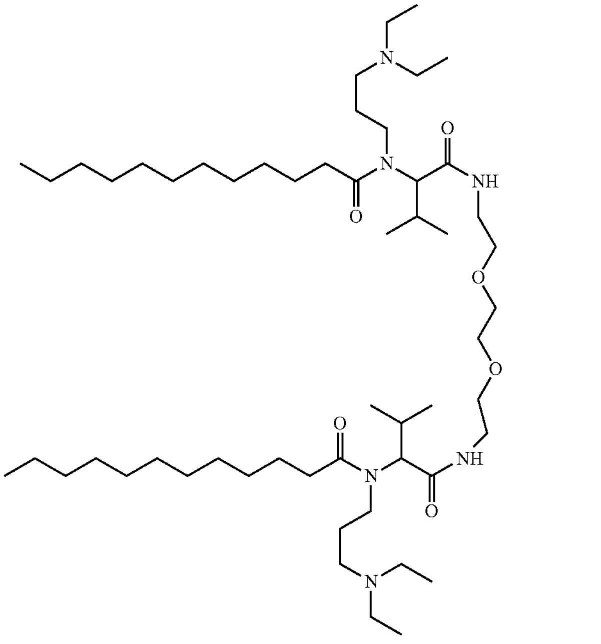
I2R3C14A1
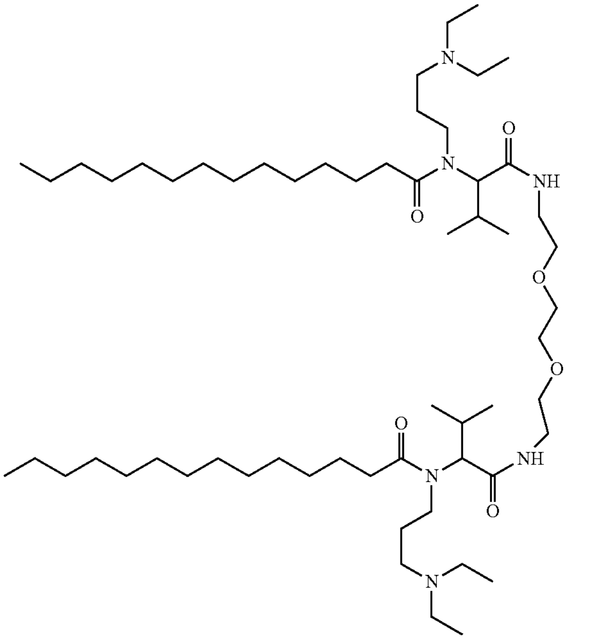

-continued
I2R3C16A1
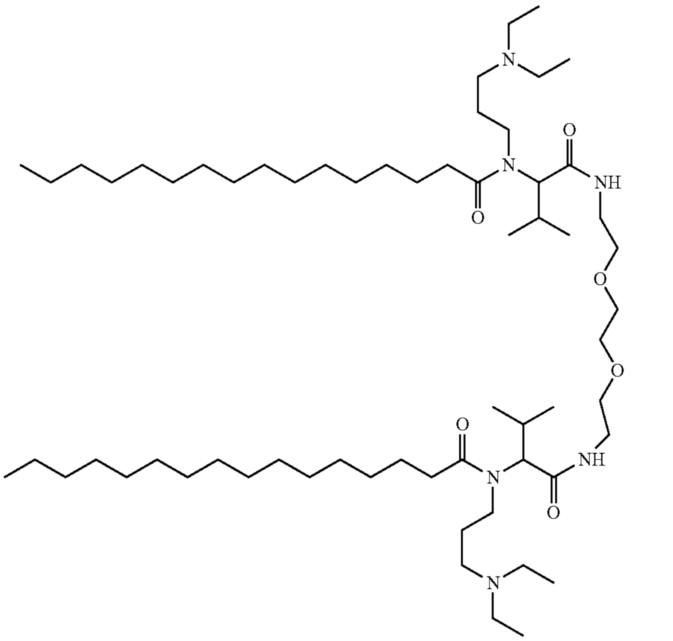
I2R3C18A1
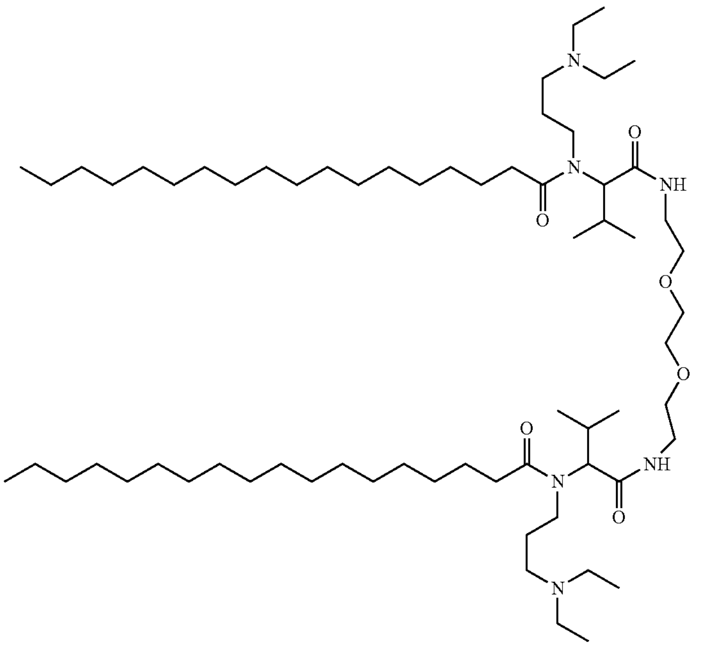

-continued
I2R3C20A1
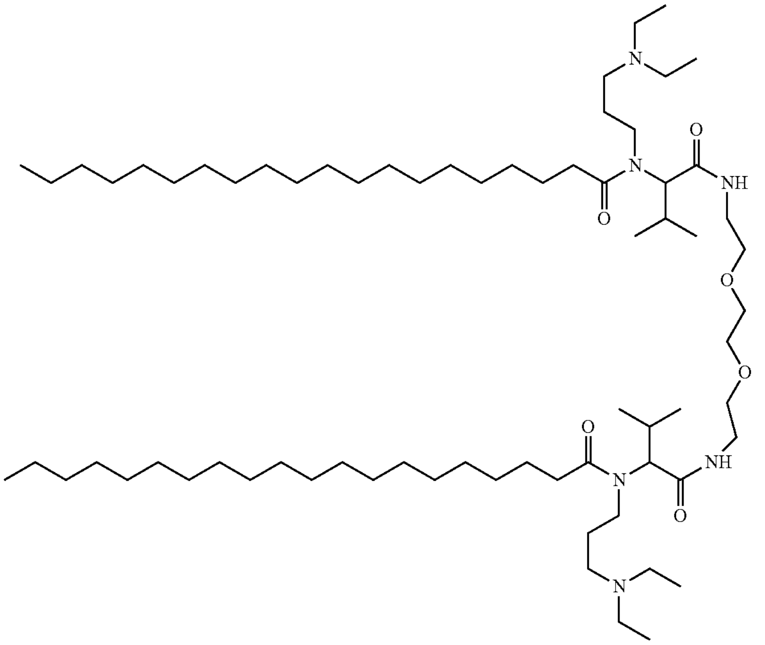
I2R3C18-1A1
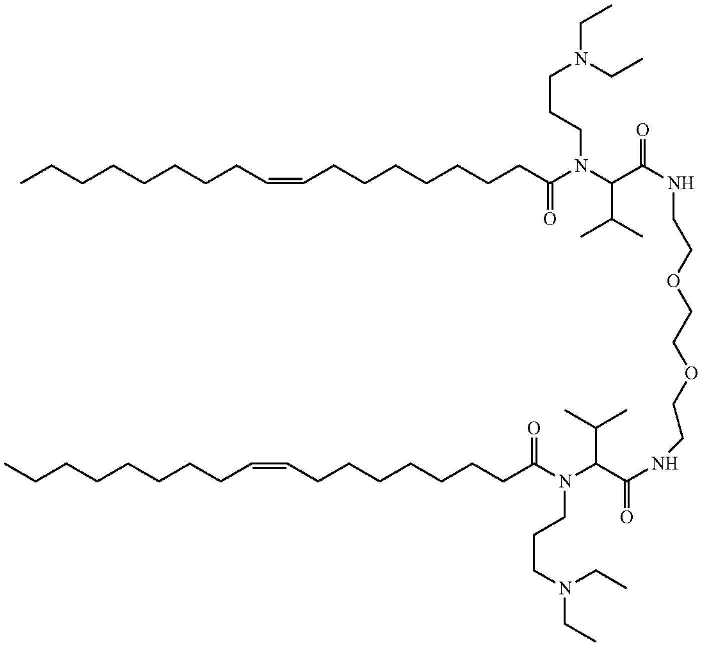

-continued
I2R3C18-2A1
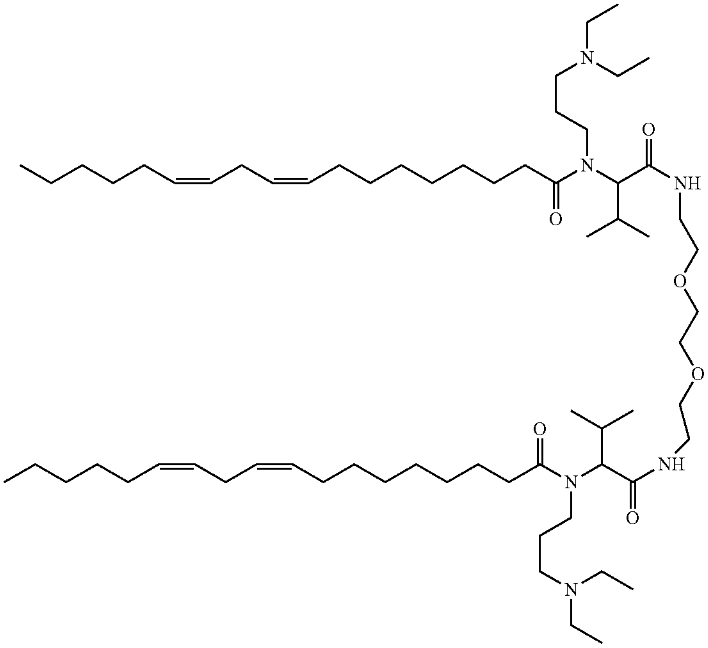
I2R5C12A1
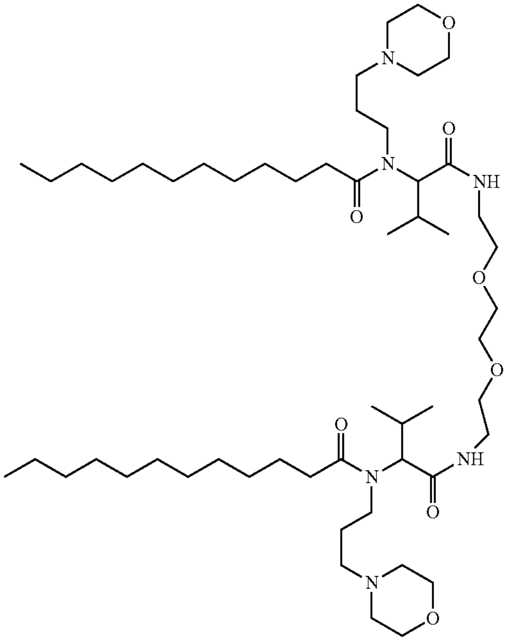
I2R5C14A1
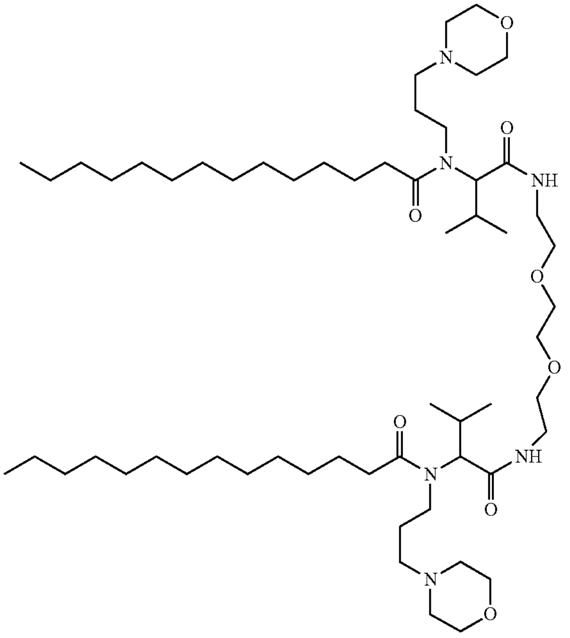

-continued
I2R5C16A1
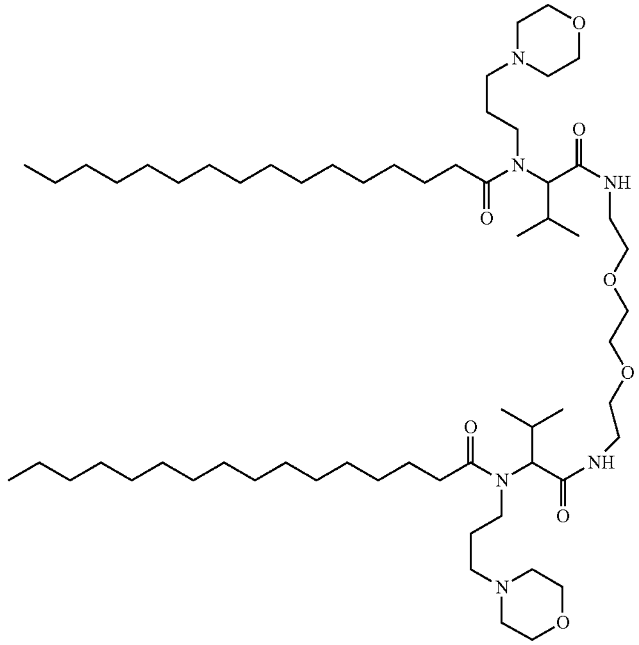
I2R5C18A1
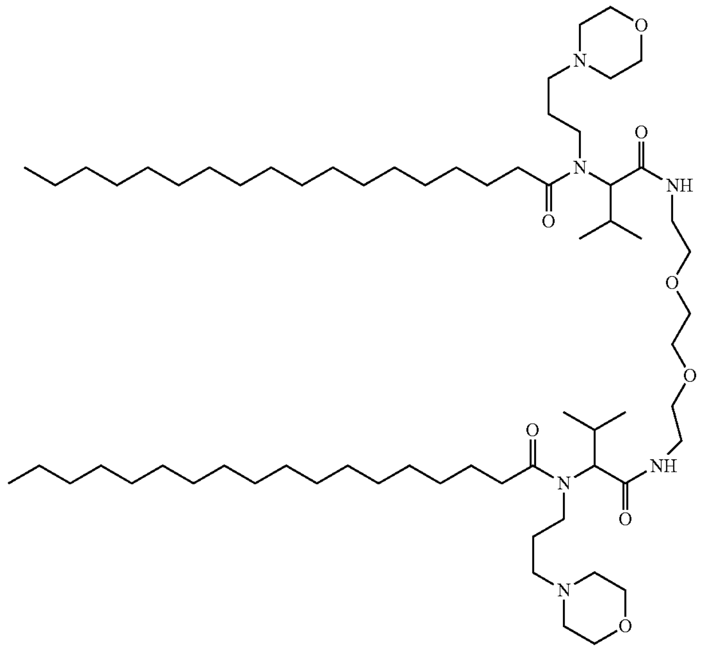

-continued
I2R5C20A1
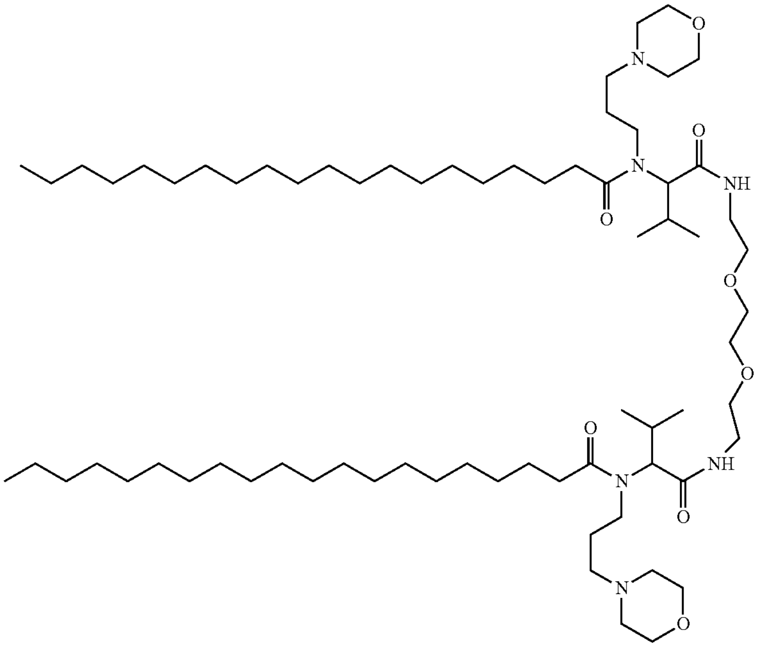
I2R5C18-1A1
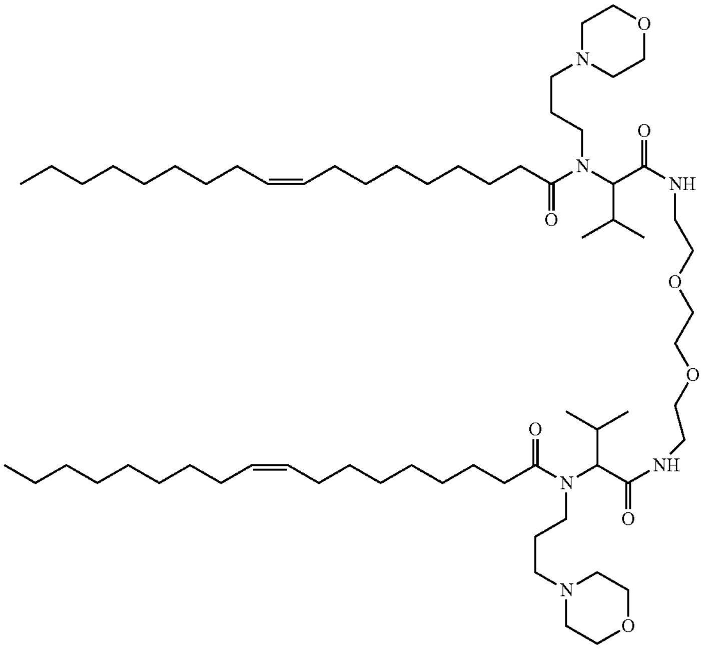

-continued
I2R5C18-2A1
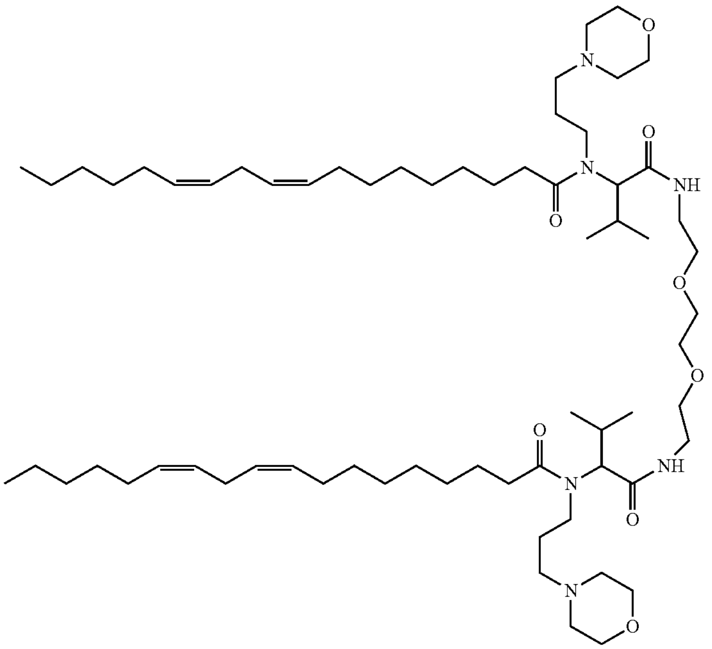
I2R11C12A1
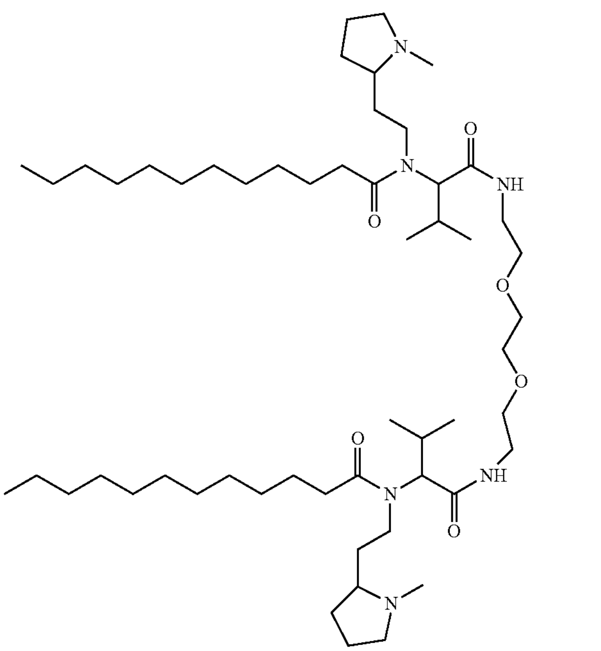
I2R11C14A1
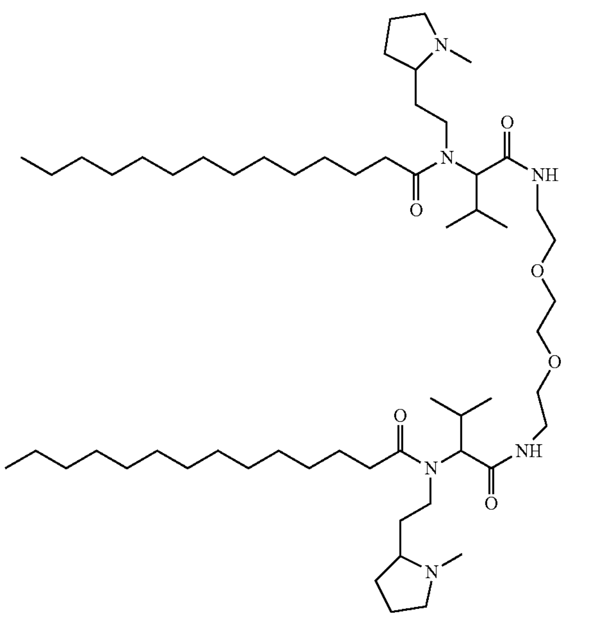

-continued
I2R11C16A1
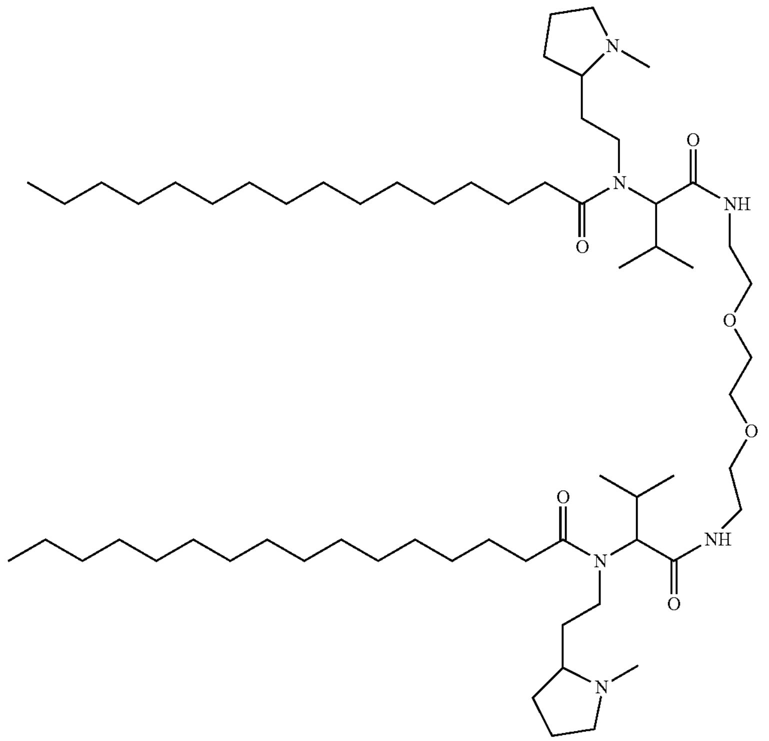
I2R11C18A1
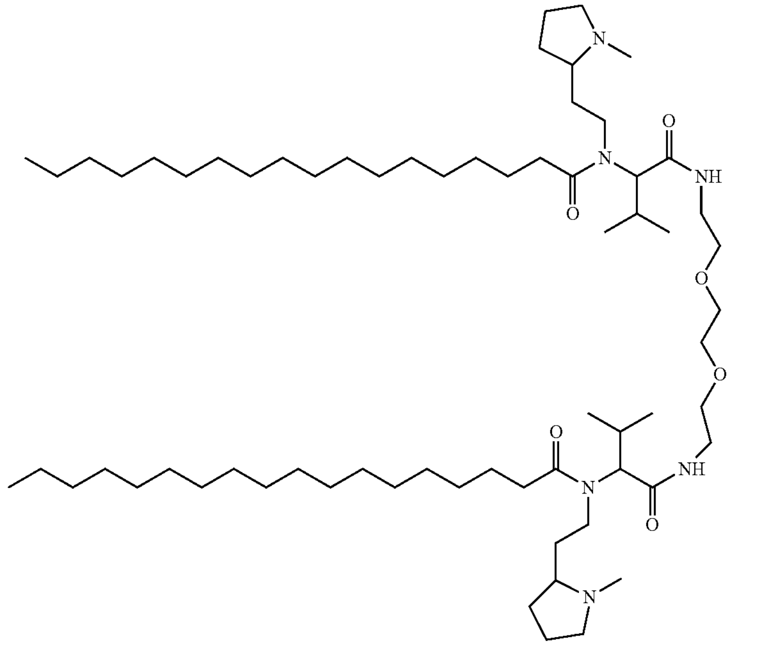

-continued
I2R11C20A1
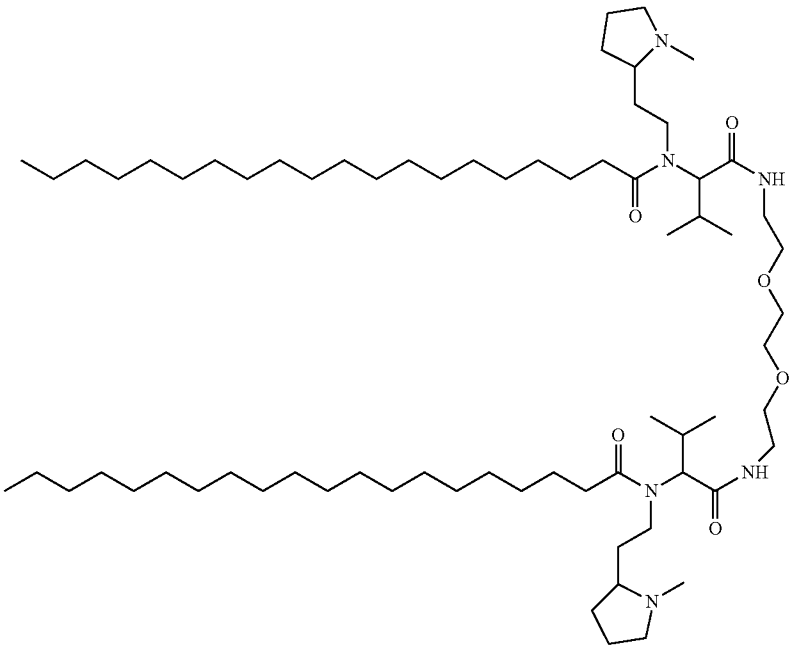
I2R11C18-1A1
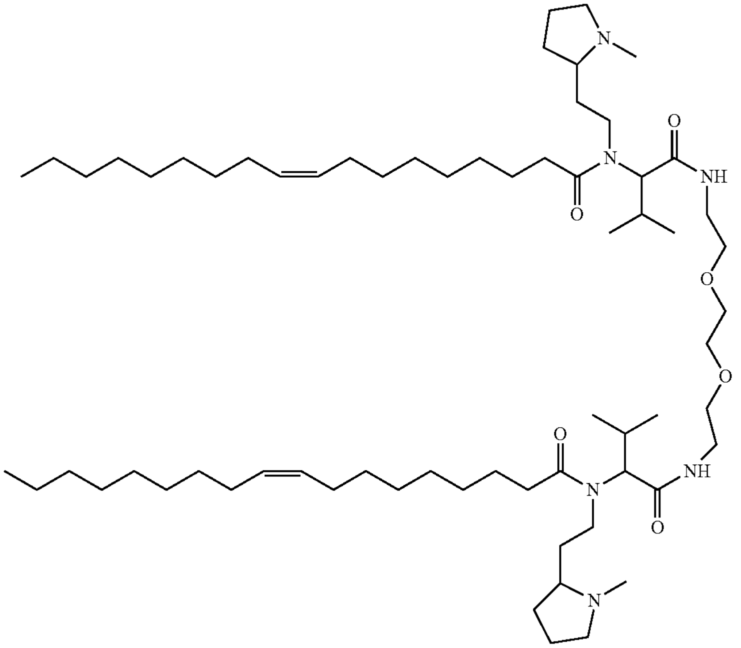

-continued
I2R11C18-2A1
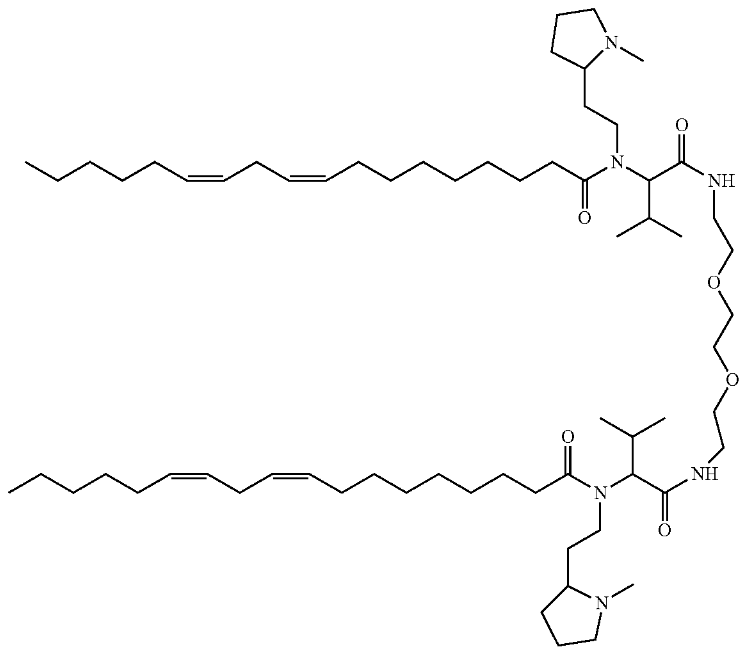
I2-1R2C18A1
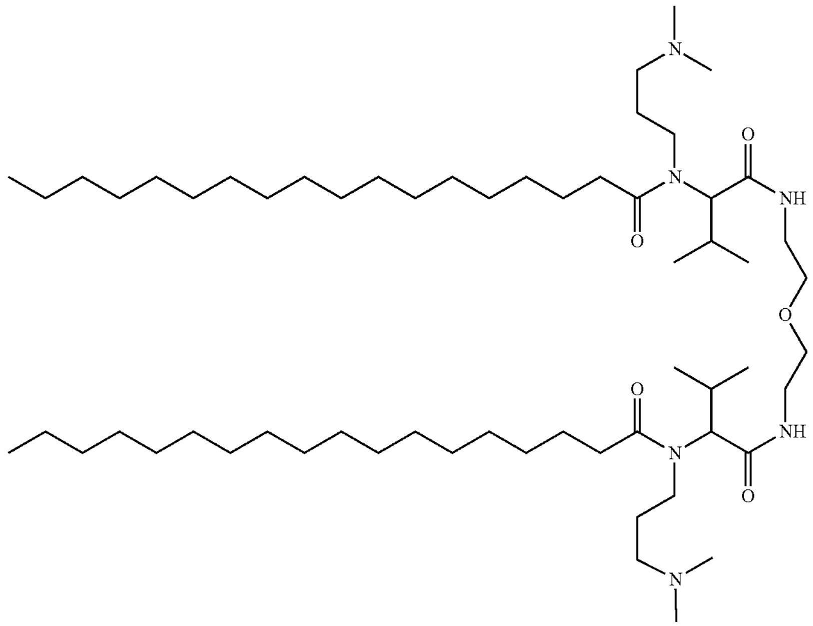

-continued

I2-3R2C18A1

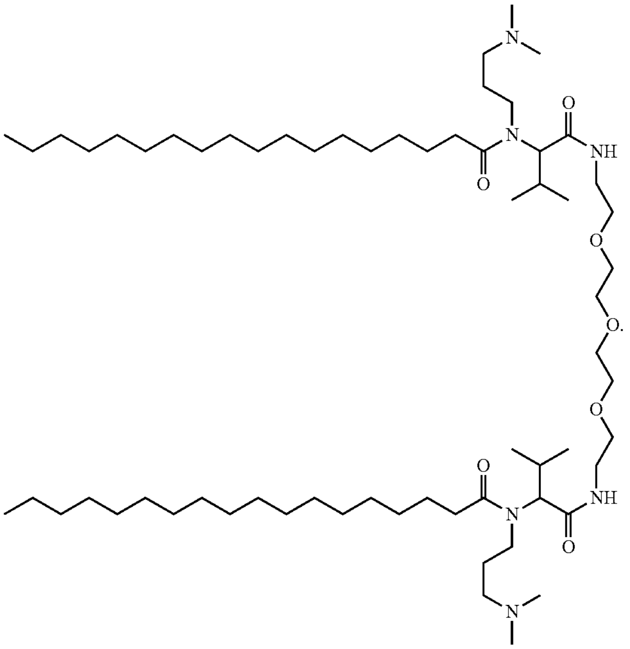

The inventors have found through experiments that the 72 small-molecule cationic lipid analog materials above can co-assemble with protein model drugs to form small and stable nano-complexes, and efficiently achieve the intracellular delivery of a variety of positively-charged proteins and negatively-charged proteins. Moreover, while achieving efficient intracellular delivery of proteins, the above materials and their corresponding complexes are less cytotoxic to ensure that the cells maintain normal physiological state after protein delivery.

In addition, the ionizable cationic lipid analog material is at least one selected from the group consisting of I2R2C15A1, I2R2C16A1, I2R2C17A1, I2R2C18A1, I2R2C19A1, I2R2C20A1, I2R3C18A1, I2R3C20A1, I2R11C16A1, I2R11C18A1, I2R11C20A1, I2-1R2C18A1, I2-3R2C18A1. In this application, bovine serum albumin labeled with fluorescein isothiocyanate (BSA-FITC) is used as a protein model to study the application effect of the cationic lipid analog material in intracellular protein delivery for HeLa. It is found that the delivery efficiency for proteins is closely related to the structure of the cationic lipid analog material, and the cationic lipid analog materials obtained by the above screening have high intracellular delivery efficiency. Moreover, their intracellular delivery efficiency is even at or above the level of current commercial reagents.

In addition, the protein drug comprises a negatively-charged protein drug and/or a positively-charged protein drug.

In addition, the protein drug is selected from the group consisting of fluorescein isothiocyanate-labeled bovine serum albumin (BSA-FITC), phycoerythrin (R-PE), superoxide dismutase, ovalbumin, green fluorescent protein, cytochrome C, or lysozyme.

In addition, the cell is selected from the group consisting of a renal epithelial cell, a pancreatic cancer cell, a macrophage, a dendritic cell, an umbilical vein endothelial cell, a mesenchymal stem cell (MSC), or a cervical cancer cell. Furthermore, the cell is from a human or a mouse. More preferably, the cell is a Hela cell.

The type or structure of the protein used in the present application is not specifically limited, and may be specifically a polypeptide, antibody, full-length protein, protein fragment, protein domain or fusion protein. The polypeptide may be an oligopeptide or a peptide. Proteins can be bioactive proteins because they have biological functions in a specific biological context, such as enzyme activity, binding to a target molecule of another protein or protein domain or nucleic acid sequence, hormonal activity, cell signaling activity, transcriptional activation or inhibitory activity, cell growth or cell cycle regulation, anticancer activity, or cytotoxin activity.

The ionizable cationic lipid analog material of the present application has universal applicability in the intracellular delivery of protein drugs, and is not limited to the molecular weight of the protein and the charged properties under physiological conditions. Moreover, the delivery of the protein into the cell can also maintain the biological activity of the protein. The protein comprises a negatively-charged protein and/or a positively-charged protein. The cationic lipid analog material of the present application can efficiently deliver proteins with different charges, including but not limited to one or more selected from the group consisting of the negatively-charged bovine serum albumin, negatively-charged phycoerythrin, negatively-charged superoxide dismutase, negatively-charged ovalbumin, negatively-charged green fluorescent protein, negatively-charged β-galactase, positively-charged cytochrome C, positively-charged saponin, and positively-charged lysozyme.

The preparation method of the cationic lipid analog material of the present application is as follows: adding an aldehyde compound and an amine compound to an organic solution; allowing to react for 10 min to 120 min before sequentially adding a carboxylic acid compound and an isocyanide compound; allowing to react at 4° C. to 60° C. for 6 h to 72 h; and separating and purifying a product by column chromatography after completion of reaction to obtain the cationic lipid analog material.

In the present application, the small-molecule cationic lipid analog material is synthesized through a Ugi reaction with the aldehyde compound, the amine compound, the carboxylic acid compound, and the isocyanide compound as raw materials. The reaction condition for the cationic lipid analog material of the present application is mild, and the synthesis process is simple and stable. The small-molecule cationic lipid analog material synthesized has low toxicity and can efficiently deliver protein drugs into cells.

In addition, in the preparation method of the cationic lipid analog material, a mixture of methanol and dichloromethane is used as a mobile phase for the separation with the chromatography column.

In addition, in the preparation method of the cationic lipid analog material, a molar ratio of the aldehyde compound, the amine compound, the carboxylic acid compound, and the isocyanide compound is (0.1-1):(0.1-1):(0.1-1):(0.1-1), and preferably the molar ratio is 1:1:1:0.5.

In addition, in the preparation method of the cationic lipid analog material, the aldehyde compound is any one selected from the group consisting of compounds A1 to A3:

A1

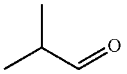

A2

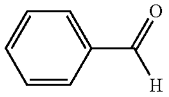

A3

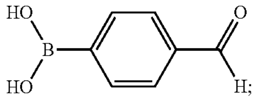

further, the aldehyde compound is preferably compound A1;

the amine compound is any one selected from the group consisting of compounds R1 to R11:

R1

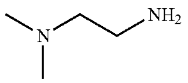

R2

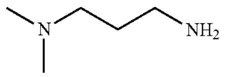

R3

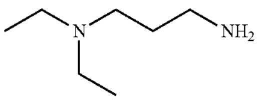

R4

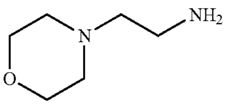

R5

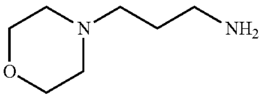

-continued

R6

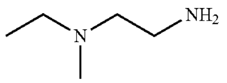

R7

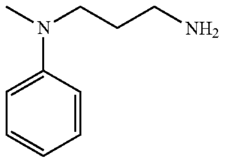

R8

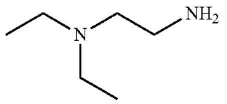

R9

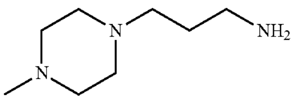

R10

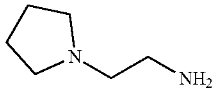

R11

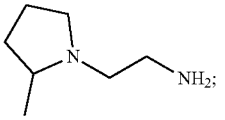

furthermore, the amine compound is any one selected from the group consisting of compounds R2, R3, or R11;

the carboxylic acid compound is any one selected from the group consisting of compounds CHS, C18-1, C18-2, or C8 to C20:

C8

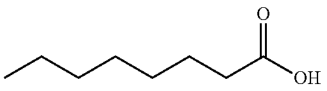

C9

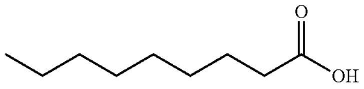

C10

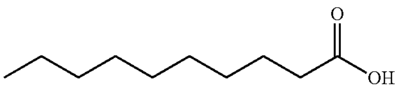

C11

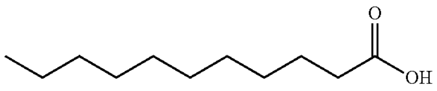

C12

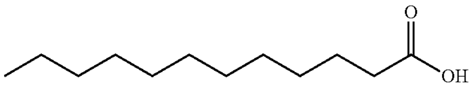

C13

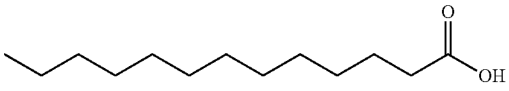

-continued

C14

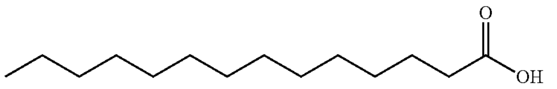

C15

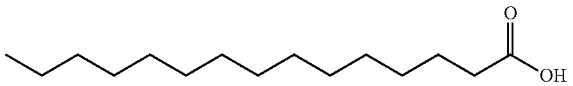

C16

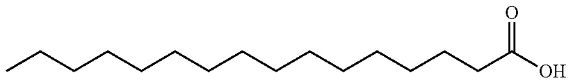

C17

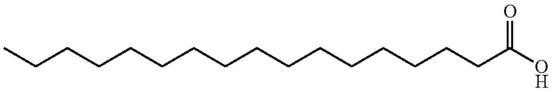

C18

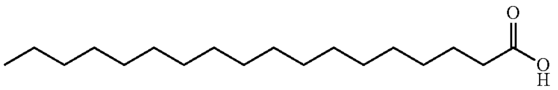

C19

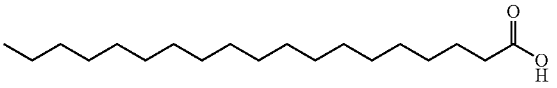

C20

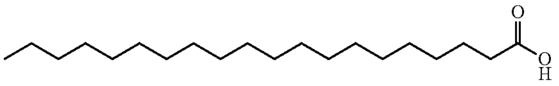

C18-1

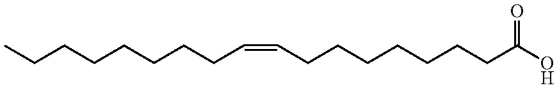

C18-2

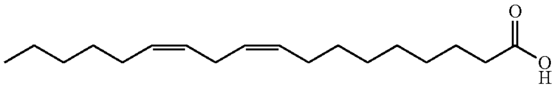

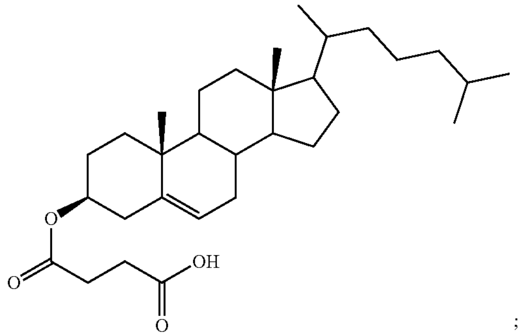

;

CHS furthermore, the carboxylic acid compound is any one selected from the group consisting of compounds C15 to C20;

the isocyanide compound is any one selected from the group consisting of compounds I1, I2-1, I2, I2-3, I3:

I1

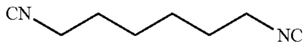

I2-1

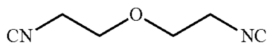

I2

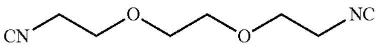

I2-3

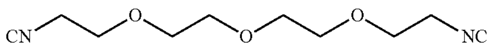

I3

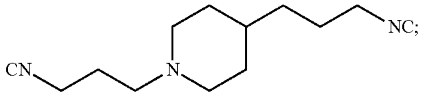

furthermore, the isocyanide compound is compound I2.

Compared with the prior art, the present application has the following beneficial effects:

In the present application, the novel ionizable cationic lipid analog material designed herein can allow an efficient intracellular delivery of proteins in different types of cells. Further, the material is effective for proteins of different molecular weights and charges, and the biological activity of the proteins can still be maintained when the proteins are delivered into the cell. At the same time, the ionizable cationic lipid analog material has low toxicity to cells and good biocompatibility, and can be used as delivery carriers for protein drugs.

DETAILED DESCRIPTION

Figure 1A:
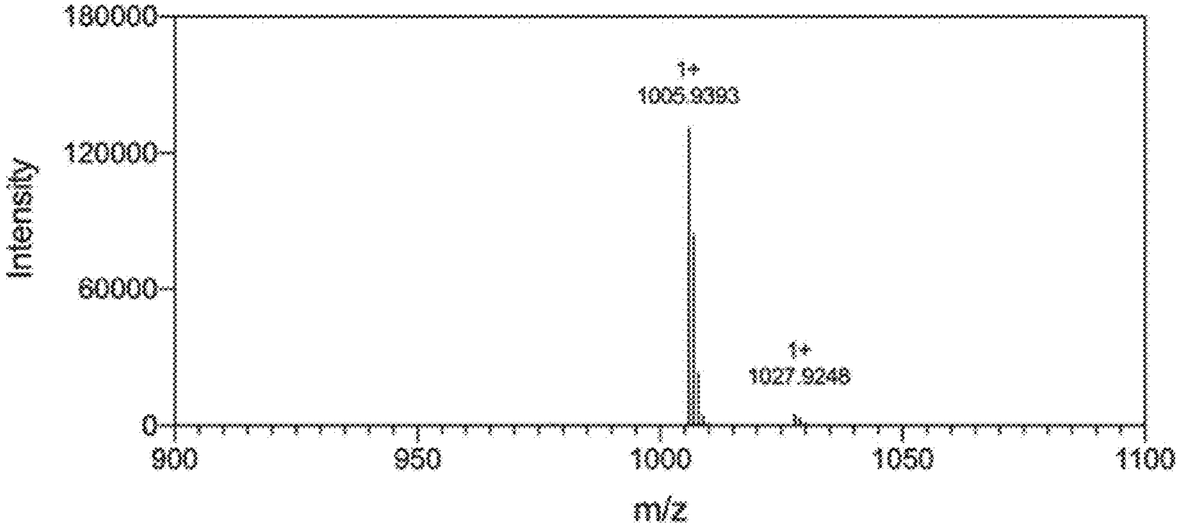
FIG. 1A shows a mass spectrometry spectrum of cationic lipid analog material I2-1R2C18A1.

In order to well illustrate the objectives, technical solutions, and advantages of the present application, the present application will be further described below in conjunction with specific examples. It should be understood by those skilled in the art that the specific examples described herein are merely intended to explain the present application, rather than to limit the present application.

In the examples, unless otherwise specified, the experimental methods used are conventional, and the materials and reagents used are commercially available.

Example 1 Synthesis and Characterization of Cationic Lipid Analog Materials

A synthesis route of the cationic lipid analog material of the present application was as follows:

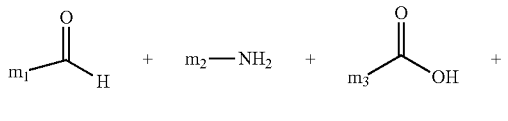

-continued

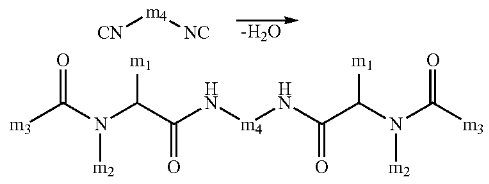

where the amine compound

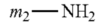

was any one selected from the group consisting of compounds R1 to R11 as follows; the carboxylic acid compound

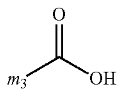

was any one selected from the group consisting of compounds C8 to C20, CHS as follows; the aldehyde compound

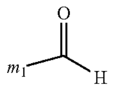

was any one selected from the group consisting of compounds A1 to A3 as follows; and the isocyanide compound

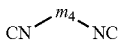

was any one selected from the group consisting of compounds I1 to I3 as follows:

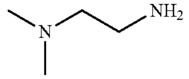

R1

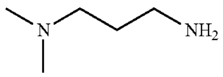

R2

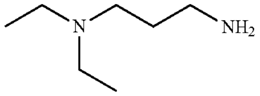

R3

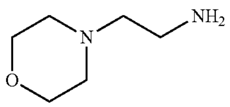

R4

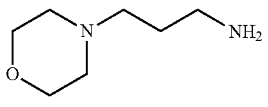

R5

-continued
R6
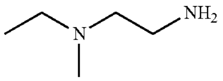
R7
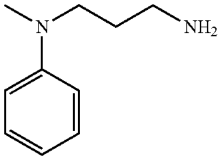
R8
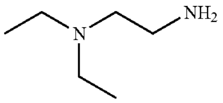
R9
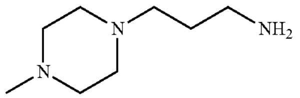
R10
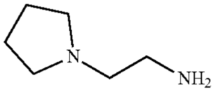
R11
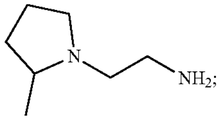
C8
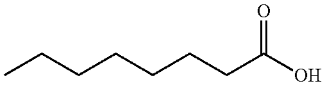
C9
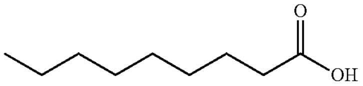
C10
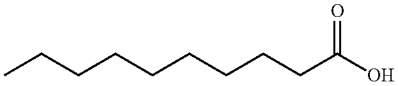
C11
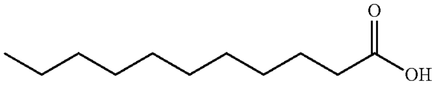
C12
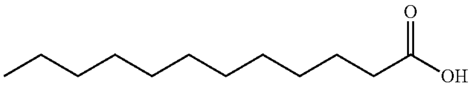
C13
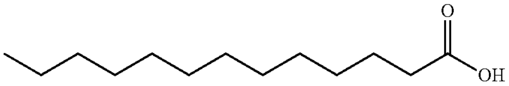
C14
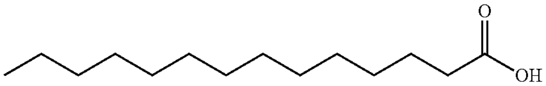
C15
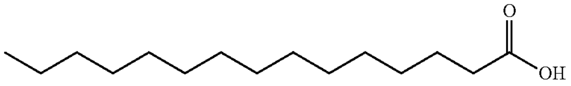
-continued
C16
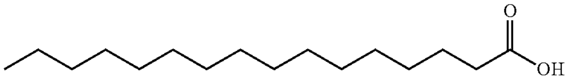
C17
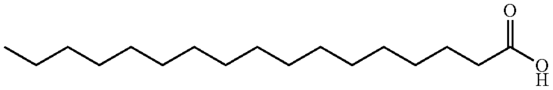
C18
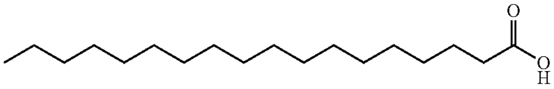
C19
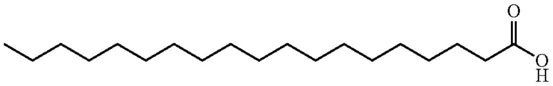
C20
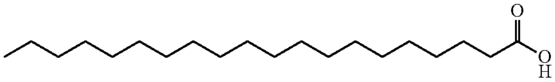
C18-1
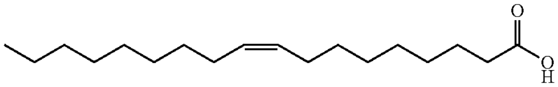
C18-2
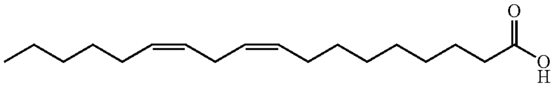
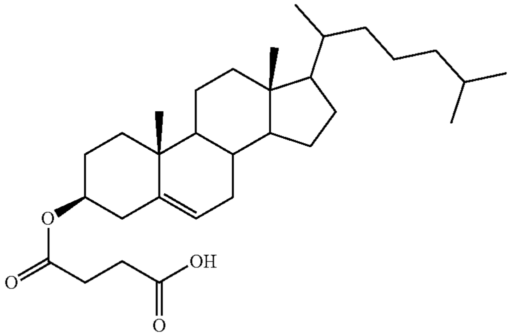
CHS
A1
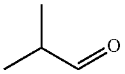
A2
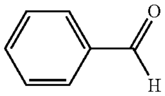
A3
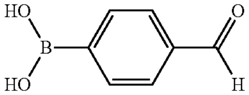
I1
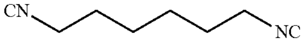
I2-1
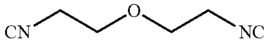

-continued

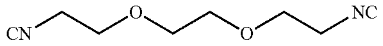

I2

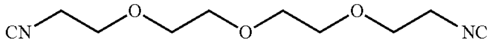

I2-3

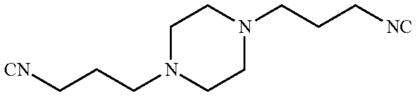

I3

A preparation method of the cationic lipid analog material in this example was specifically as follows: 1 mmol of isobutyl aldehyde and 1 mmol of an amine compound were added to 0.5 mL of a methanol solution, and a reaction was conducted for 60 min; 1 mmol of a carboxylic acid compound and 0.5 mmol of an isocyanide compound were added sequentially, and a reaction was conducted at 40° C. for 12 h; and after the reaction was completed, a product was separated and purified by a chromatography column, where a mixture of methanol and dichloromethane was adopted as a mobile phase.

Raw materials used in this example and structures of cationic lipid analog materials synthesized thereby were shown in Table 1.

TABLE 1

| | Isocyanide compound | Amine compound | Carboxylic acid compound | Aldehyde compound | Cationic lipid analog material (number and structural formula) |
|---|---|---|---|---|---|
| 1 | I1 | R1 | C12 | A1 | I1R1C12A1 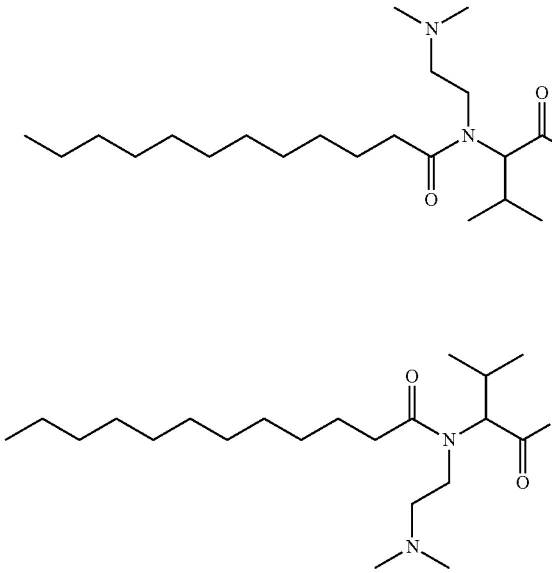 |
| 2 | I1 | R1 | C14 | A1 | I1R1C14A1 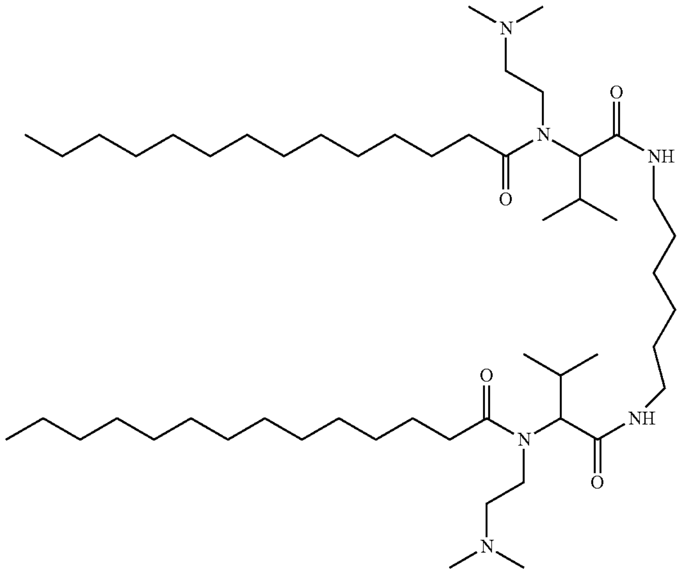 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 3 | I1 | R1 | C16 | A1 | I1R1C16A1 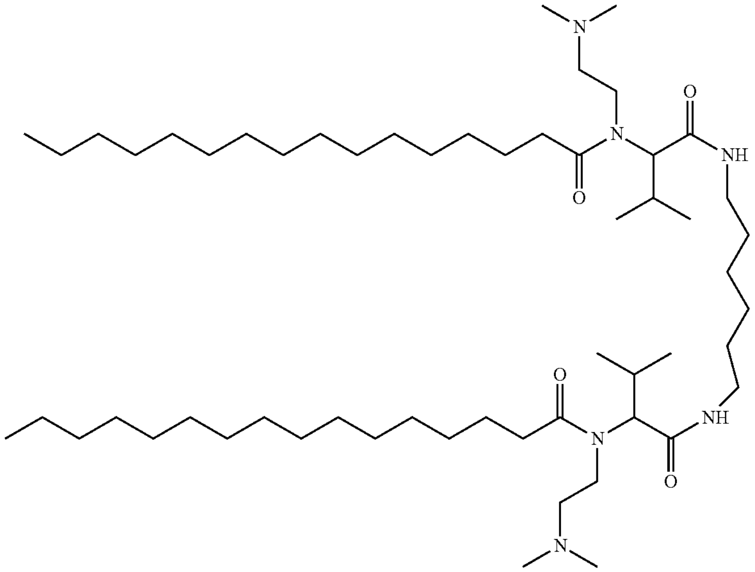 |
| 4 | I1 | R1 | C18 | A1 | I1R1C18A1 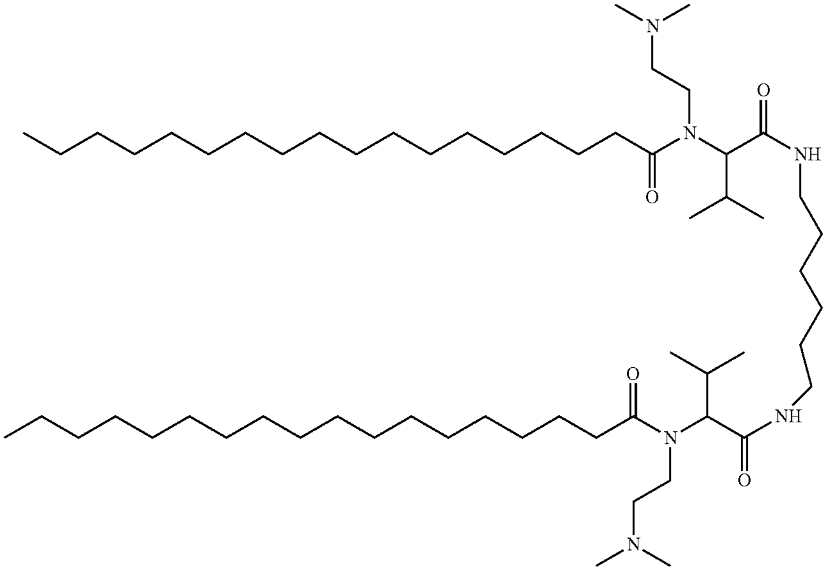 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 5 | I1 | R1 | C20 | A1 | I1R1C20A1 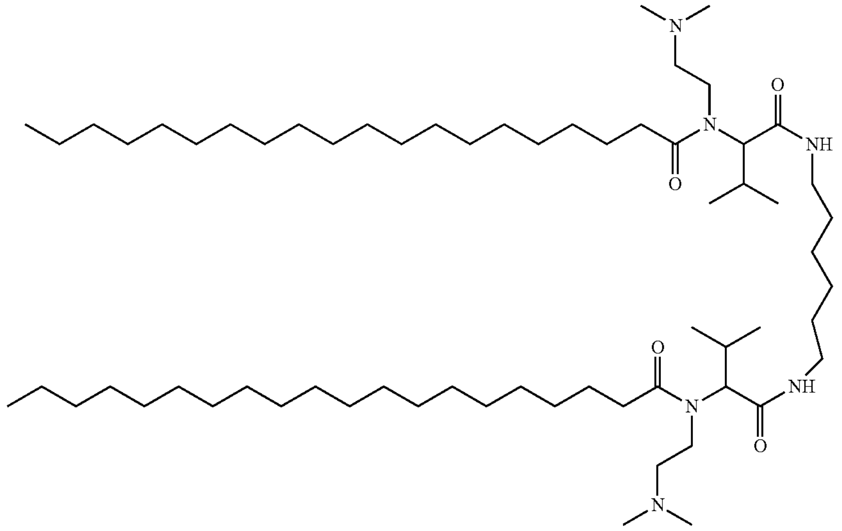 |
| 6 | I1 | R1 | C18-1 | A1 | I1R1C18-1A1 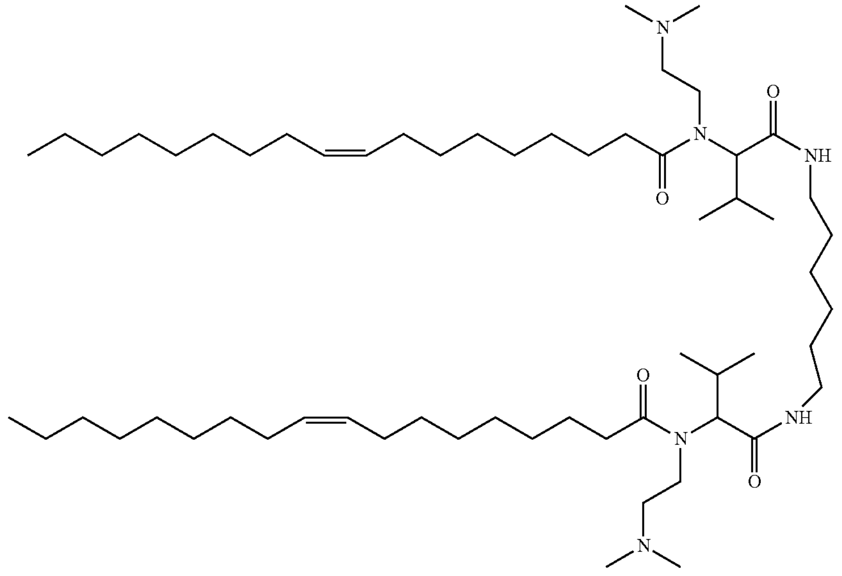 |

TABLE 1-continued
| | Iso-cyanide compound | Amine compound | Carboxylic acid compound | Aldehyde compound | Cationic lipid analog material (number and structural formula) |
|---|---|---|---|---|---|
| 7 | I1 | R1 | C18-2 | A1 | I1R1C18-2A1 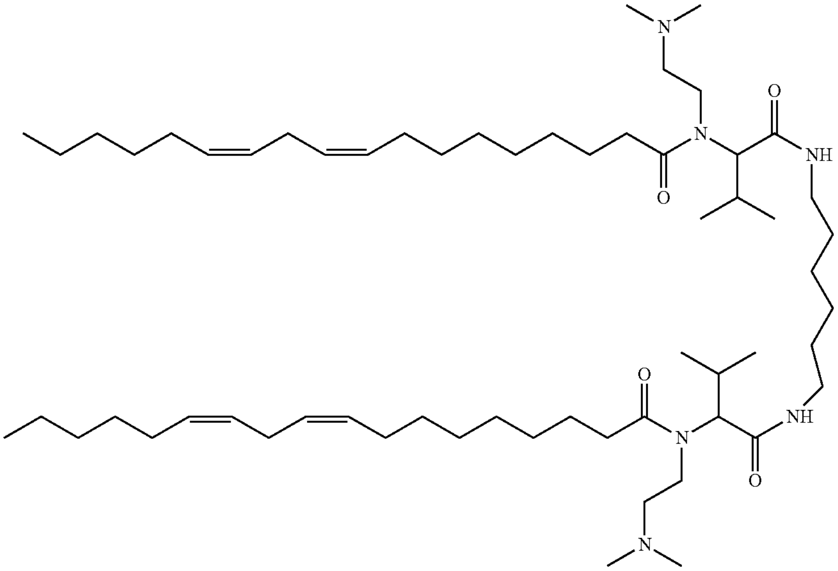 [SMILES: CCCCC/C=C\C/C=C\CCCCCCCC(=O)N(CCN(C)C)C(C(=O)NCCCCCCNC(=O)C(C(C)C)N(CCN(C)C)C(=O)CCCCCCC/C=C\C/C=C\CCCCC)C(C)C] |
| 8 | I1 | R2 | C12 | A1 | I1R2C12A1 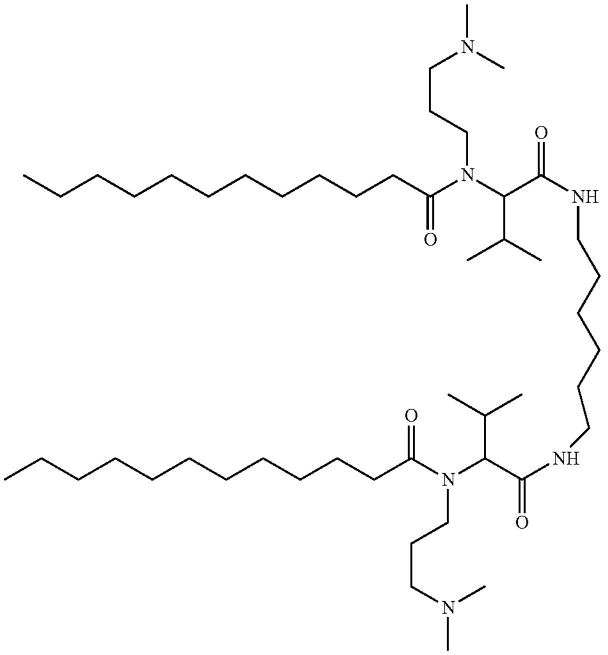 [SMILES: CCCCCCCCCCCC(=O)N(CCCN(C)C)C(C(=O)NCCCCCCNC(=O)C(C(C)C)N(CCCN(C)C)C(=O)CCCCCCCCCCC)C(C)C] |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 9 | I1 | R2 | C14 | A1 | I1R2C14A1 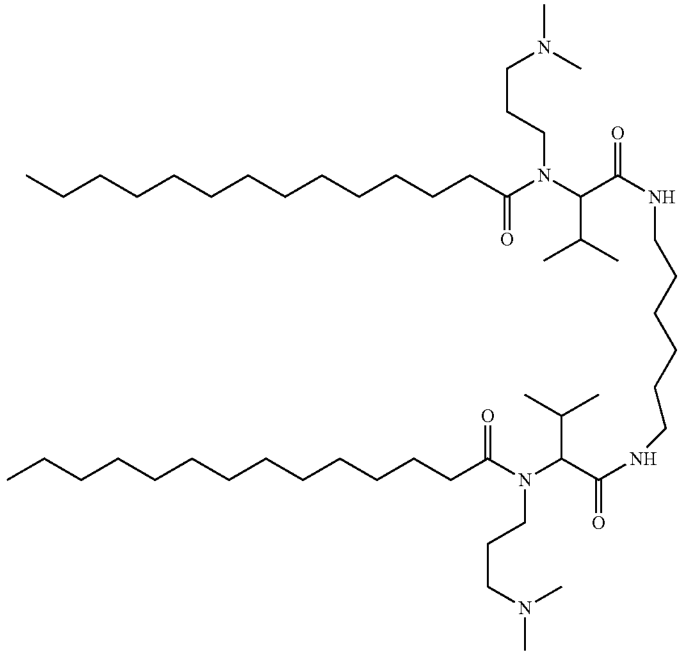 |
| 10 | I1 | R2 | C16 | A1 | I1R2C16A1 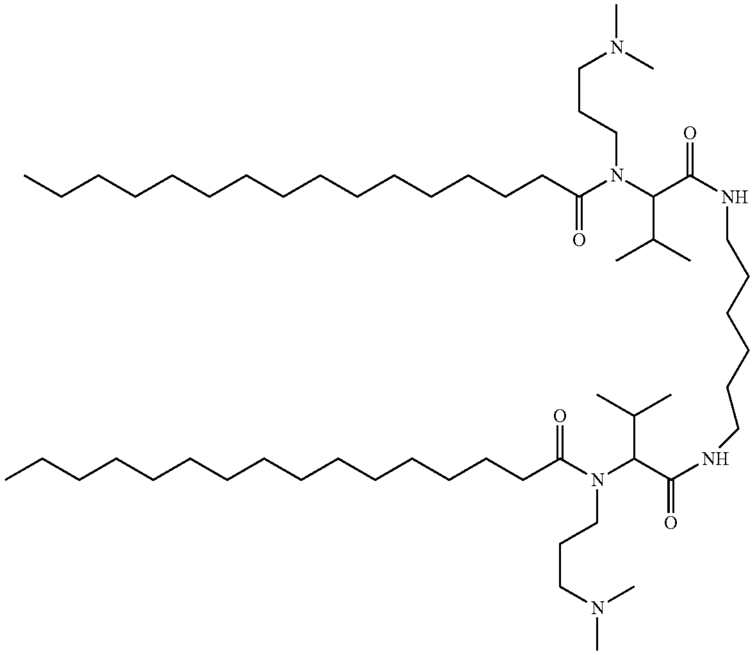 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 11 | I1 | R2 | C18 | A1 | I1R2C18A1 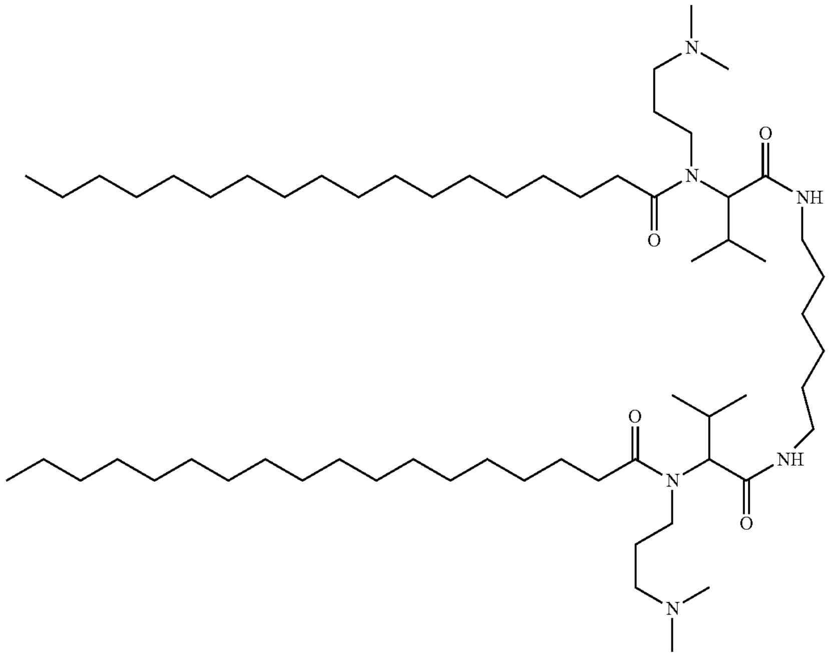 |
| 12 | I1 | R2 | C20 | A1 | I1R2C20A1 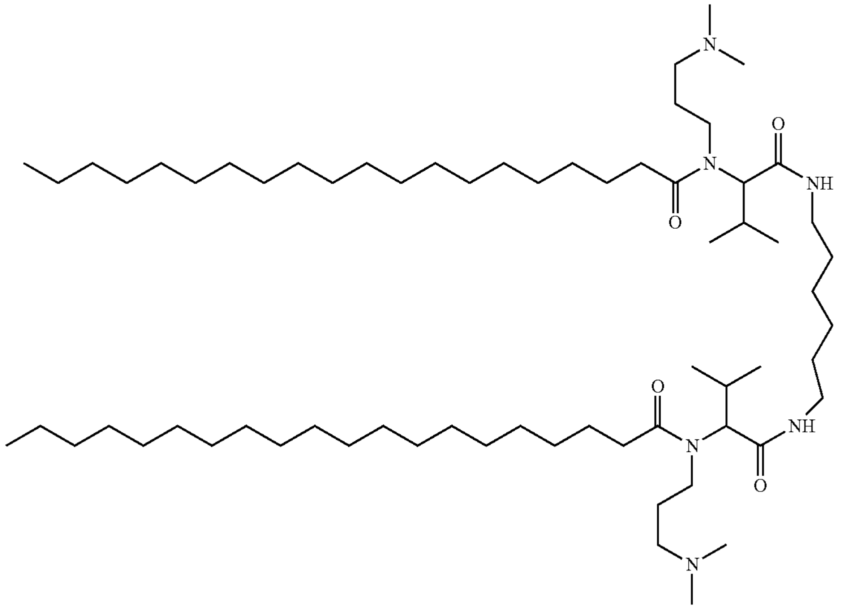 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 13 | I1 | R2 | C18-1 | A1 | I1R2C18-1A1 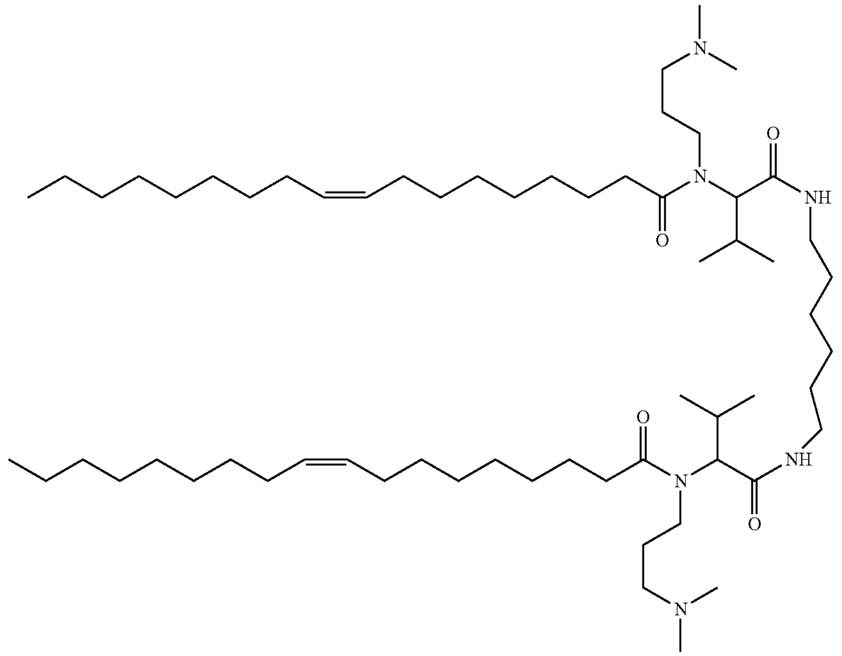 [SMILES: CCCCCCCC/C=C\CCCCCCCC(=O)N(CCCN(C)C)C(C(=O)NCCCCCCNC(=O)C(C(C)C)N(CCCN(C)C)C(=O)CCCCCCC/C=C\CCCCCCCC)C(C)C] |
| 14 | I1 | R2 | C18-2 | A1 | I1R2C18-2A1 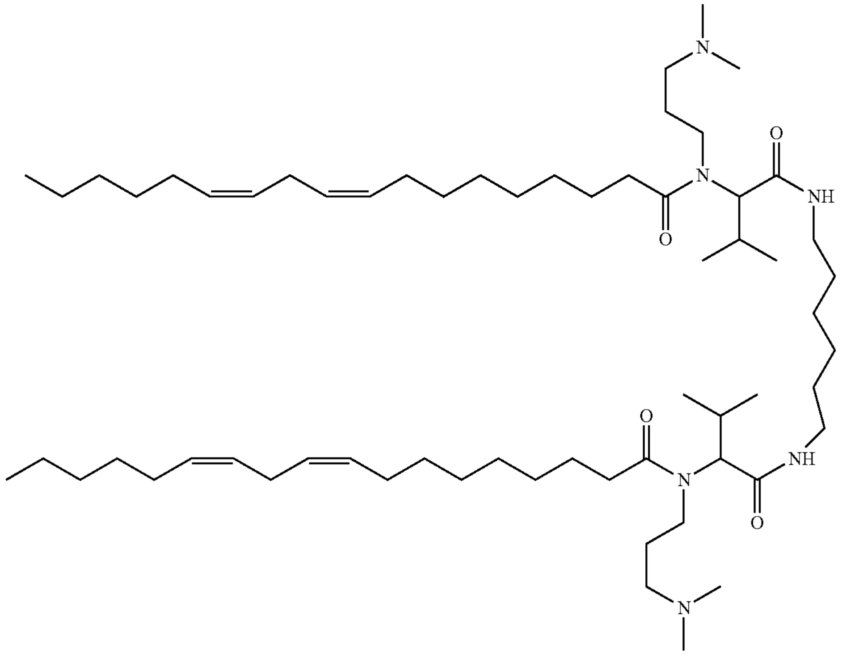 [SMILES: CCCCC/C=C\C/C=C\CCCCCCCC(=O)N(CCCN(C)C)C(C(=O)NCCCCCCNC(=O)C(C(C)C)N(CCCN(C)C)C(=O)CCCCCCC/C=C\C/C=C\CCCCC)C(C)C] |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 15 | I1 | R3 | C12 | A1 | I1R3C12A1 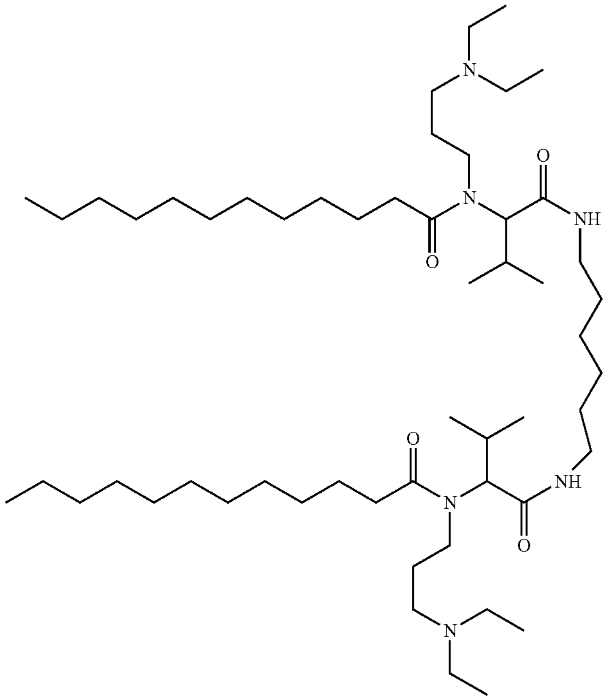 |
| 16 | I1 | R3 | C14 | A1 | I1R3C14A1 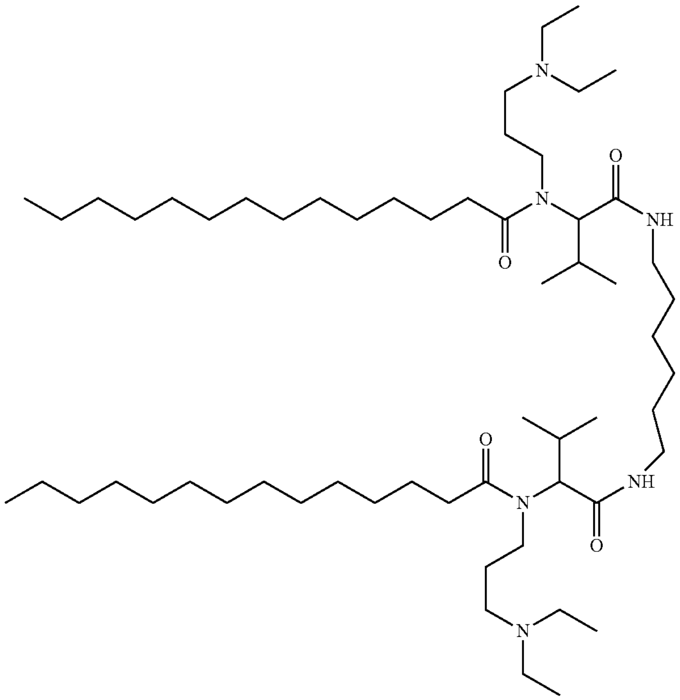 |

TABLE 1-continued
| | Iso-cyanide compound | Amine compound | Carboxylic acid compound | Aldehyde compound | Cationic lipid analog material (number and structural formula) |
|---|---|---|---|---|---|
| 17 | I1 | R3 | C16 | A1 | I1R3C16A1 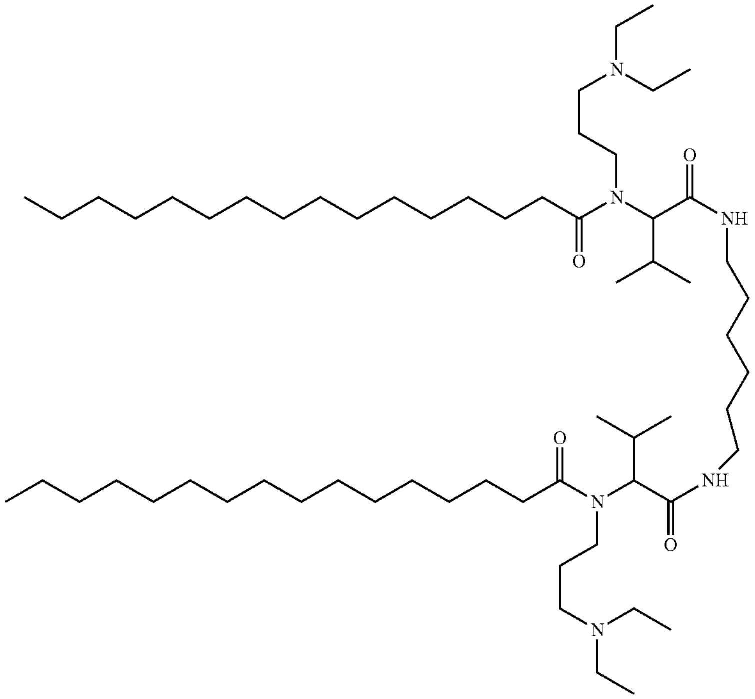 |
| 18 | I1 | R3 | C18 | A1 | I1R3C18A1 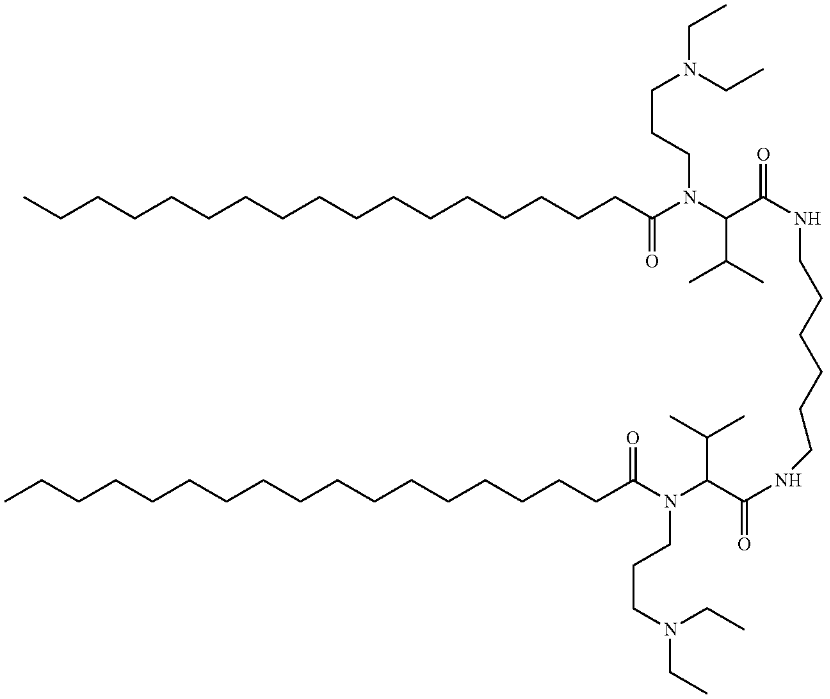 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 19 | I1 | R3 | C20 | A1 | I1R3C20A1 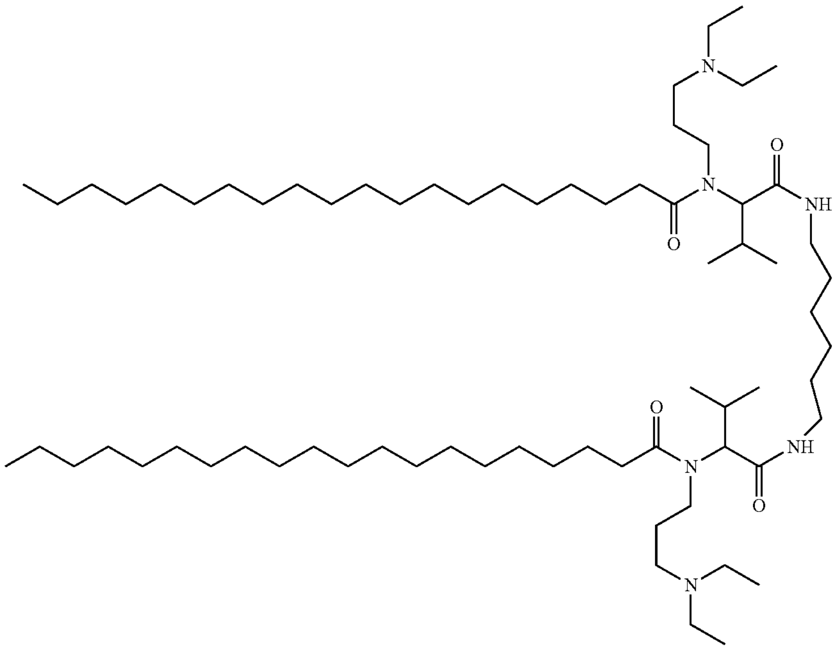 |
| 20 | I1 | R3 | C18-1 | A1 | I1R3C18-1A1 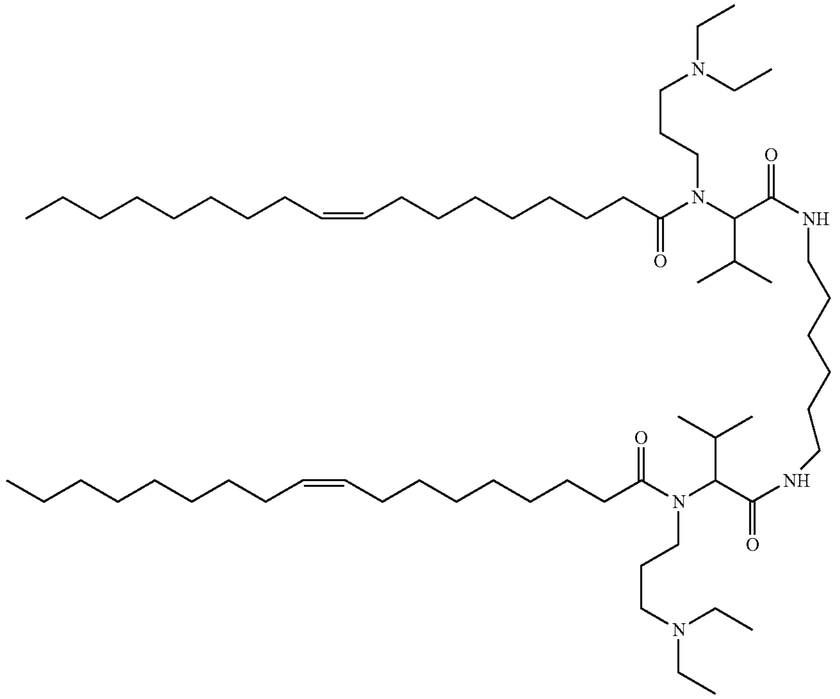 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 21 | I1 | R3 | C18-2 | A1 | I1R3C18-2A1 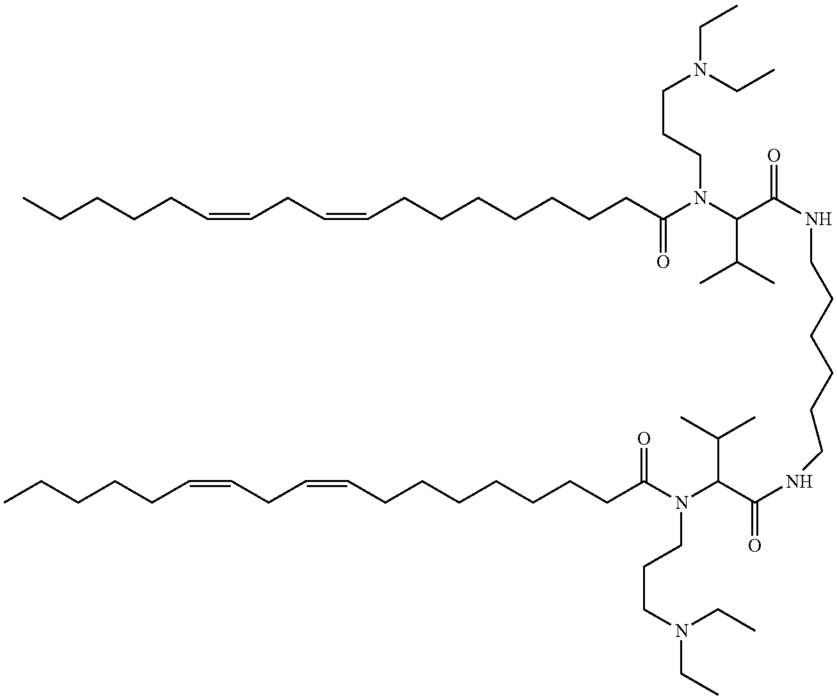 [SMILES: CCCCC/C=C\C/C=C\CCCCCCCC(=O)N(CCCN(CC)CC)C(C(=O)NCCCCCCNC(=O)C(C(C)C)N(CCCN(CC)CC)C(=O)CCCCCCC/C=C\C/C=C\CCCCC)C(C)C] |
| 22 | I1 | R5 | C12 | A1 | I1R5C12A1 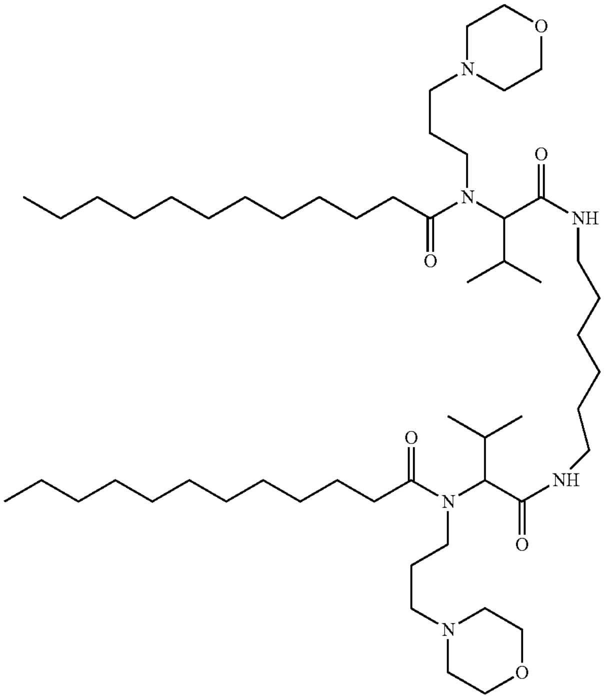 [SMILES: CCCCCCCCCCCC(=O)N(CCCN1CCOCC1)C(C(=O)NCCCCCCNC(=O)C(C(C)C)N(CCCN1CCOCC1)C(=O)CCCCCCCCCCC)C(C)C] |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 23 | I1 | R5 | C14 | A1 | I1R5C14A1 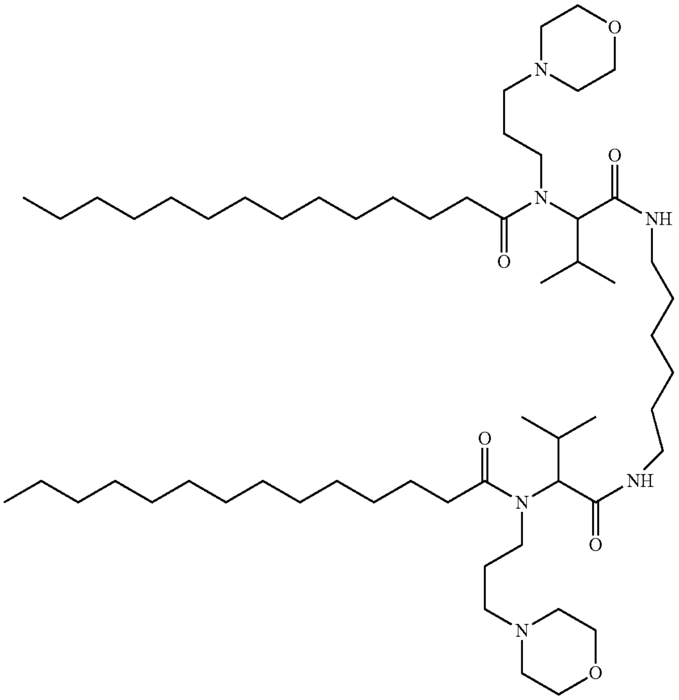 |
| 24 | I1 | R5 | C16 | A1 | I1R5C16A1 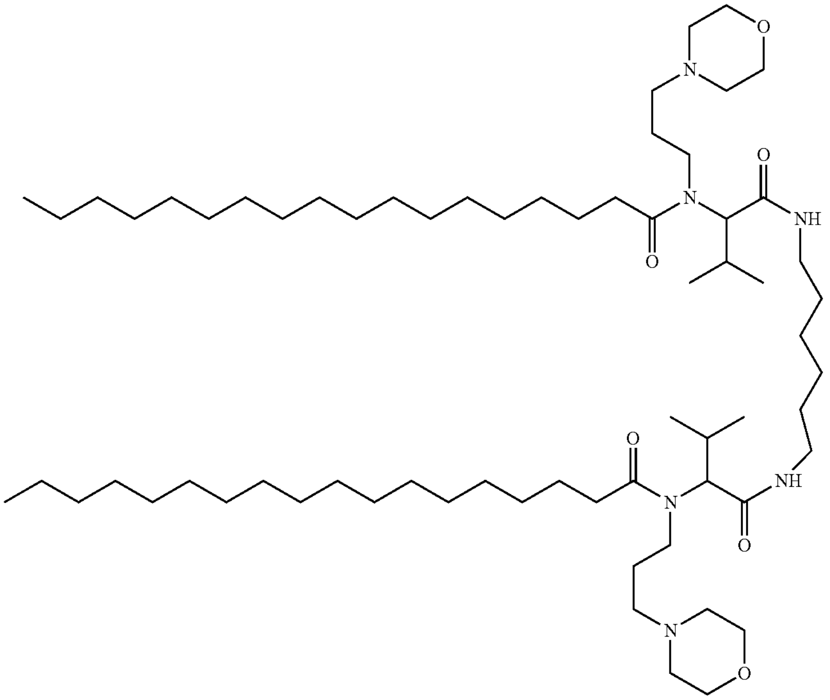 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 25 | I1 | R5 | C18 | A1 | I1R5C18A1 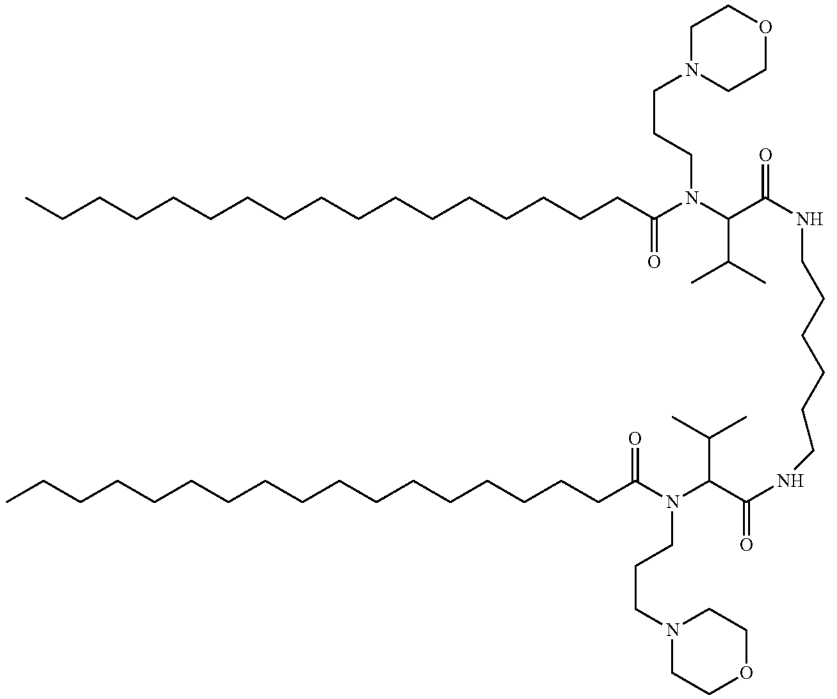 |
| 26 | I1 | R5 | C20 | A1 | I1R5C20A1 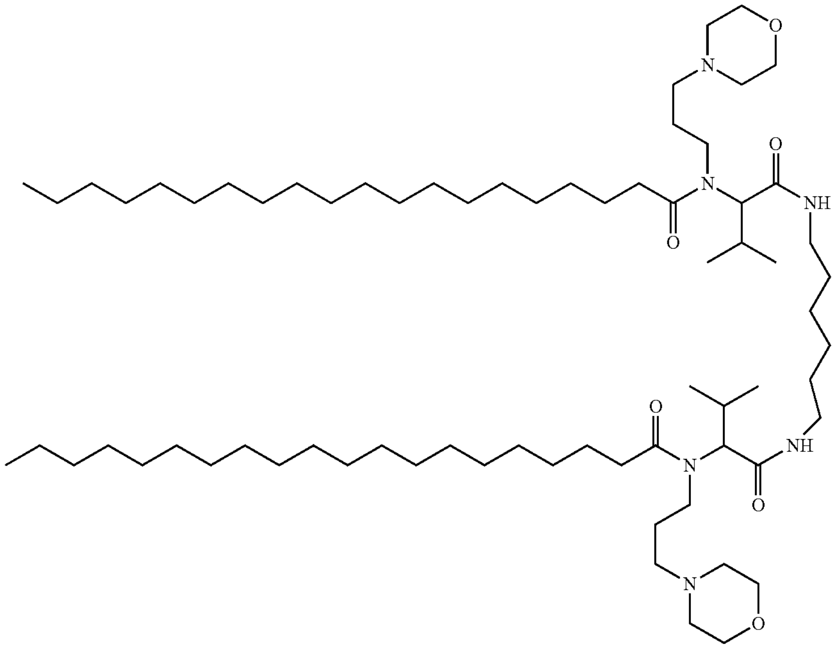 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 27 | I1 | R5 | C18-1 | A1 | I1R5C18-1A1 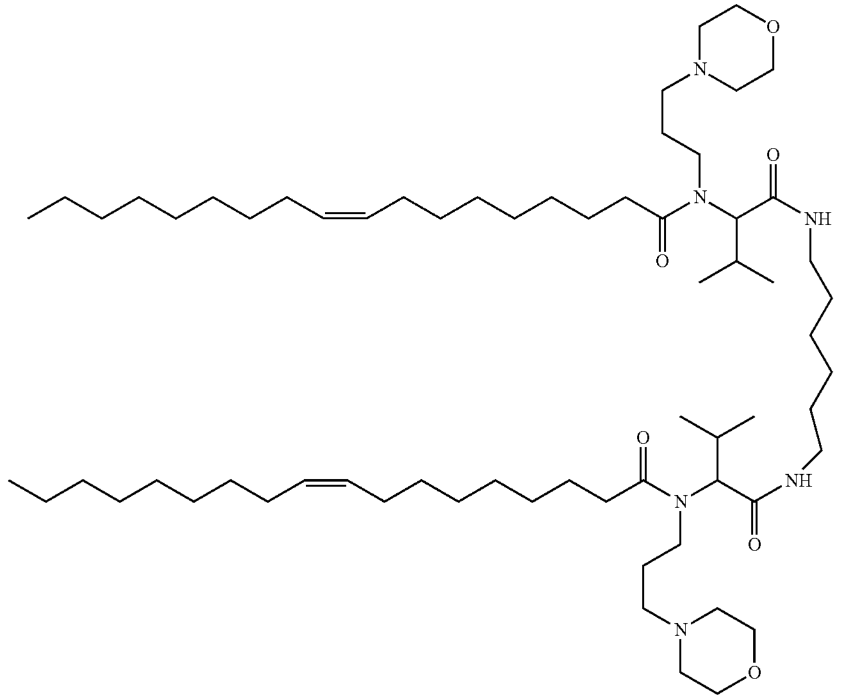 [SMILES: CCCCCCCC/C=C\CCCCCCCC(=O)N(CCCN1CCOCC1)C(C(=O)NCCCCCCNC(=O)C(C(C)C)N(CCCN1CCOCC1)C(=O)CCCCCCC/C=C\CCCCCCCC)C(C)C] |
| 28 | I1 | R5 | C18-2 | A1 | I1R5C18-2A1 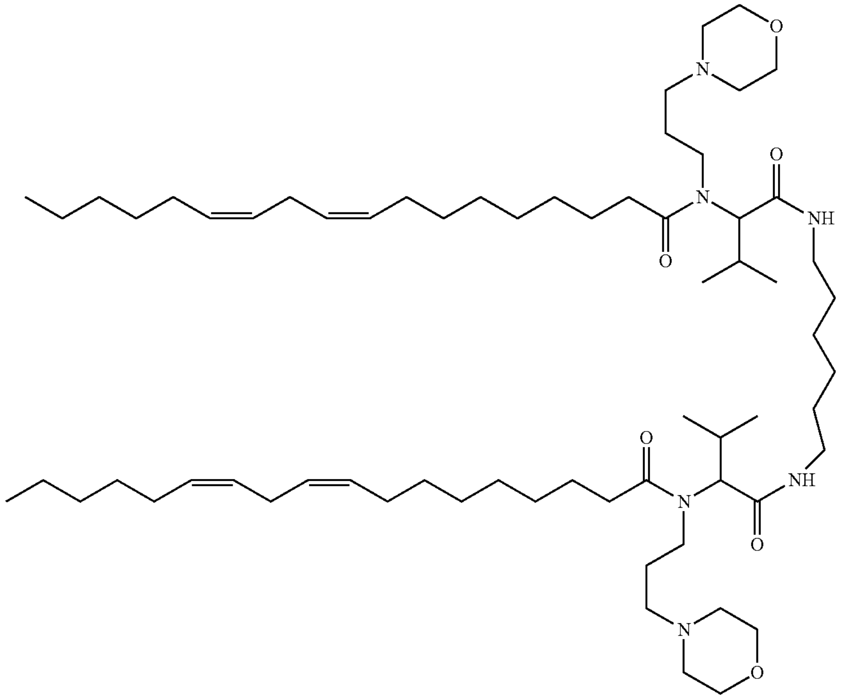 [SMILES: CCCCC/C=C\C/C=C\CCCCCCCC(=O)N(CCCN1CCOCC1)C(C(=O)NCCCCCCNC(=O)C(C(C)C)N(CCCN1CCOCC1)C(=O)CCCCCCC/C=C\C/C=C\CCCCC)C(C)C] |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 29 | I1 | R11 | C12 | A1 | I1R11C12A1 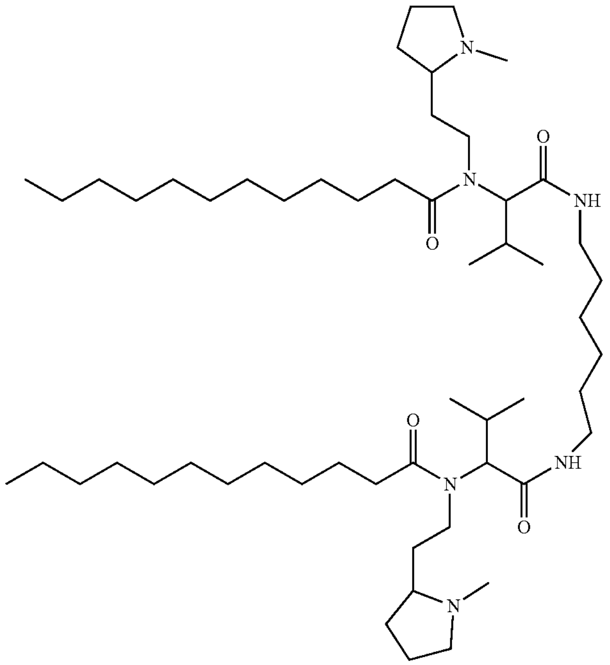 |
| 30 | I1 | R11 | C14 | A1 | I1R11C14A1 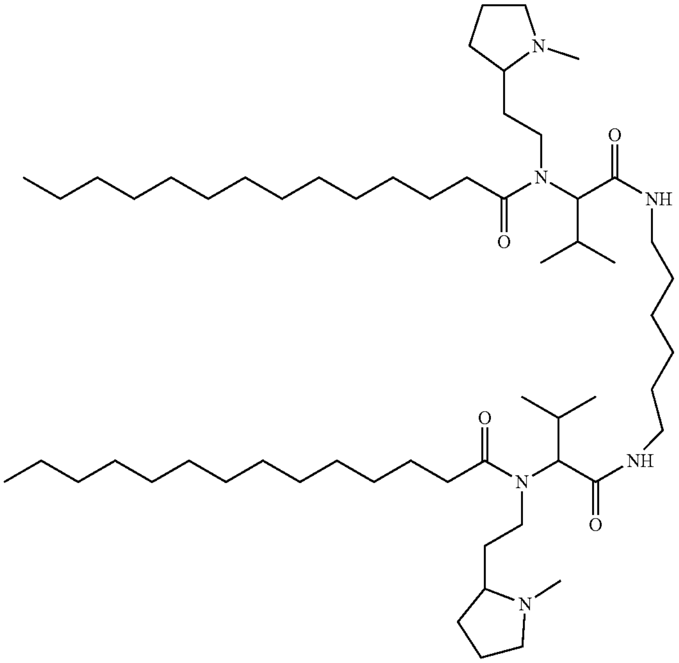 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 31 | I1 | R11 | C16 | A1 | I1R11C16A1 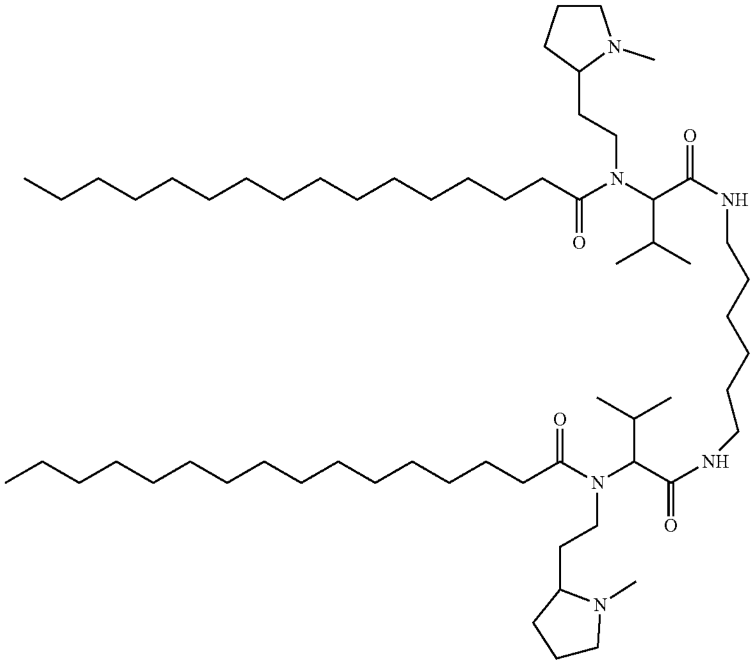 |
| 32 | I1 | R11 | C18 | A1 | I1R11C18A1 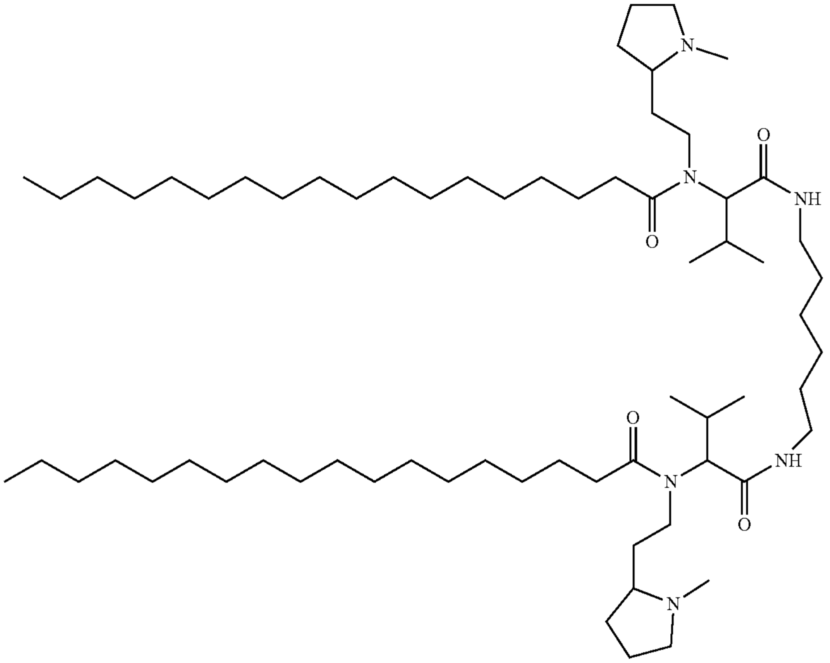 |

TABLE 1-continued
| | Iso-cyanide compound | Amine compound | Carboxylic acid compound | Aldehyde compound | Cationic lipid analog material (number and structural formula) |
|---|---|---|---|---|---|
| 33 | I1 | R11 | C20 | A1 | I1R11C20A1 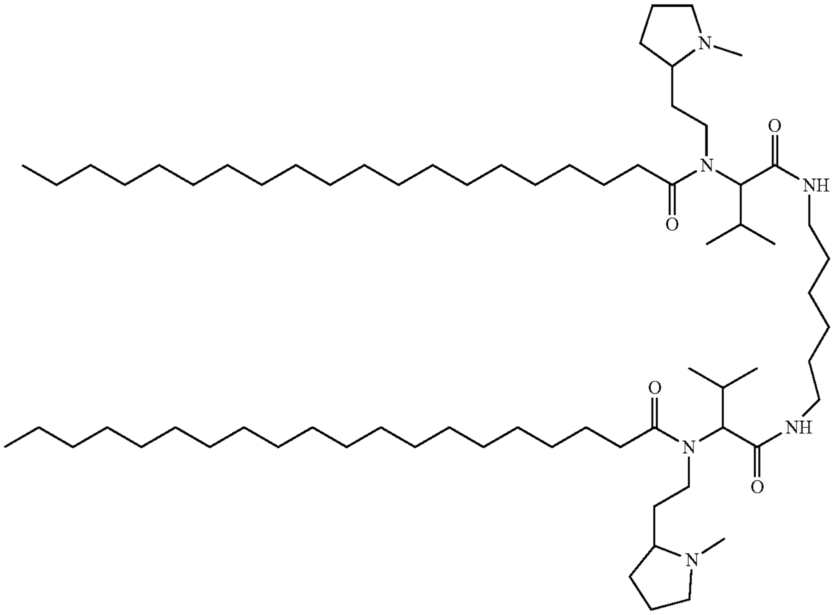 |
| 34 | I1 | R11 | C18-1 | A1 | I1R11C18-1A1 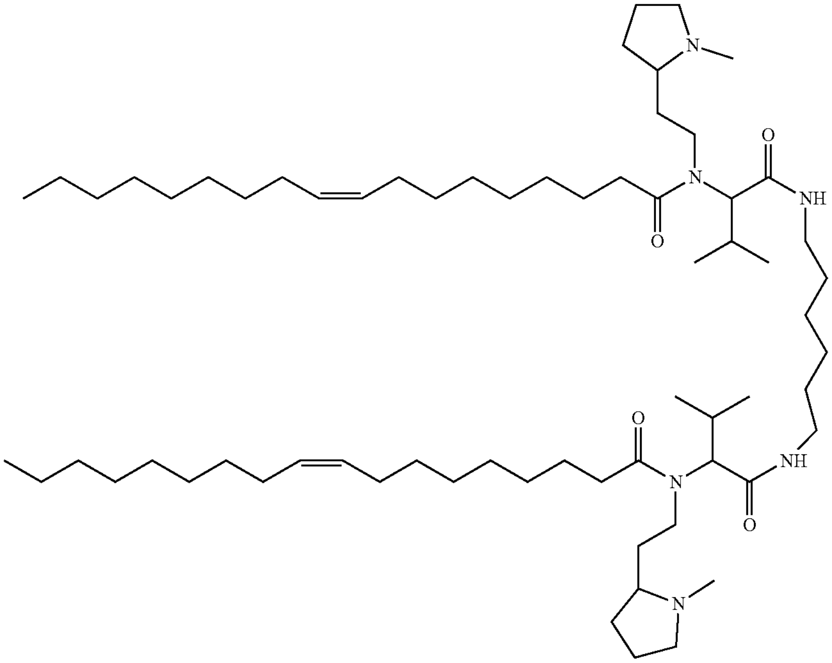 |

TABLE 1-continued
| | Iso-cyanide compound | Amine compound | Carboxylic acid compound | Aldehyde compound | Cationic lipid analog material (number and structural formula) |
|---|---|---|---|---|---|
| 35 | I1 | R11 | C18-2 | A1 | I1R11C18-2A1 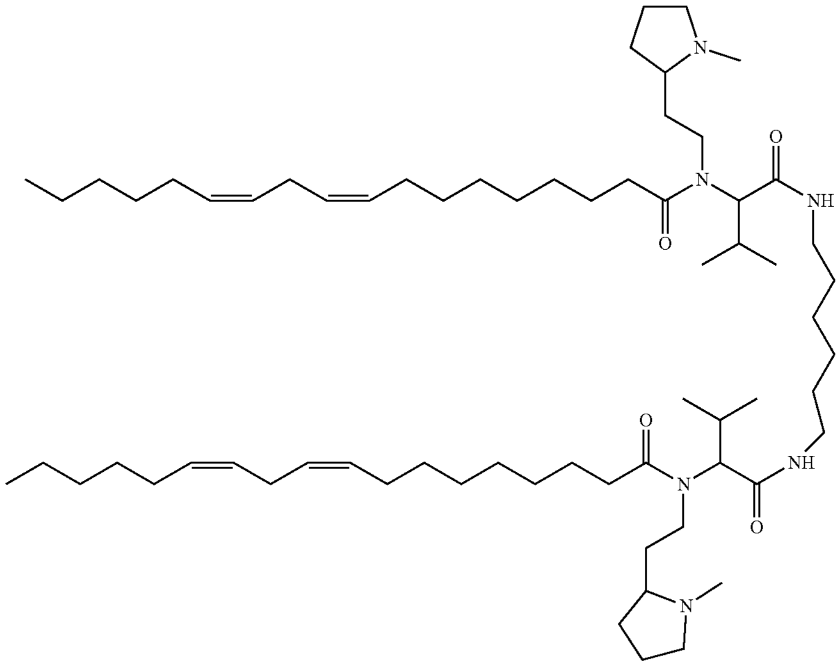 [SMILES: CCCCC/C=C\C/C=C\CCCCCCCC(=O)N(CCC1CCCN1C)C(C(=O)NCCCCCCNC(=O)C(C(C)C)N(CCC1CCCN1C)C(=O)CCCCCCC/C=C\C/C=C\CCCCC)C(C)C] |
| 36 | I2 | R1 | C12 | A1 | I2R1C12A1 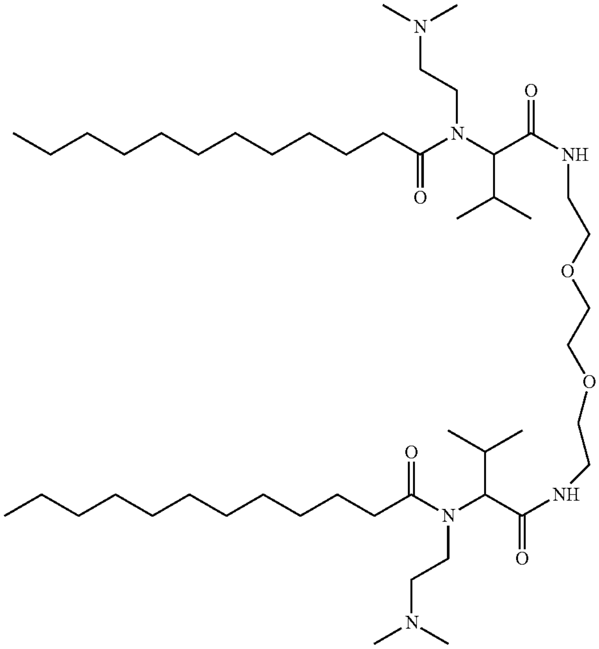 [SMILES: CCCCCCCCCCCC(=O)N(CCN(C)C)C(C(=O)NCCOCCOCCNC(=O)C(C(C)C)N(CCN(C)C)C(=O)CCCCCCCCCCC)C(C)C] |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 37 | I2 | R1 | C14 | A1 | I2R1C14A1 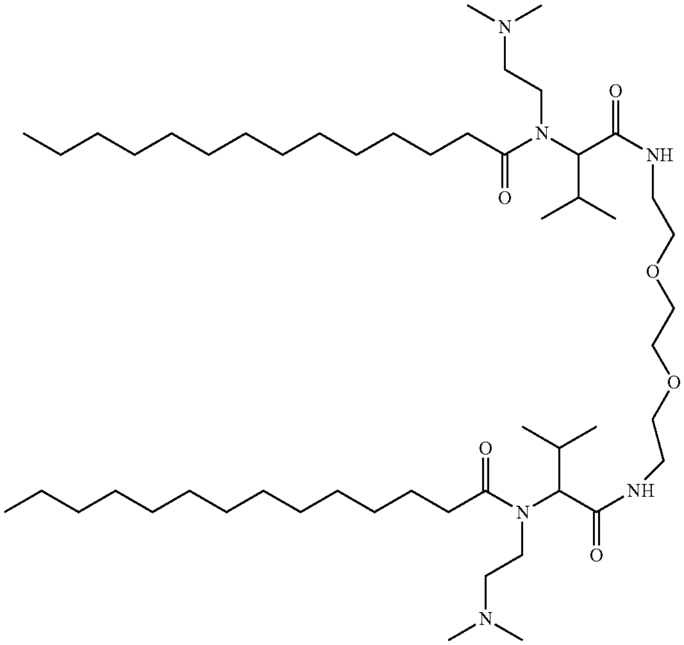 |
| 38 | I2 | R1 | C16 | A1 | I2R1C16A1 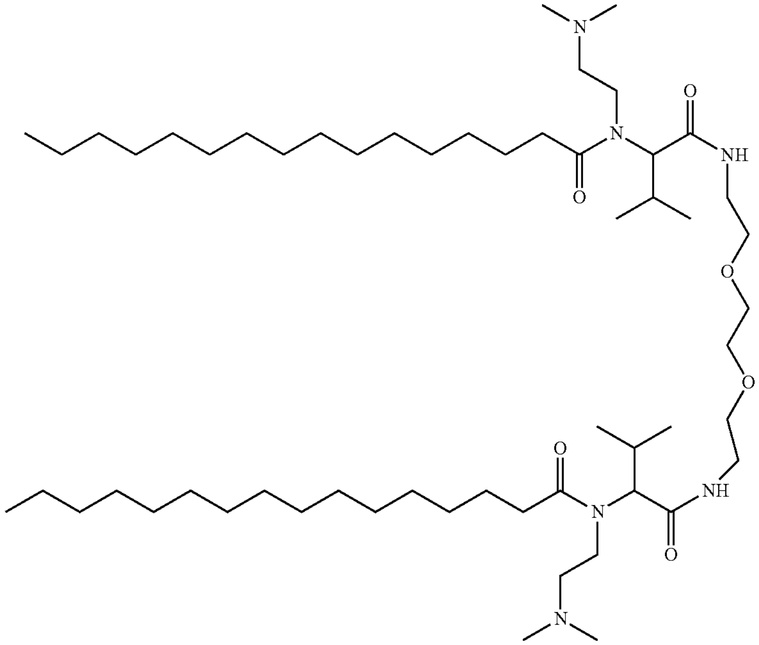 |

TABLE 1-continued
| | Iso-cyanide compound | Amine compound | Carboxylic acid compound | Aldehyde compound | Cationic lipid analog material (number and structural formula) |
|---|---|---|---|---|---|
| 39 | I2 | R1 | C18 | A1 | I2R1C18A1 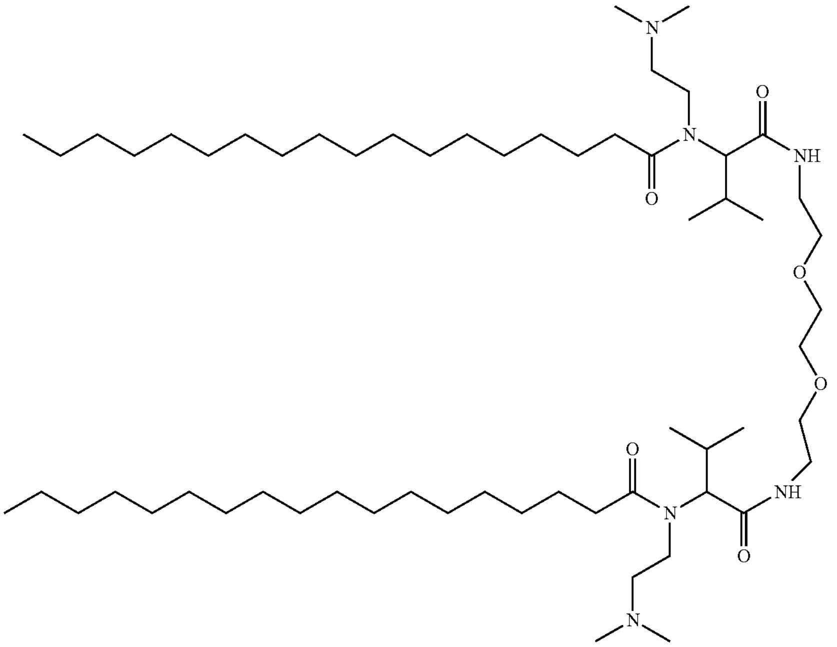 |
| 40 | I2 | R1 | C20 | A1 | I2R1C20A1 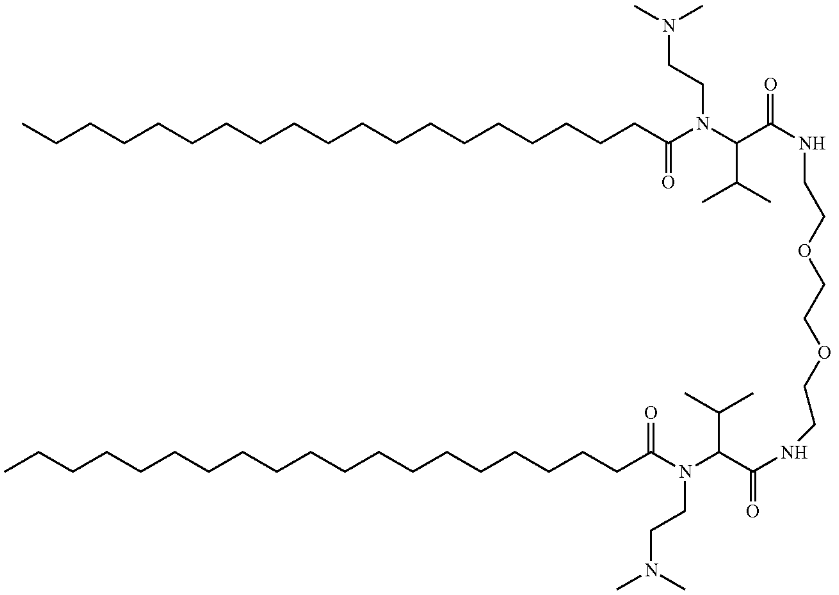 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 41 | I2 | R1 | C18-1 | A1 | I2R1C18-1A1 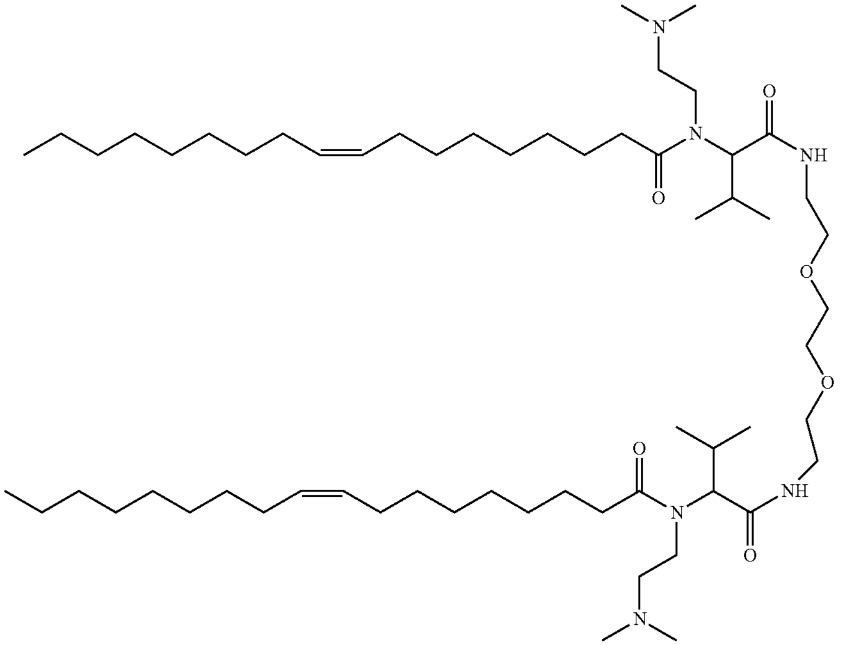 [SMILES: CCCCCCCC/C=C\CCCCCCCC(=O)N(CCN(C)C)C(C(=O)NCCOCCOCCNC(=O)C(C(C)C)N(CCN(C)C)C(=O)CCCCCCC/C=C\CCCCCCCC)C(C)C] |
| 42 | I2 | R1 | C18-2 | A1 | I2R1C18-2A1 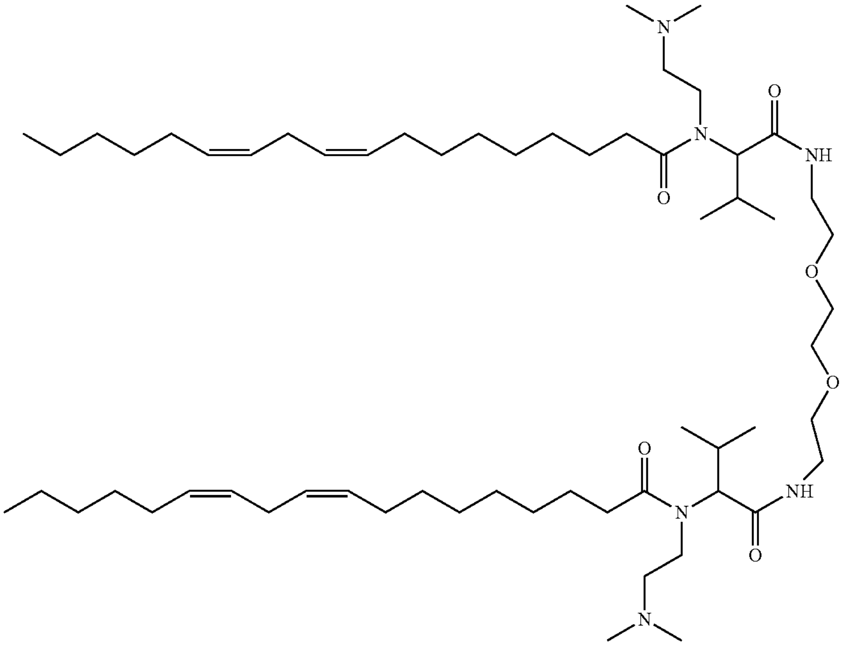 [SMILES: CCCCC/C=C\C/C=C\CCCCCCCC(=O)N(CCN(C)C)C(C(=O)NCCOCCOCCNC(=O)C(C(C)C)N(CCN(C)C)C(=O)CCCCCCC/C=C\C/C=C\CCCCC)C(C)C] |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 43 | I2 | R2 | C12 | A1 | I2R2C12A1 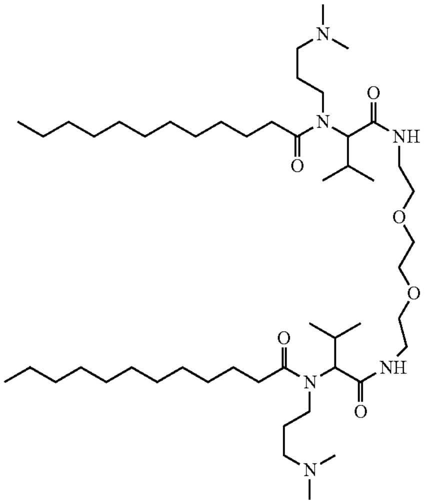 |
| 44 | I2 | R2 | C14 | A1 | I2R2C14A1 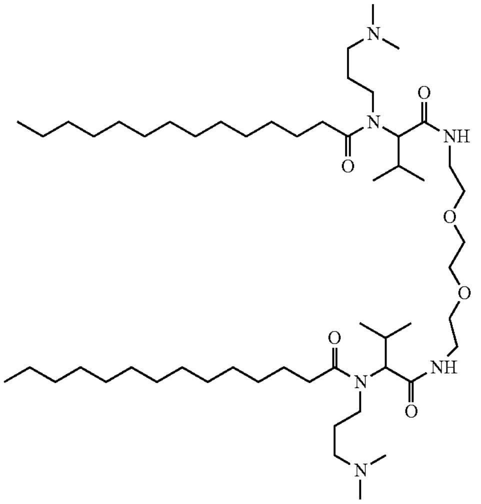 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 45 | I2 | R2 | C16 | A1 | I2R2C16A1 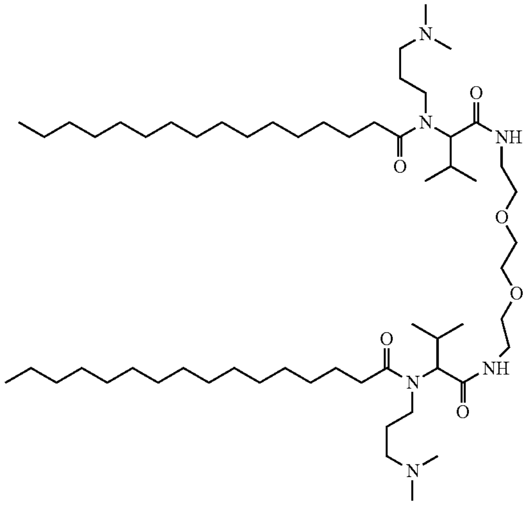 |
| 46 | I2 | R2 | C18 | A1 | I2R2C18A1 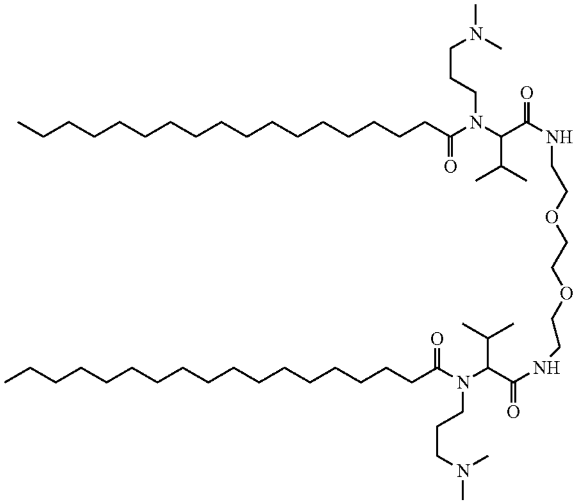 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 47 | I2 | R2 | C20 | A1 | I2R2C20A1 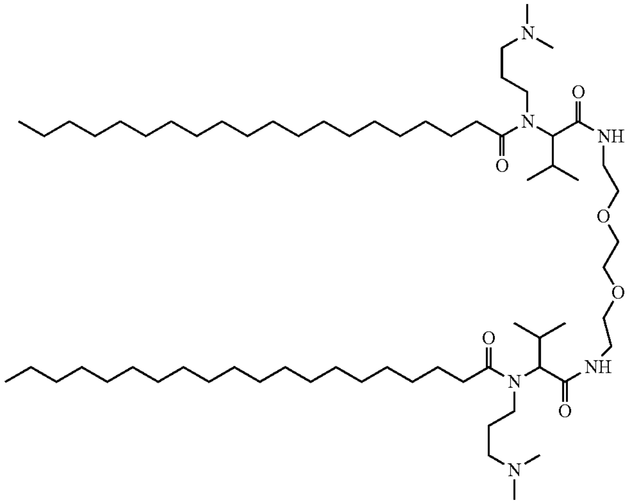 |
| 48 | I2 | R2 | C18-1 | A1 | I2R2C18-IAI 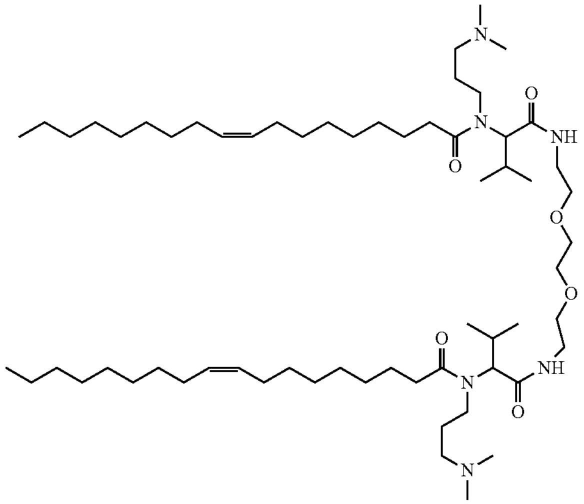 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 49 | I2 | R2 | C18-2 | A1 | I2R2C18-2A1 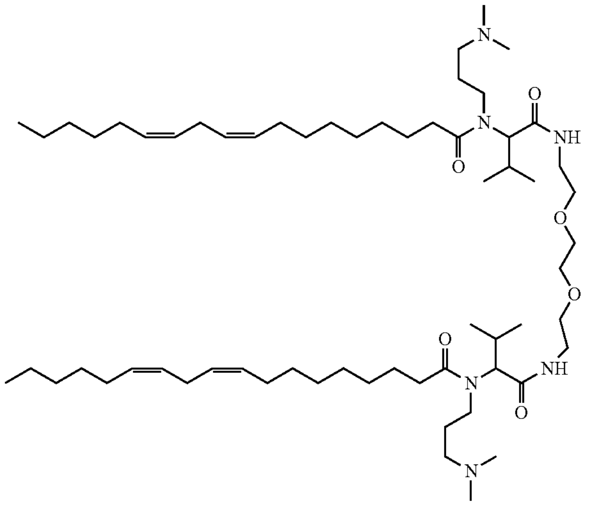 [SMILES: CCCCC/C=C\C/C=C\CCCCCCCC(=O)N(CCCN(C)C)C(C(=O)NCCOCCOCCNC(=O)C(C(C)C)N(CCCN(C)C)C(=O)CCCCCCC/C=C\C/C=C\CCCCC)C(C)C] |
| 50 | I2 | R3 | C12 | A1 | I2R3C12A1 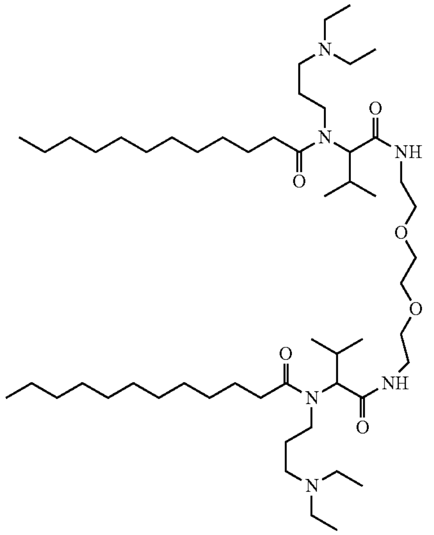 [SMILES: CCCCCCCCCCCC(=O)N(CCCN(CC)CC)C(C(=O)NCCOCCOCCNC(=O)C(C(C)C)N(CCCN(CC)CC)C(=O)CCCCCCCCCCC)C(C)C] |

TABLE 1-continued
| | Iso-cyanide compound | Amine compound | Carboxylic acid compound | Aldehyde compound | Cationic lipid analog material (number and structural formula) |
|---|---|---|---|---|---|
| 51 | I2 | R3 | C14 | A1 | I2R3C14A1 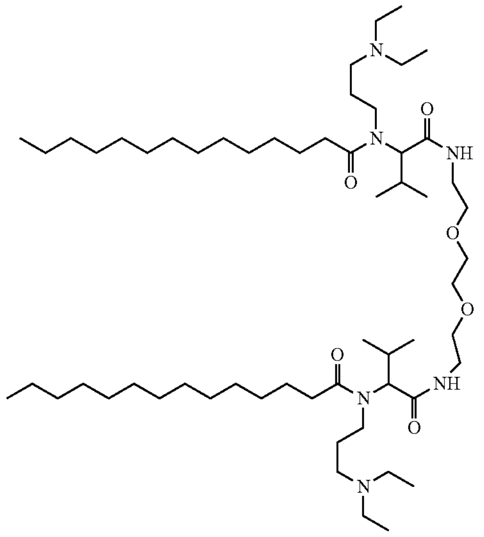 |
| 52 | I2 | R3 | C16 | A1 | I2R3C16A1 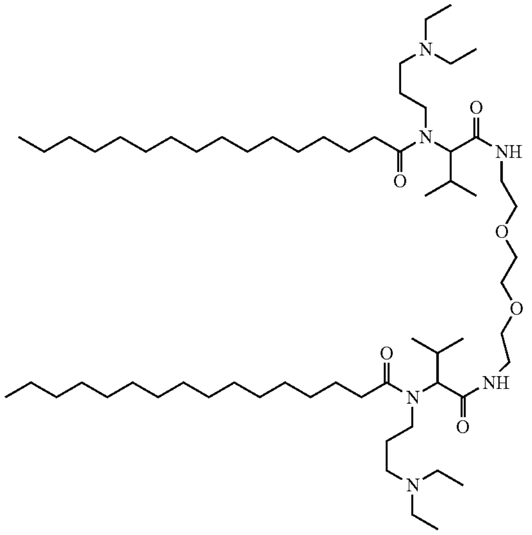 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 53 | I2 | R3 | C18 | A1 | I2R3C18A1 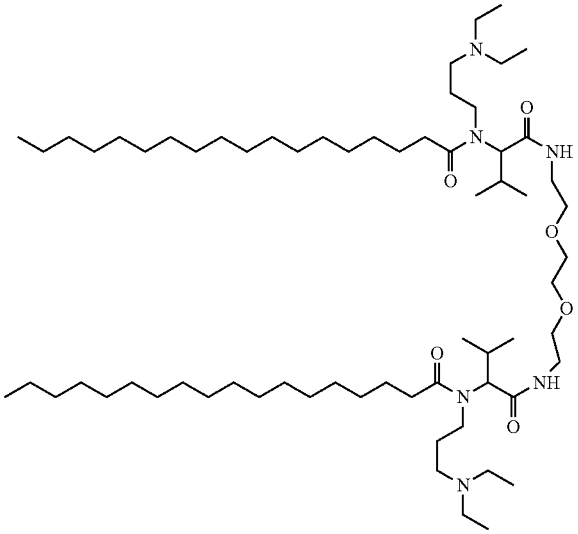 |
| 54 | I2 | R3 | C20 | A1 | I2R3C20A1 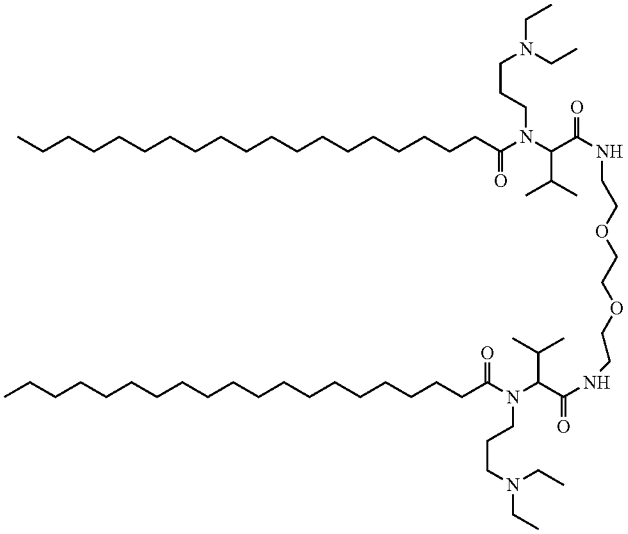 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 55 | I2 | R3 | C18-1 | A1 | I2R3C18-1A1 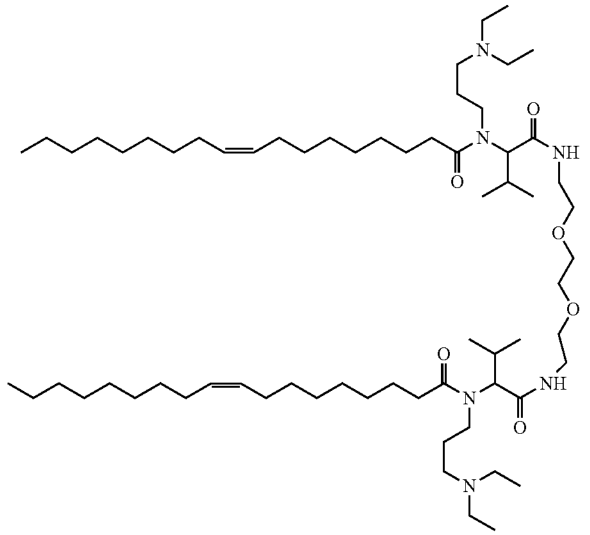 [SMILES: CCCCCCCC/C=C\CCCCCCCC(=O)N(CCCN(CC)CC)C(C(=O)NCCOCCOCCNC(=O)C(C(C)C)N(CCCN(CC)CC)C(=O)CCCCCCC/C=C\CCCCCCCC)C(C)C] |
| 56 | I2 | R3 | C18-2 | A1 | I2R3C18-2A1 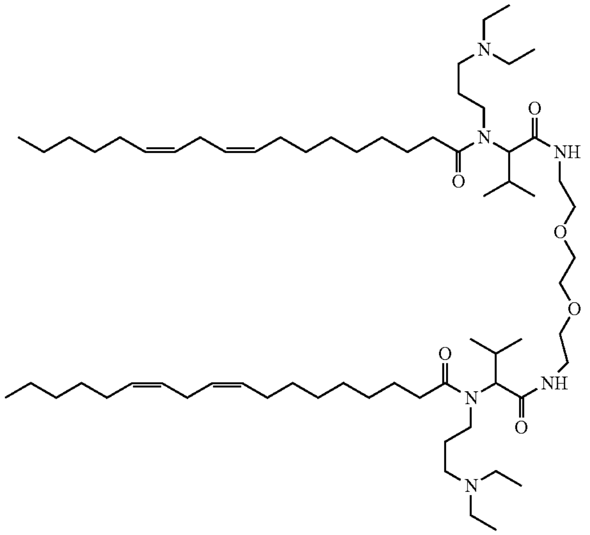 [SMILES: CCCCC/C=C\C/C=C\CCCCCCCC(=O)N(CCCN(CC)CC)C(C(=O)NCCOCCOCCNC(=O)C(C(C)C)N(CCCN(CC)CC)C(=O)CCCCCCC/C=C\C/C=C\CCCCC)C(C)C] |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 57 | I2 | R5 | C12 | A1 | I2R5C12A1 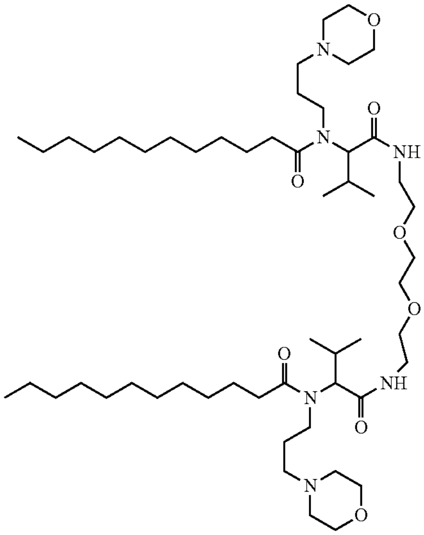 |
| 58 | I2 | R5 | C14 | A1 | I2R5C14A1 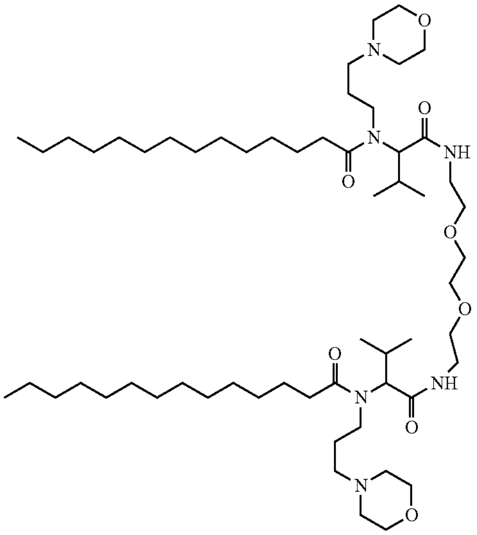 |

TABLE 1-continued
| | Iso-cyanide compound | Amine compound | Carboxylic acid compound | Aldehyde compound | Cationic lipid analog material (number and structural formula) |
|---|---|---|---|---|---|
| 59 | I2 | R5 | C16 | A1 | I2R5C16A1 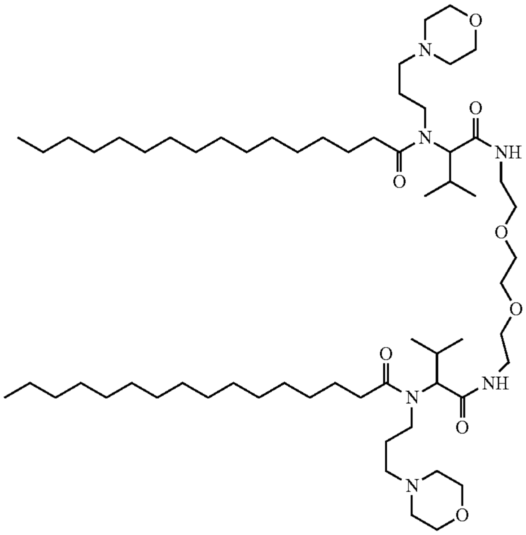 |
| 60 | I2 | R5 | C18 | A1 | I2R5C18A1 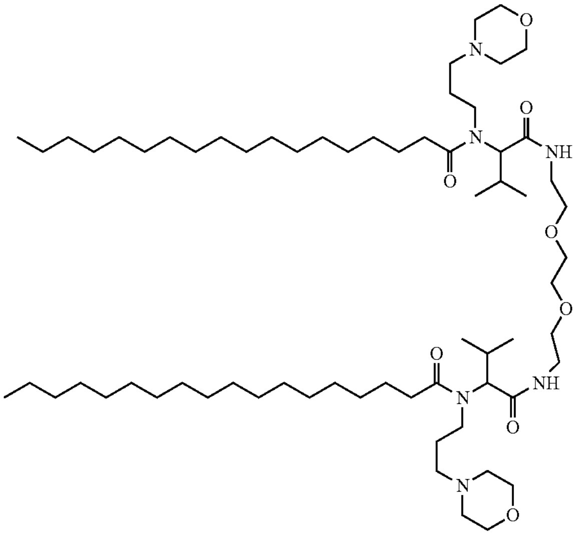 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 61 | I2 | R5 | C20 | A1 | I2R5C20A1 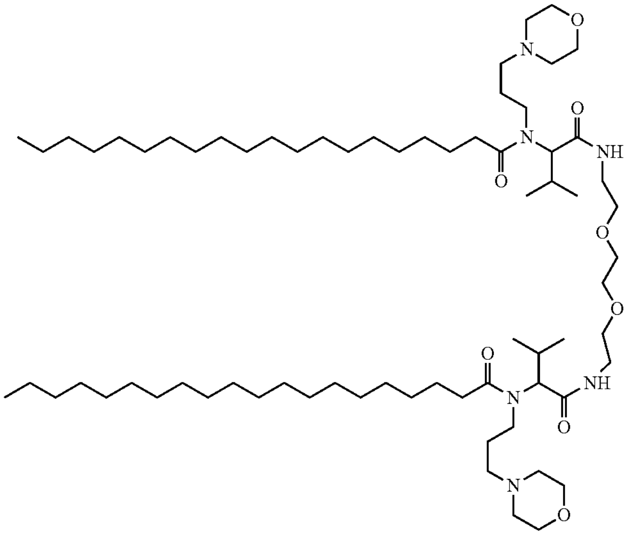 |
| 62 | I2 | R5 | C18-1 | A1 | I2R5C18-1A1 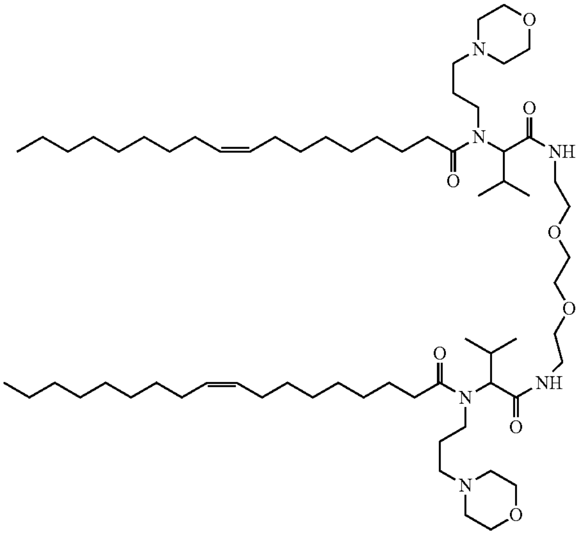 |

TABLE 1-continued
| | Iso-cyanide compound | Amine compound | Carboxylic acid compound | Aldehyde compound | Cationic lipid analog material (number and structural formula) |
|---|---|---|---|---|---|
| 63 | I2 | R5 | C18-2 | A1 | I2R5C18-2A1 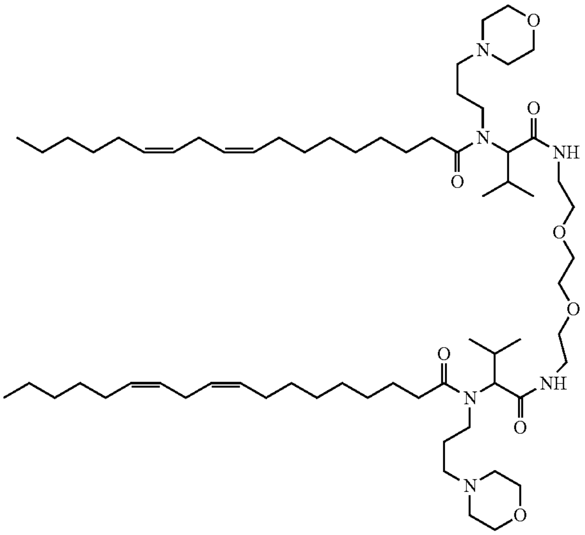 [SMILES: CCCCC/C=C\C/C=C\CCCCCCCC(=O)N(CCCN1CCOCC1)C(C(=O)NCCOCCOCCNC(=O)C(C(C)C)N(CCCN1CCOCC1)C(=O)CCCCCCC/C=C\C/C=C\CCCCC)C(C)C] |
| 64 | I2 | R11 | C12 | A1 | I2R11C12A1 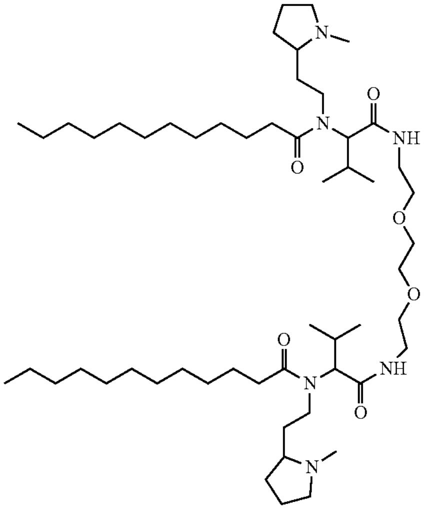 [SMILES: CCCCCCCCCCCC(=O)N(CCC1CCCN1C)C(C(=O)NCCOCCOCCNC(=O)C(C(C)C)N(CCC1CCCN1C)C(=O)CCCCCCCCCCC)C(C)C] |

TABLE 1-continued
| | Iso-cyanide compound | Amine compound | Carboxylic acid compound | Aldehyde compound | Cationic lipid analog material (number and structural formula) |
|---|---|---|---|---|---|
| 65 | I2 | R11 | C14 | A1 | I2R11C14A1 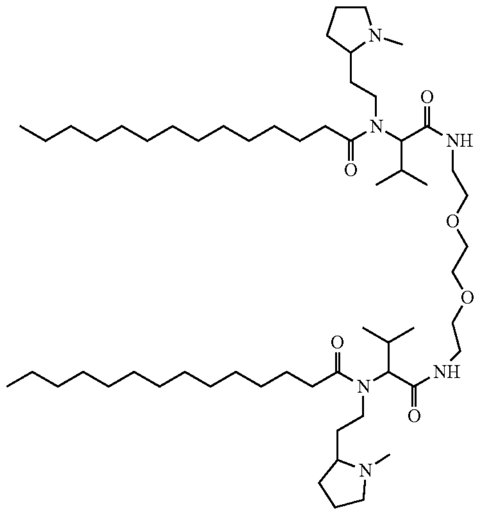 |
| 66 | I2 | R11 | C16 | A1 | I2R11C16A1 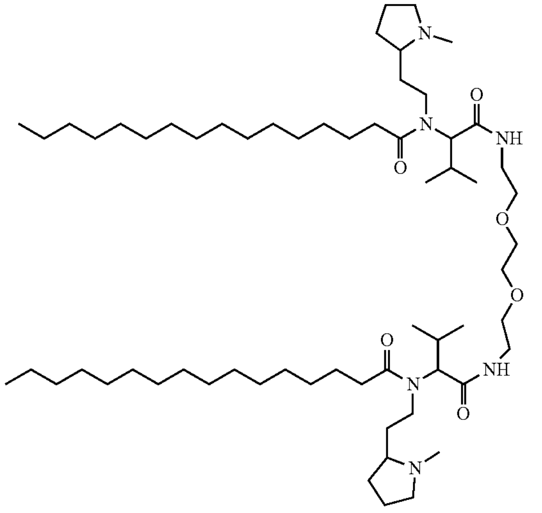 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 67 | I2 | R11 | C18 | A1 | I2R11C18A1 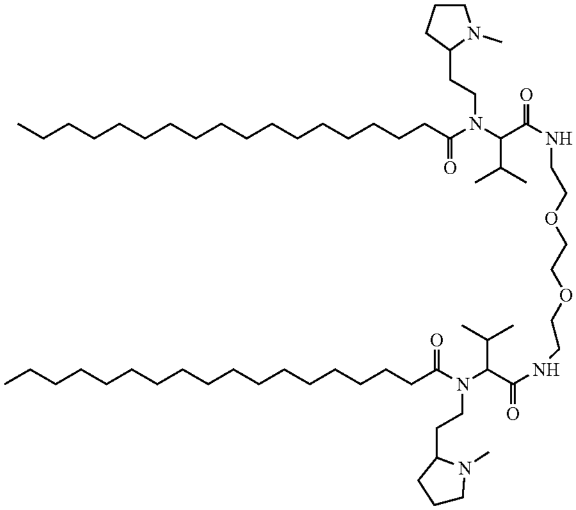 |
| 68 | I2 | R11 | C20 | A1 | I2R11C20A1 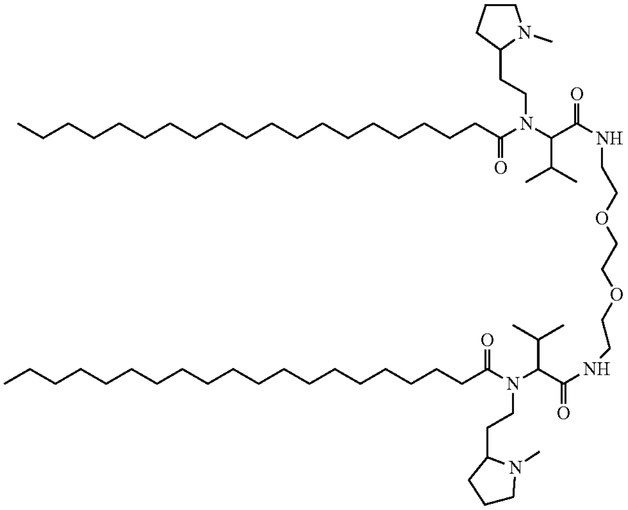 |

TABLE 1-continued
| | Iso-cyanide compound | Amine compound | Carb-oxylic acid compound | Alde-hyde compound | Cationic lipid analog material (number and structural formula) |
|---|---|---|---|---|---|
| 69 | I2 | R11 | C18-1 | A1 | I2R11C18-1A1 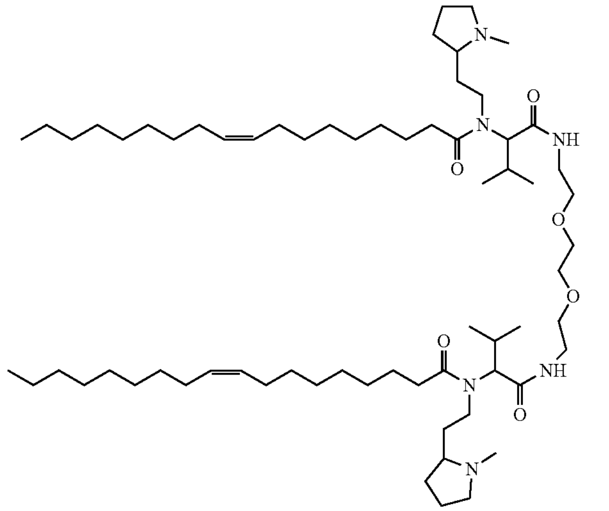 [SMILES: CCCCCCCC/C=C\CCCCCCCC(=O)N(CCC1CCCN1C)C(C(=O)NCCOCCOCCNC(=O)C(C(C)C)N(CCC1CCCN1C)C(=O)CCCCCCC/C=C\CCCCCCCC)C(C)C] |
| 70 | I2 | R11 | C18-2 | A1 | I2R11C18-2A1 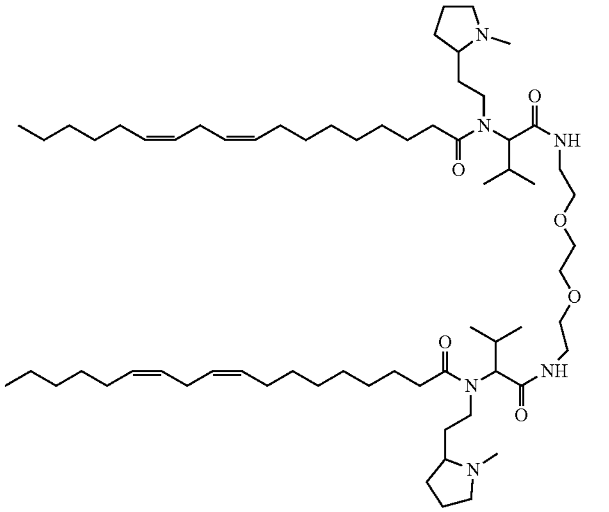 [SMILES: CCCCC/C=C\C/C=C\CCCCCCCC(=O)N(CCC1CCCN1C)C(C(=O)NCCOCCOCCNC(=O)C(C(C)C)N(CCC1CCCN1C)C(=O)CCCCCCC/C=C\C/C=C\CCCCC)C(C)C] |
| 71 | I2-1 | R2 | C18 | A1 | I2-IR2C18A1 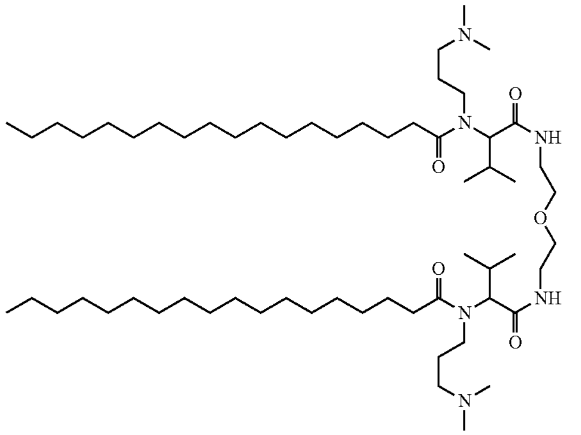 [SMILES: CCCCCCCCCCCCCCCCCC(=O)N(CCCN(C)C)C(C(=O)NCCOCCNC(=O)C(C(C)C)N(CCCN(C)C)C(=O)CCCCCCCCCCCCCCCCC)C(C)C] |

TABLE 1-continued

| | Iso-cyanide compound | Amine compound | Carb-oxylic acid compound | Alde-hyde compound | Cationic lipid analog material (number and structural formula) |
|---|---|---|---|---|---|
| 72 | I2-3 | R2 | C18 | A1 | I2-3R2C18A1 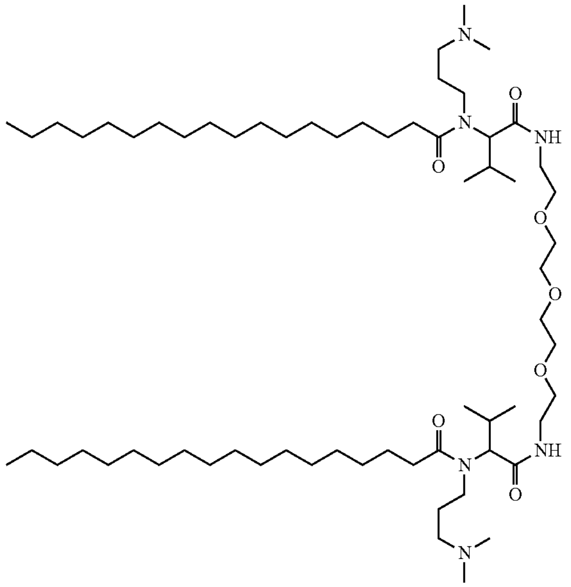 [SMILES: CCCCCCCCCCCCCCCCCC(=O)N(CCCN(C)C)C(C(=O)NCCOCCOCCOCCNC(=O)C(C(C)C)N(CCCN(C)C)C(=O)CCCCCCCCCCCCCCCCC)C(C)C] |

Figure 1B:
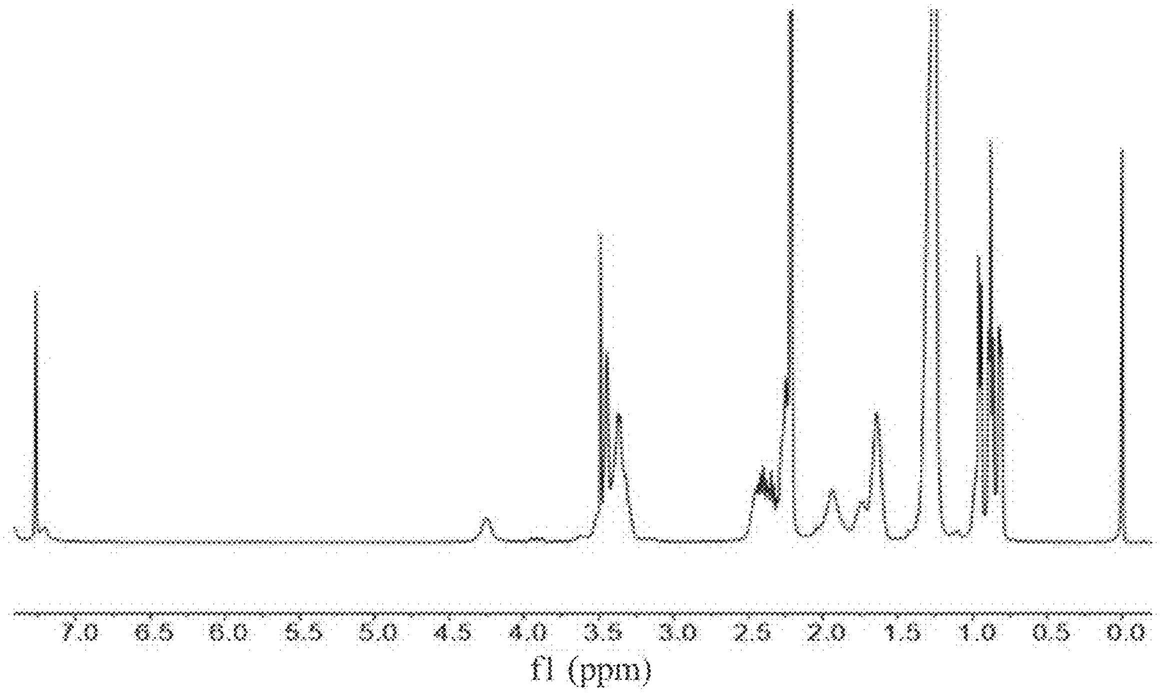
FIG. 1B shows a proton nuclear magnetic resonance spectrum of cationic lipid analog material I2-1R2C18A1.
Figure 2A:
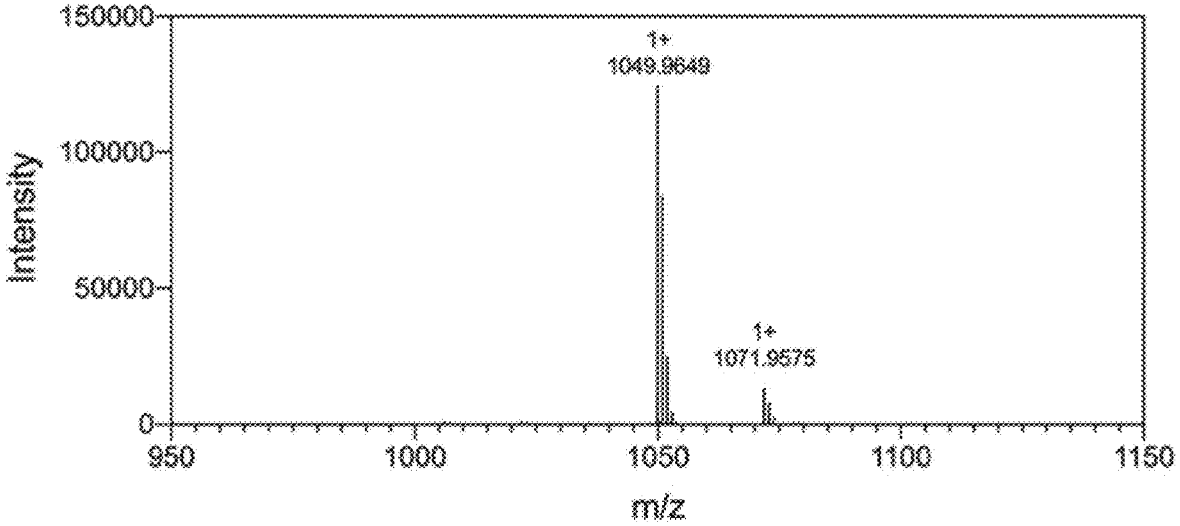
FIG. 2A shows a mass spectrometry spectrum of cationic lipid analog material I2R2C18A1.
Figure 2B:
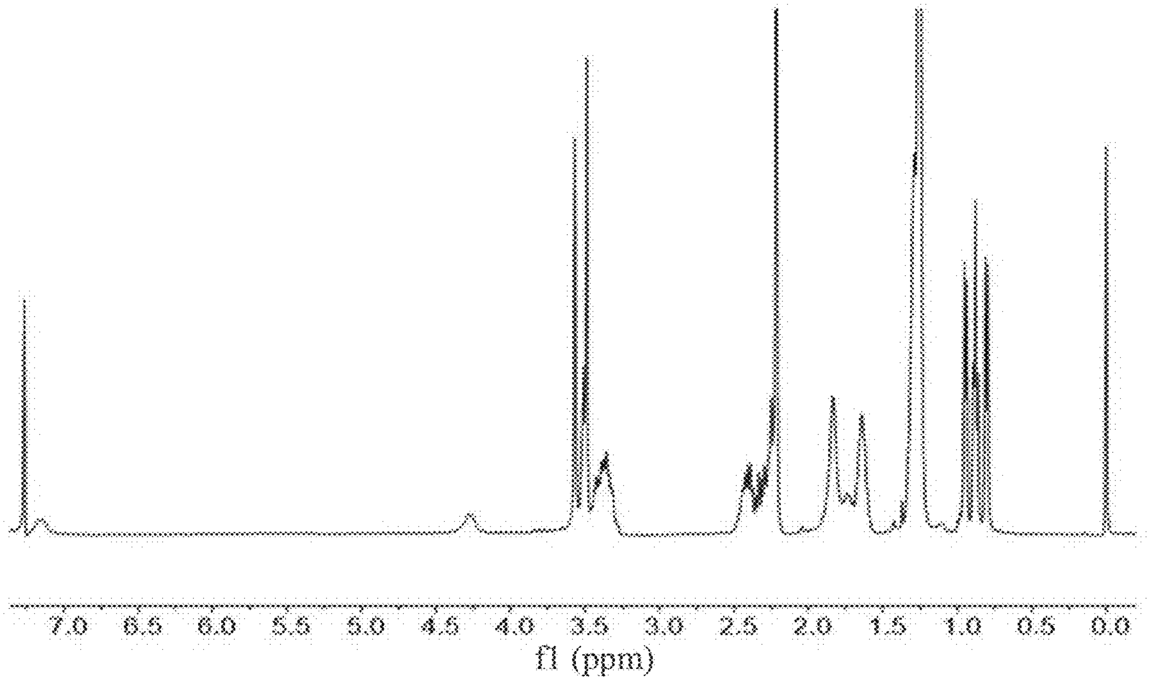
FIG. 2B shows a proton nuclear magnetic resonance spectrum of cationic lipid analog material I2R2C18A1.
Figure 3A:
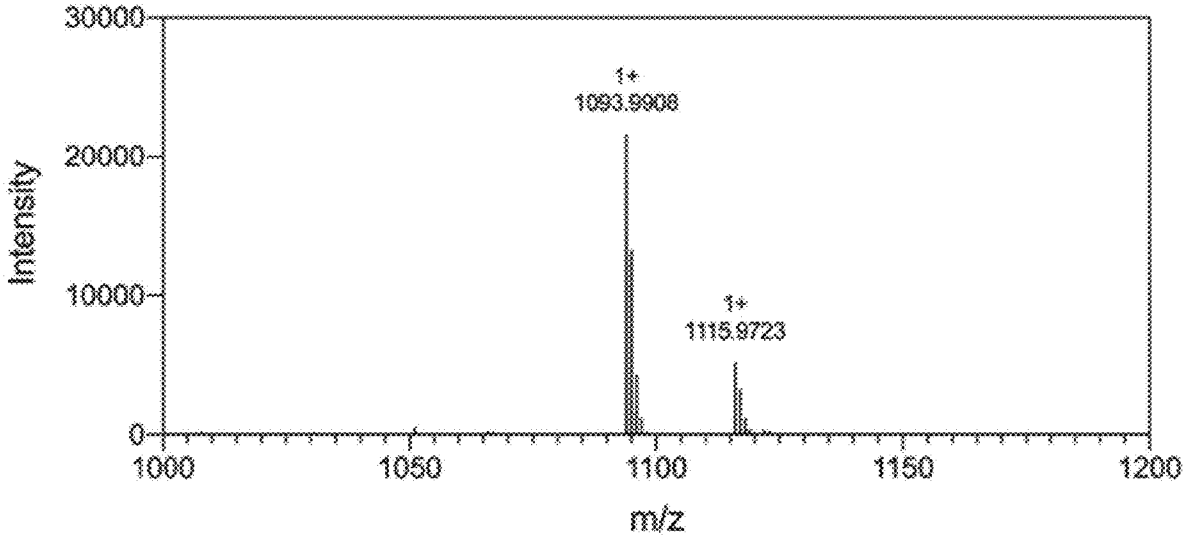
FIG. 3A shows a mass spectrometry spectrum of cationic lipid analog material I2-3R2C18A1.
Figure 3B:
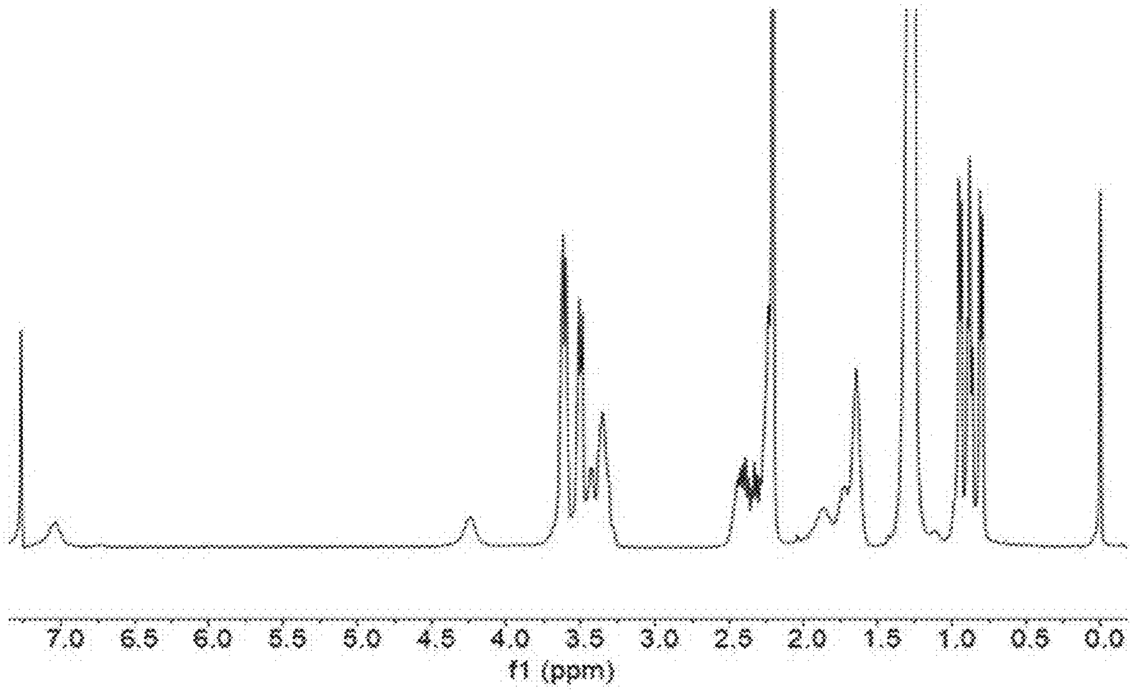
FIG. 3B shows a proton nuclear magnetic resonance spectrum of cationic lipid analog material I2-3R2C18A1.

Cationic lipid analog materials I2-1R2C18A1, I2R2C18A1, and I2-3R2C18A1 were selected as representative materials, and structures of these materials were characterized, where mass spectrometry and proton nuclear magnetic resonance spectra of I2-1R2C18A1 were shown in FIGS. 1A and 1B; mass spectrometry and proton nuclear magnetic resonance spectra of I2R2C18A1 were shown in FIGS. 2A and 2B; and mass spectrometry and proton nuclear magnetic resonance spectra of I2-3R2C18A1 were shown in FIGS. 3A and 3B. Results of proton nuclear magnetic resonance and mass spectrometry were consistent with the expected structures of the cationic lipid analog materials.

Example 2

In this example, BSA-FITC was used as a protein model to investigate the intracellular protein delivery of a cationic lipid analog material.

A specific experimental method was as follows: HeLa cells were inoculated in a 24-well plate and cultured in an incubator for 12 h in advance; different cationic lipid analog materials (0.25 μg/well to 8 μg/well) each were mixed with BSA-FITC (2 μg/well) in 50 μl of a N-2-hydroxyethylpiperazine-N-2-ethane sulfonic acid (HEPES) buffer, and resulting mixtures each were diluted with 450 μl of a serum-free Dulbecco's Modified Eagle Medium (DMEM) to obtain protein/cationic lipid analog complex solutions; a medium for the HeLa cells in the plate was removed, then the HeLa cells were washed once with phosphate buffered saline (PBS), and the protein/cationic lipid analog complex solutions were added; and the cells were cultured for 4 h, and then a fluorescence intensity in cells and a positive cell rate were analyzed by flow cytometry. In this experiment, the commercial protein delivery reagent PULSin® was adopted as a positive control.

Figure 4:
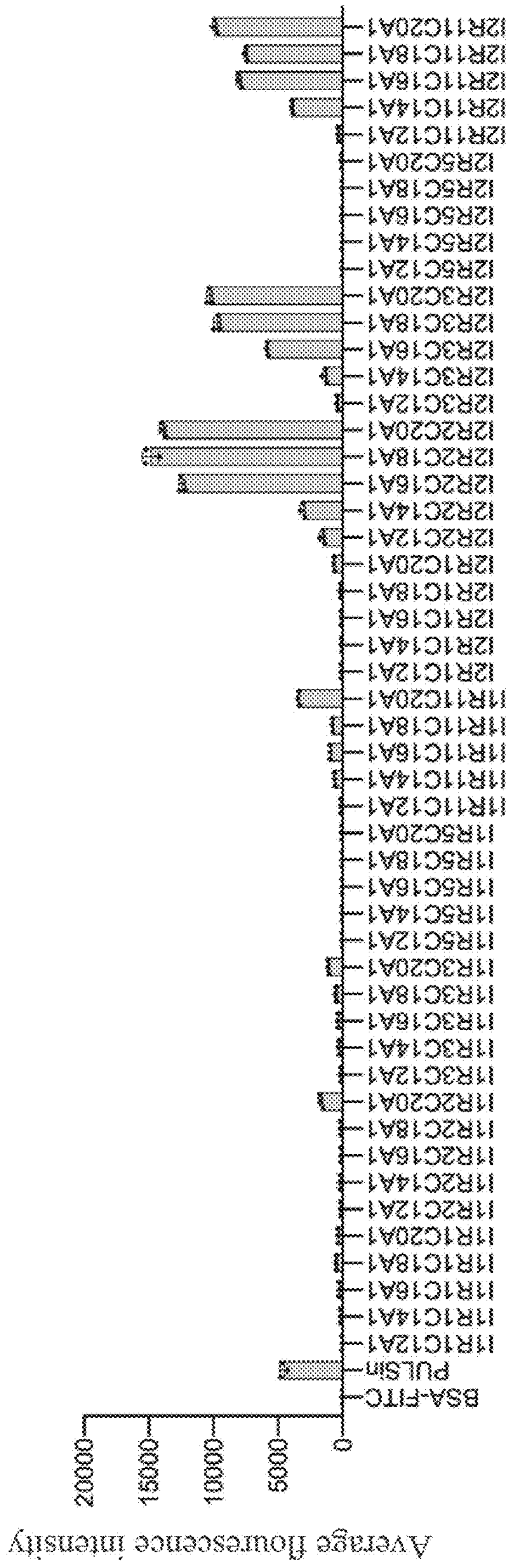
FIG. 4 shows average fluorescence intensities of fluorescently-labeled proteins in HeLa cells in which fluorescein isothiocyanate-labeled bovine serum albumin (BSA-FITC) is delivered by different cationic lipid analog materials: in the experiment, a dosage of I1R1C12A1, I2R1C14A1, and I2R3C16A1 is 1 μg/well; a dosage of I1R2C14A1, I1R2C16A1, I1R2C18A1, I1R3C18A1, I1R11C18A1, I2R1C12A1, I2R1C20A1, I2R2C16A1, I2R3C18A1, I2R11C14A1, I2R11C16A1, and I2R11C18A1 is 2 μg/well; a dosage of I1R3C14A1, I1R3C16A1, I1R3C20A1, I1R11C14A1, I1R11C16A1, I1R11C20A1, I2R2C18A1, I2R2C20A1, I2R3C20A1, and I2R11C20A1 is 4 μg/well; a dosage of I1R1C14A1, I1R1C16A, I1R1C18A1, I1R1C20A1, I1R2C12A1, I1R2C20A1, I1R3C12A1, I1R5C12A1, I1R5C14A1, I1R5C16A1, I1R5C18A1, I1R5C20A1, I1R11C12A1, I2R1C16A1, I2R1C18A1, I2R2C12A1, I2R2C14A1, I2R3C12A1, I2R3C14A1, I2R5C12A1, I2R5C14A1, I2R5C16A1, I2R5C18A1, I2R5C20A1, and I2R11C12A1 is 8 μg/well: and a dosage of BSA-FITC is 2 μg/well.
Figure 5:
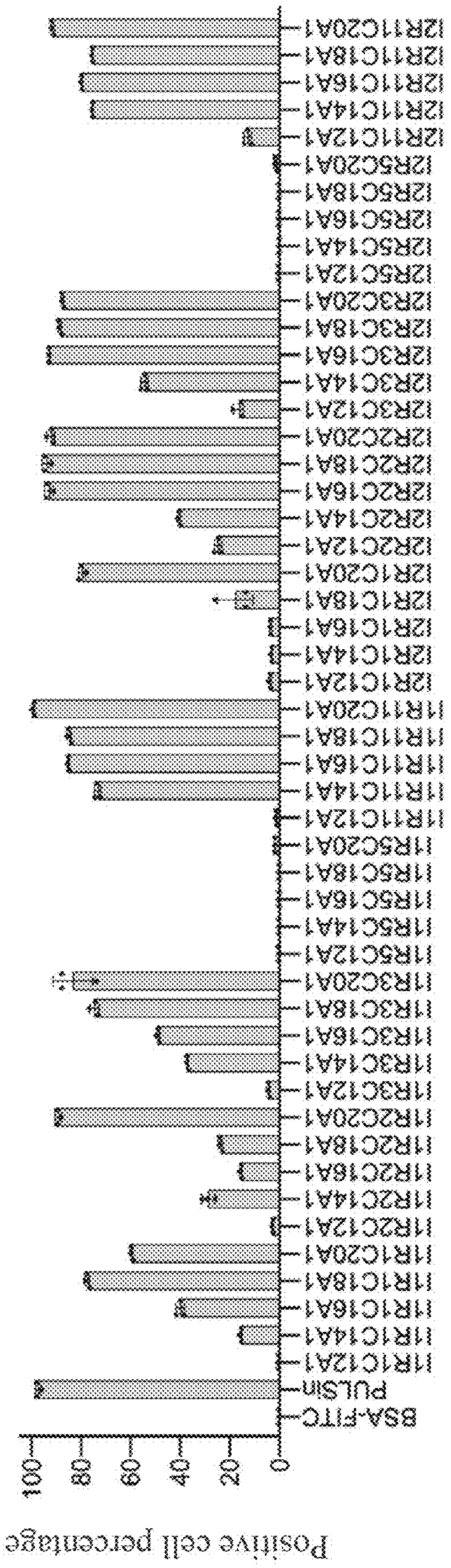
FIG. 5 shows percentages of HeLa cells positive for the fluorescently-labeled proteins after delivery of BSA-FITC using different cationic lipid analog materials, where the experimental conditions are consistent with those described in FIG. 4, respectively.

The results in FIG. 4 and FIG. 5 show that all of the cationic lipid analog materials of the present application exhibit an intracellular delivery effect for proteins to some degree; and in particular, when the isocyanide compound is I2 and the amine compound is R2, R3, or R11, most of the synthesized cationic lipid analog materials have significantly-better delivery efficiency than the commercial protein delivery reagent PULSin®.

Figure 6:
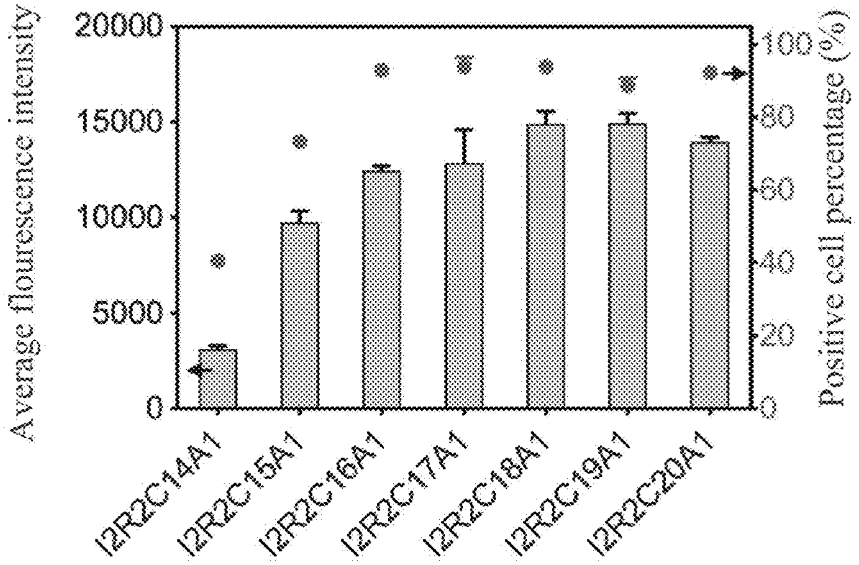
FIG. 6 shows average fluorescence intensities of fluorescently-labeled proteins in HeLa cells after delivery of BSA-FITC using cationic lipid analog materials with different alkyl chain lengths, where the dosage of a cationic lipid analog material is 4 μg/well, and a dosage of BSA-FITC is 2 μg/well.

In this experiment, with I2R2C14A1, I2R2C15A1, I2R2C16A1, I2R2C17A1, I2R2C18A1, I2R2C19A1, and I2R2C20A1 as representatives, average fluorescence intensities of cellular proteins of the cationic lipid analog materials with different alkyl chain lengths were compared. The results in FIG. 6 show that, in the present application, an alkyl chain length of a carboxylic acid compound can be increased to adjust the hydrophobicity of a cationic lipid analog material; and an intracellular protein delivery efficiency of a cationic lipid analog material is also increased with the increase of an alkyl chain length, and reaches a platform value when the number of carbon atoms of an alkyl chain of the carboxylic acid compound is 18.

Figure 7A:
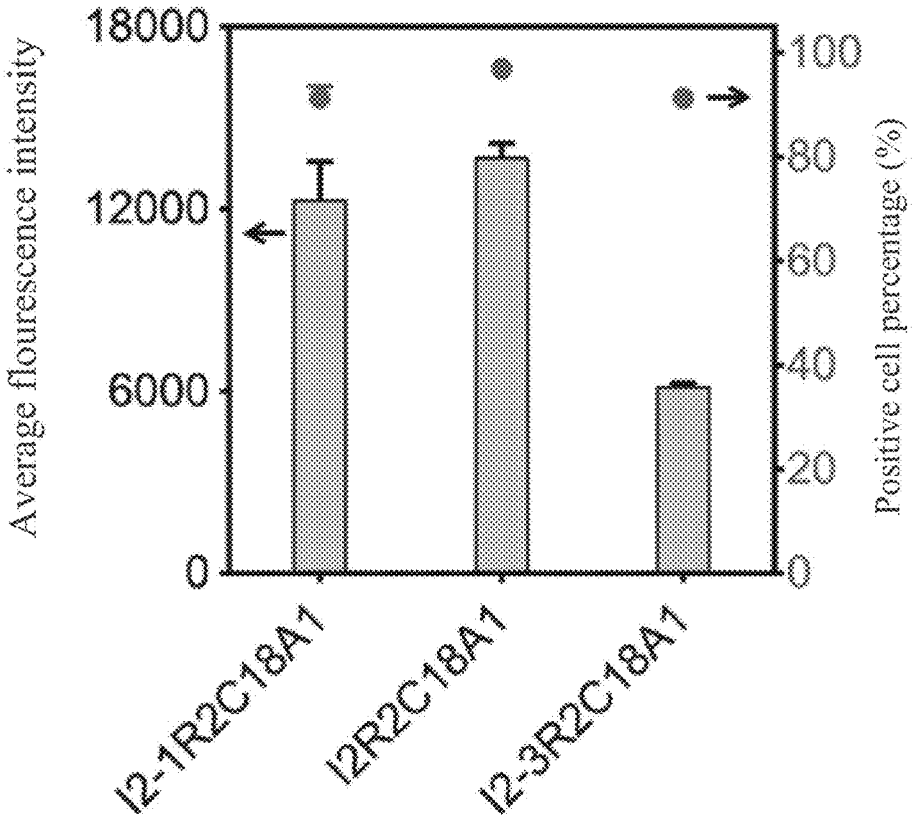
FIG. 7A and FIG. 7B show BSA-FITC intracellular delivery efficiencies corresponding to I2-1R2C18A1, I2R2C18A1, and I2-3R2C18A1 (FIG. 7A), and particle size distributions of corresponding complexes (FIG. 7B)
Figure 7B:
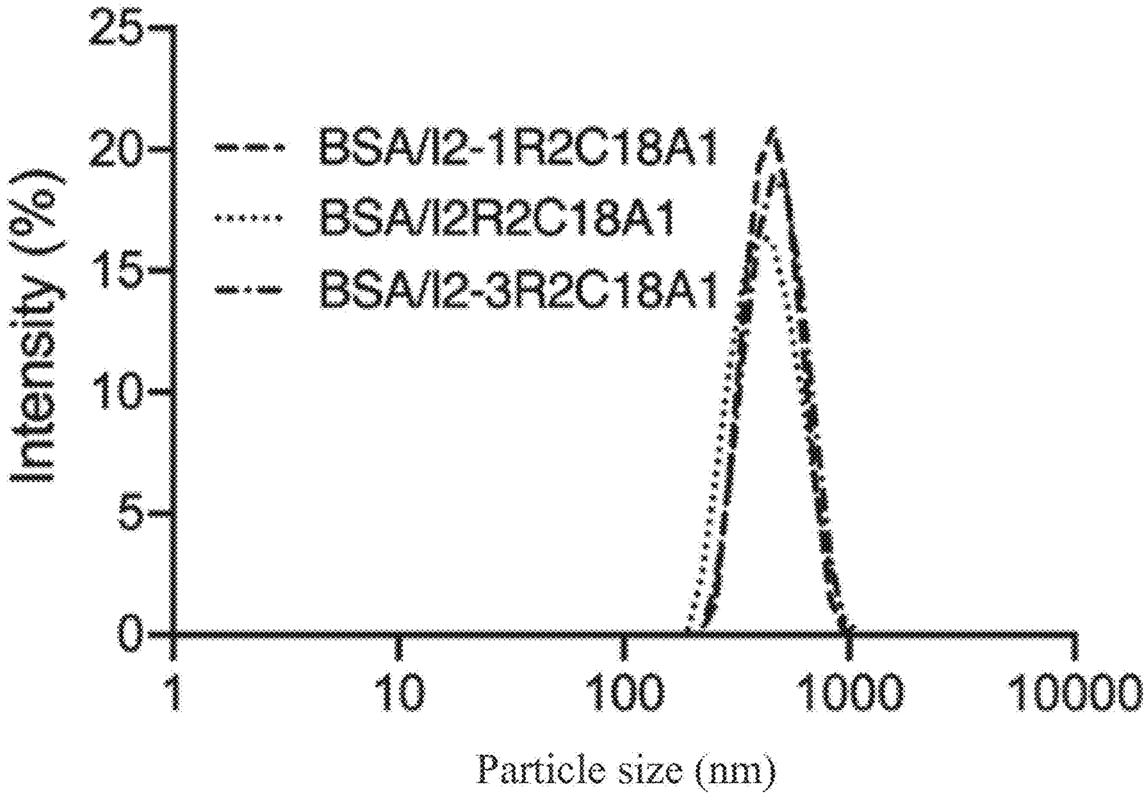

In this experiment, with I2-1R2C18A1, I2R2C18A1, and I2-3R2C18A1 as representatives, particle sizes of corresponding protein/cationic lipid analog complexes were determined. It can be seen from the results in FIGS. 7A and 7B that I2-1R2C18A1, I2R2C18A1, and I2-3R2C18A1 all have excellent intracellular delivery efficiencies for proteins (a dosage of a cationic lipid analog was 4 μg/well and a dosage of BSA-FITC was 2 μg/well), and they bind to BSA to produce a complex with a small size and a homogeneous distribution, and the complex has a particle size of about 500 nm.

Example 3 Protein Delivery Effects of I2-1R2C18A1 in Different Types of Cells

In this experiment, I2-1R2C18A1 was selected as a representative cationic lipid analog material, and protein delivery effects of the cationic lipid analog material in different types of cells were investigated.

In this experiment, a BSA-FITC/I2-1R2C18A1 complex solution was prepared with reference to the method in Example 2, where a dosage of I2-1R2C18A1 was 4 μg/well and a dosage of BSA-FITC was 4 μg/well; and the BSA-FITC/I2-1R2C18A1 complex solution was added to human renal epithelial cells (HRECs) (HEK-293T), human pancreatic cancer cells (BxPC3), mouse macrophages (RAW 264.7), mouse dendritic cells (DCs) (DC 2.4), human umbilical vein endothelial cells (HUVECs), and mouse mesenchymal stem cells (MSCs), respectively, then these cells each were cultured for 4 h, and then an FITC fluorescence signal in cells was observed by LSCM.

Figure 8:
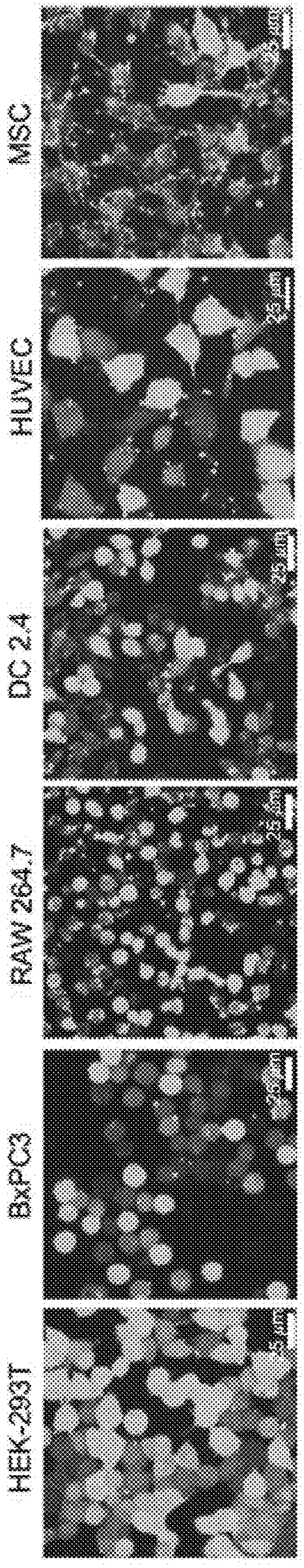
FIG. 8 shows laser scanning confocal microscopy images of different types of cells in which BSA-FITC is delivered by I2-1R2C18A1.

The results in FIG. 8 show that BSA-FITC can be intracellularly delivered by I2-1R2C18A1 into epithelial cells: HRECs (HEK-293T); cancer cells: human pancreatic cancer cells (BxPC3); immune cells: mouse macrophages (RAW 264.7) and mouse DCs (DC 2.4); endothelial cells: HUVECs; and stem cells: mouse MSCs. It can be seen that I2-1R2C18A1 exhibits excellent protein delivery effects in different types of cells.

Example 4 Cytotoxicity Test of Cationic Lipid Analog Materials and Corresponding Complexes In this experiment, I2R2C16A1, I2R2C17A1, I2R2C18A1, I2R2C19A1, and I2R2C20A1 with high protein delivery efficiencies were selected as representative cationic lipid analog materials, and the toxicity of protein/cationic lipid analogs for HeLa cells was detected by an MTT experiment. A specific experimental method was as follows: HeLa cells were inoculated in a 96-well plate and cultured in an incubator for 12 h, then a medium was removed, and a cationic lipid analog material or a BSA-FITC/cationic lipid analog complex (a mass ratio of the cationic lipid analog material to the BSA-FITC was 2:1) was added at 1 μg/well; the cells were further cultured for 4 h, then the material was washed away and replaced with DMEM; and the cells were further cultured for 20 h, and finally cell viability was detected by MTT.

Figure 9:
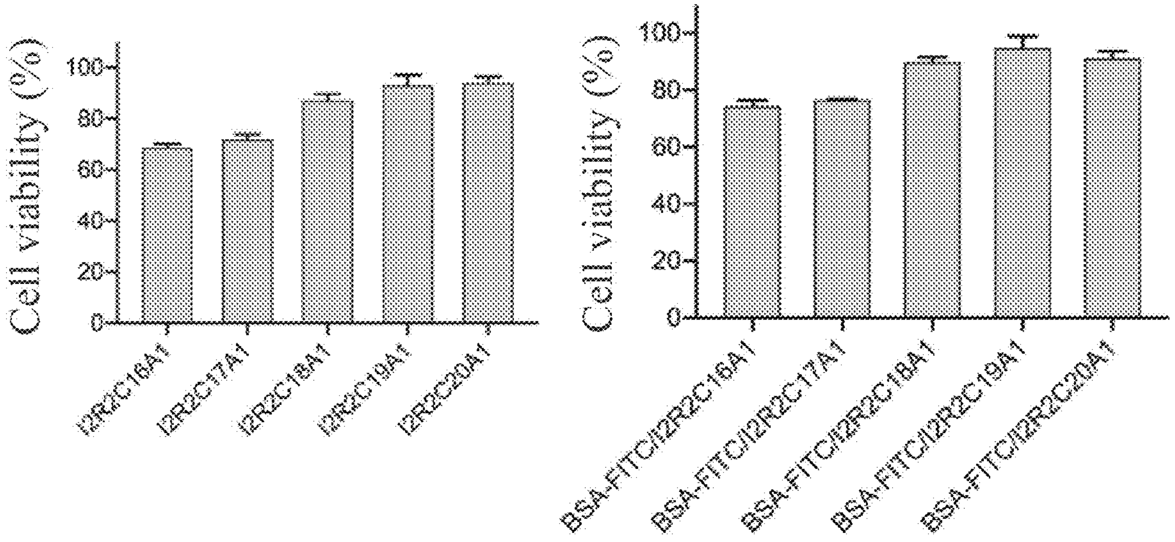
FIG. 9 shows cytotoxicity results of I2R2C16A1, I2R2C17A1, I2R2C18A1, I2R2C19A1, and I2R2C20A1 and complexes of them with BSA-FITC, respectively.

The results in FIG. 9 show that the cationic lipid analog materials of the present application and a complex of the materials with a protein have low toxicity to cells and have excellent biocompatibility.

Example 5 Intracellular Delivery Effects of a Cationic Lipid Analog Material for Different Proteins In this experiment, intracellular delivery effects of the cationic lipid analog material for phycoerythrin (R-PE), superoxide dismutase, ovalbumin, green fluorescent protein, cytochrome C, and lysozyme were investigated. In this experiment, a protein/cationic lipid analog complex solution was prepared with reference to the method in Example 2, and a delivery effect of the complex solution in HeLa cells was investigated.

Figure 10:
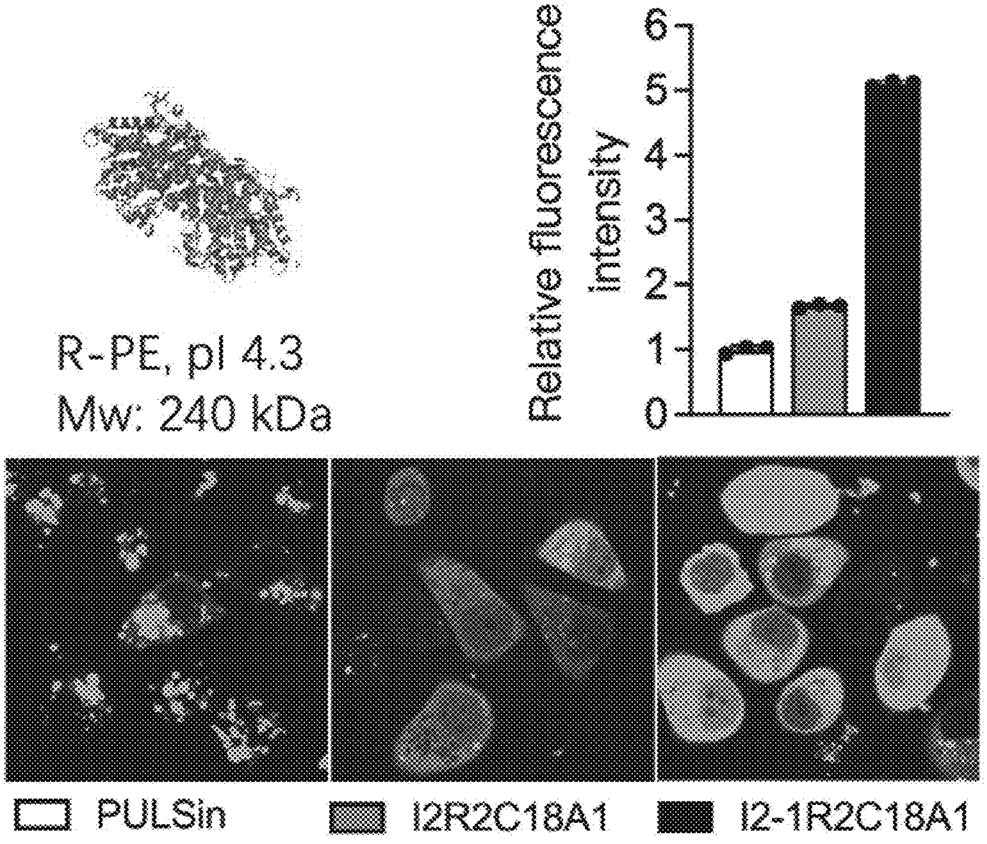
FIG. 10 shows intracellular delivery efficiencies of I2R2C18A1, I2-1R2C18A1, and a positive control PULSin® for negatively-charged phycoerythrin (R-PE)
Figure 11:
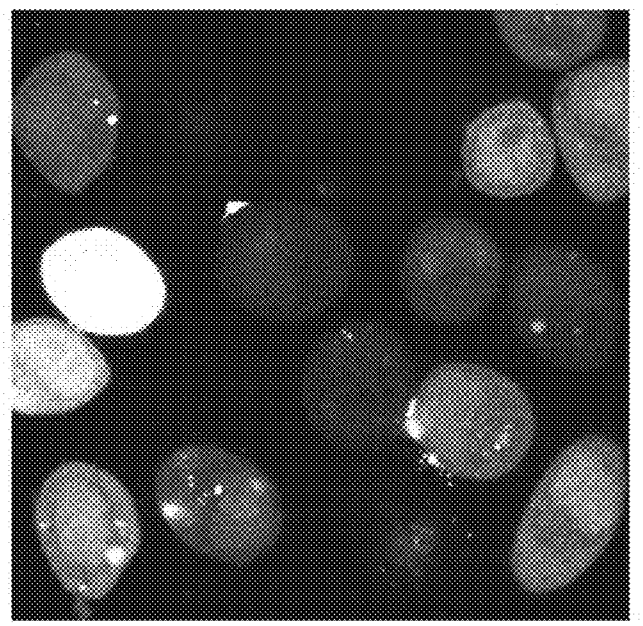
FIG. 11 shows an intracellular delivery efficiency of I2-1R2C18A1 for negatively-charged superoxide dismutase.
Figure 12:
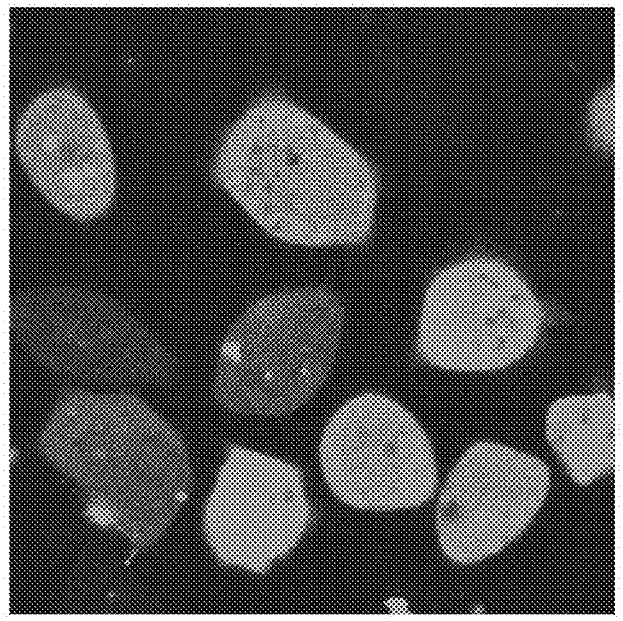
FIG. 12 shows an intracellular delivery efficiency of I2-1R2C18A1 for negatively-charged ovalbumin.
Figure 13:
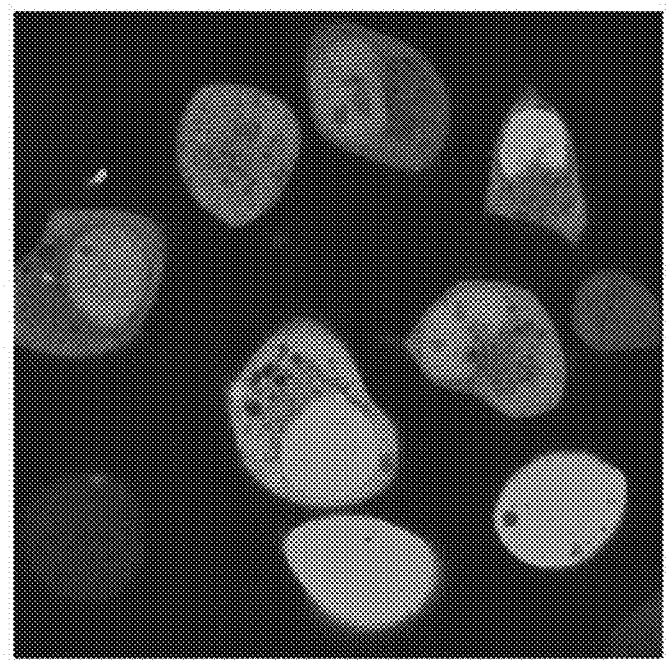
FIG. 13 shows an intracellular delivery efficiency of I2-1R2C18A1 for negatively-charged green fluorescent protein.
Figure 14:
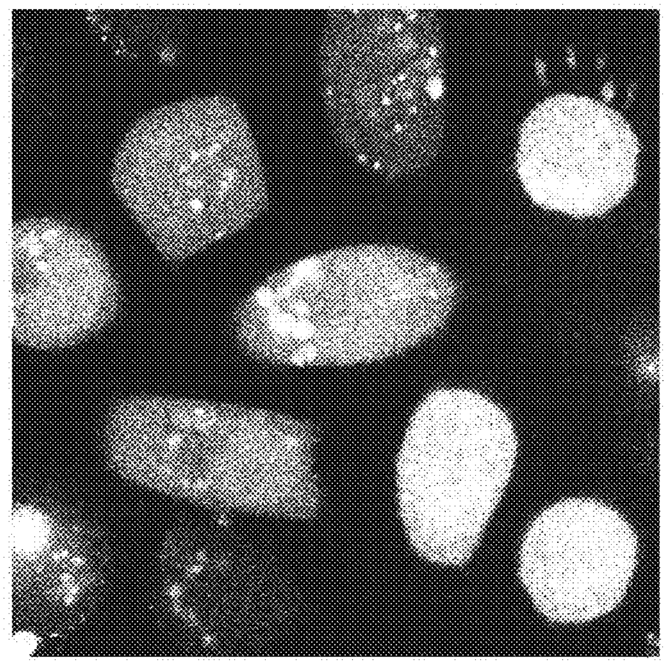
FIG. 14 shows an intracellular delivery efficiency of I2-1R2C18A1 for positively-charged cytochrome C.
Figure 15:
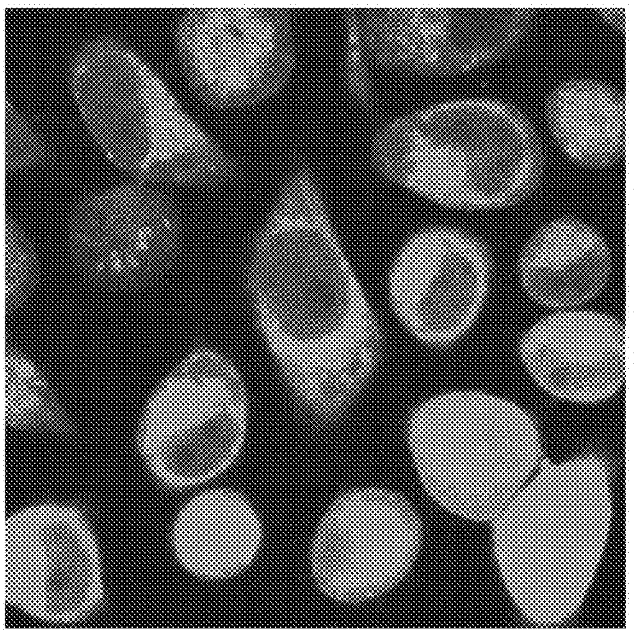
FIG. 15 shows an intracellular delivery efficiency of I2-1R2C18A1 for a positively-charged lysozyme.

Thereinto, delivery effects of I2R2C18A1, I2-1R2C18A1, and a positive control PULSin® for negatively-charged phycoerythrin were shown in FIG. 10; a delivery effect of I2-1R2C18A1 for negatively-charged superoxide dismutase was shown in FIG. 11; a delivery effect of I2-1R2C18A1 for negatively-charged ovalbumin was shown in FIG. 12; a delivery effect of I2-1R2C18A1 for negatively-charged green fluorescent protein was shown in FIG. 13; a delivery effect of I2-1R2C18A1 for positively-charged cytochrome C was shown in FIG. 14; and a delivery effect of I2-1R2C18A1 for positively-charged lysozyme was shown in FIG. 15. The above results show that the cationic lipid analog material of the present application can efficiently deliver proteins of different molecular weights and different charged properties into cells, such as bovine serum albumin, phycoerythrin, superoxide dismutase, ovalbumin, green fluorescent protein, cytochrome C, and lysozyme, indicating that the cationic lipid analog material of the present application has universal applicability in terms of intracellular delivery of protein drugs.

Example 6 Delivery of β-Galactase (β-Gal) by I2-1R2C18A1 and Detection of Activity of β-Gal in Cells In this experiment, β-Gal was selected as a model protein to detect the biological activity of enzymes after intracellular delivery, and then evaluate whether proteins maintain biological functions after intracellular delivery. The specific operation method was as follows: HeLa cells were cultured with β-Gal, β-Gal/PULSin, or β-Gal/I2-1R2C18A1 for 4 h and then washed with PBS, and then the activity of β-Gal in cells was detected with a β-Gal in situ assay kit according to instructions.

Figure 16:
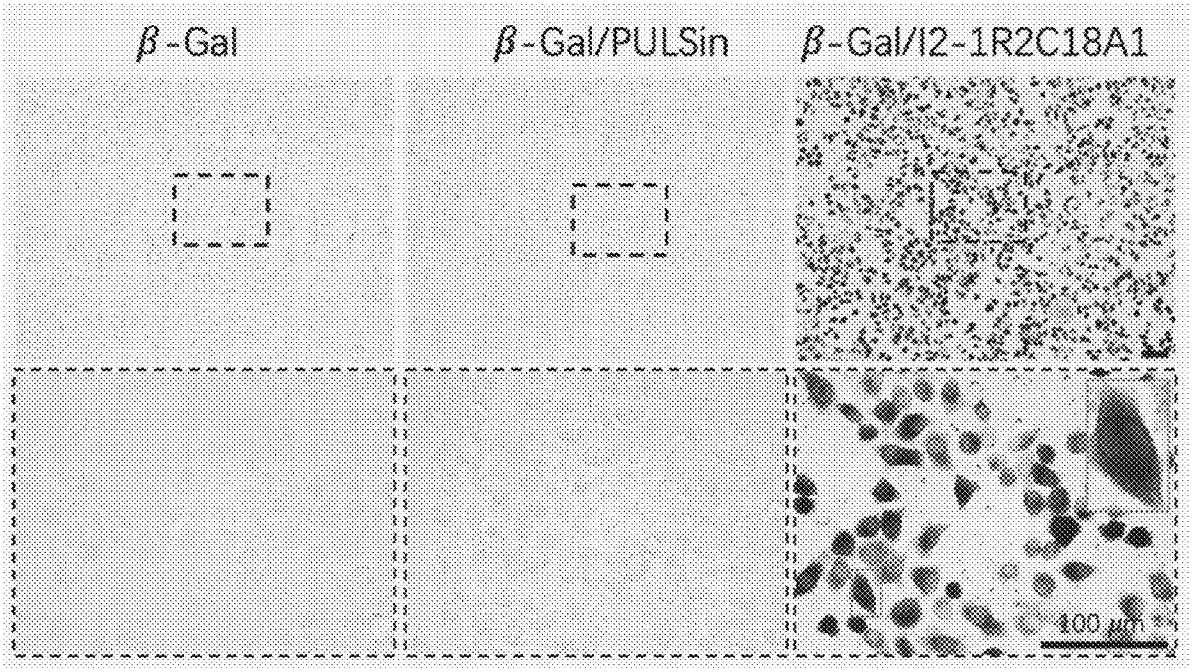
FIG. 16 shows activity results of β-galactosidase in HeLa cells in which β-galactosidase is delivered, where a dosage of a cationic lipid analog material is 4 μg/well and a dosage of β-galactosidase is 4 μg/well; wherein each of the lower pictures bounded by rectangular dotted lines is an enlarged view of a part of the corresponding upper picture.

It can be seen from the results in FIG. 16 that I2-1R2C18A1 can efficiently deliver β-Gal into cells while retaining its biological activity. The effectiveness of I2-1R2C18A1 is significantly better than that of the commercially available protein delivery reagent PULSin®.

Example 7 Delivery of Saporin into HeLa Cells by I2-1R2C18A1 and Detection of Cell Viability HeLa cells were incubated with saporin or saporin/I2-1R2C18A1 for 4 h, then the material was replaced by a complete medium, the cells were further cultured for 20 h, and then cell viability was detected by an MTT method.

Figure 17:
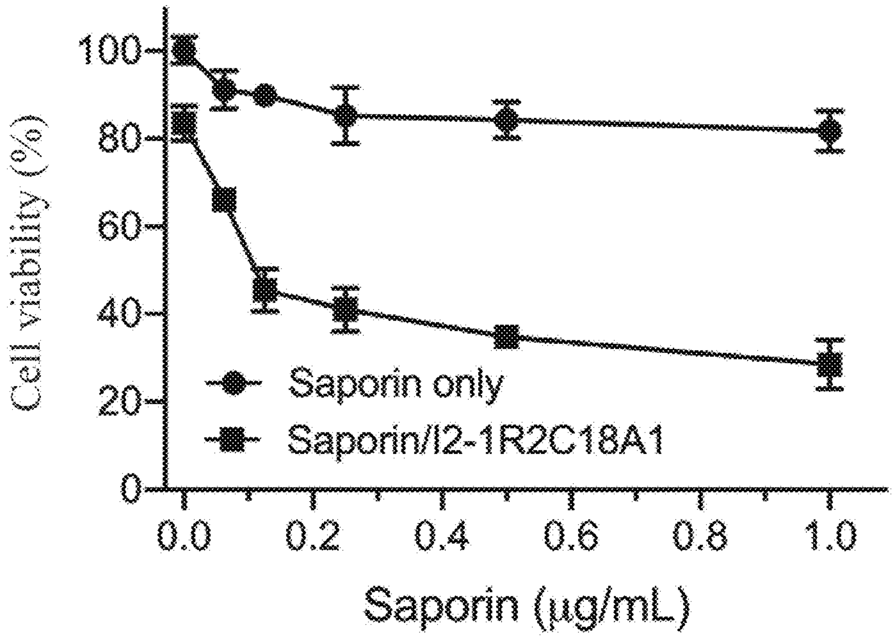
FIG. 17 shows cell viability results of HeLa cells in which saporin is delivered by I2-1R2C18A1, where a dosage of a cationic lipid analog material is 3 μg/well.

The results in FIG. 17 show that saporin itself exhibits minimal toxicity for cells; and I2-1R2C18A1 can effectively deliver saporin into cells due to its high protein delivery efficiency, and saporin delivered into the cells has a therapeutic function and can effectively kill tumor cells.

In addition, the inventors have found in previous research that, when the isobutyl aldehyde in Example 1 is replaced by

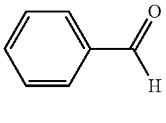 and 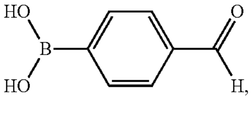, prepared cationic lipid analog materials also have low cytotoxicity, and when BSA-FITC is adopted as a protein model, these cationic lipid analog materials also exhibit a specified intracellular delivery effects for the protein in HeLa cells. Therefore, it is reasonable to assume that these cationic lipid analog materials can also be used as delivery carriers for protein drugs.

Finally, it should be noted that the above examples are provided merely to describe the technical solutions of the present application, rather than to limit the protection scope of the present application. Although the present application is described in detail with reference to preferred examples, a person of ordinary skill in the art should understand that modifications or equivalent replacements may be made to the technical solutions of the present application without departing from the spirit and scope of the technical solutions of the present application.

The invention claimed is:

1. A method of delivering a protein drug into a cell, comprising utilization of a cationic lipid analog material, wherein the cationic lipid analog material is an ionizable cationic lipid analog material with a structure shown in formula (I):

I

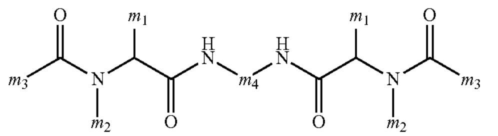

in formula (I), $m_1$ is independently selected from the group consisting of a linear alkyl, a branched alkyl, phenyl, or a heteroatom-containing aryl;

$m_2$ is

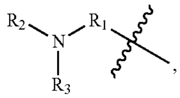

$R_1$ is an alkyl, $R_2$ is an alkyl, $R_3$ is an alkyl or phenyl, or $R_2$ and $R_3$ are connected as a cyclic group or a heterocyclic group;

$m_3$ is independently selected from the group consisting of a linear alkyl, a linear alkenyl, or

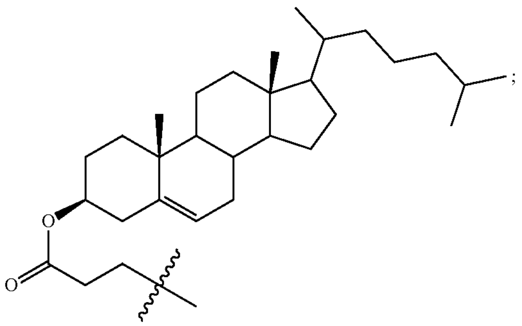 [SMILES: *CCC(=O)O[C@H]1CC[C@@]2(C)C(=CCC3C4CCC(C(C)CCCC(C)C)[C@@]4(C)CCC32)C1]

and $m_4$ is independently selected from the group consisting of a linear alkyl, an ether bond-containing linear alkyl, or an N-heterocycle-containing alkyl.

2. The method according to claim 1, wherein $m_1$ is selected from the group consisting of an alkyl, phenyl, or a heteroatom-containing aryl substituted by a substituent α, and the substituent comprises methyl.

3. The method according to claim 2, wherein $m_1$ is selected from the group consisting of

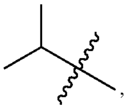
,
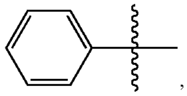
, or
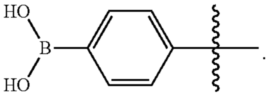

4. The method according to claim 1, wherein $m_2$ is selected from the group consisting of

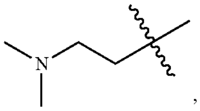
,
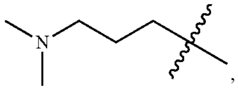
,
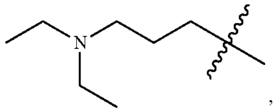
,
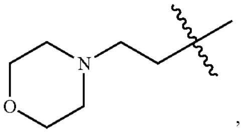
,
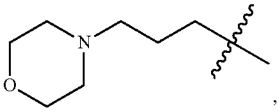
,
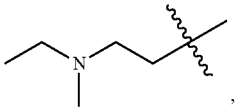
,
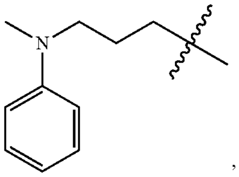
,
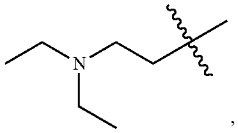
,
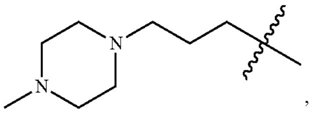
,
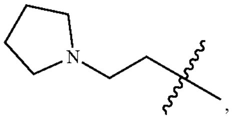
, or
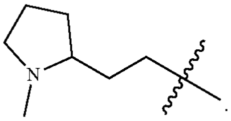

5. The method according to claim 4, wherein $m_2$ is selected from the group consisting of

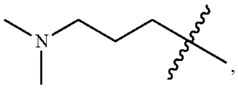,
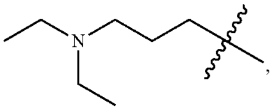, or
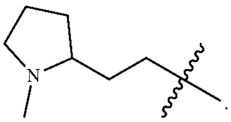.

6. The method according to claim 1, wherein $m_3$ is selected from the group consisting of a linear alkyl with 7 to 19 carbon atoms, a linear alkenyl with 17 carbon atoms, or

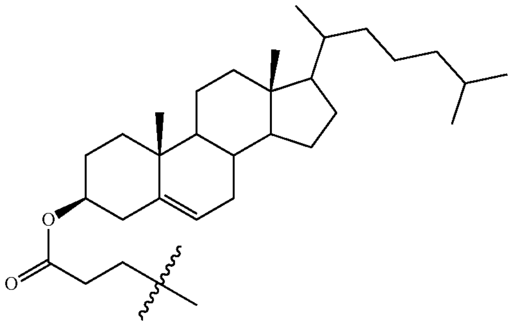.

7. The method according to claim 6, wherein $m_3$ is selected from the group consisting of

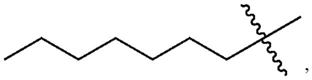,
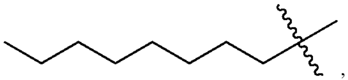,
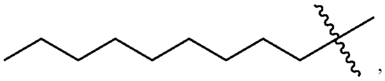,
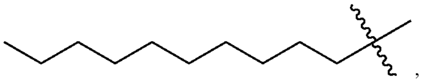,

-continued

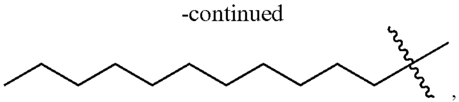,
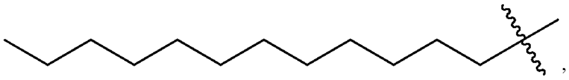,
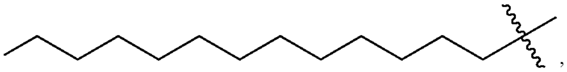,
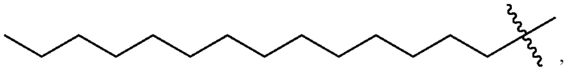,
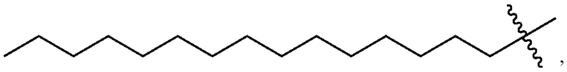,
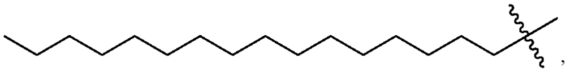,
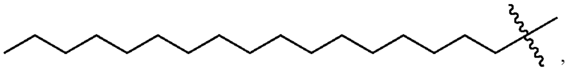,
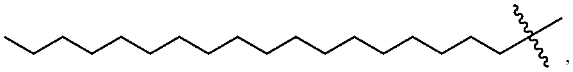,
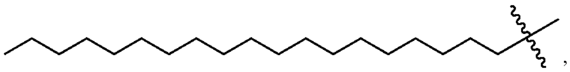,
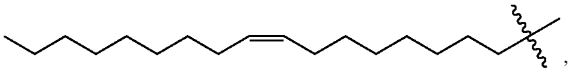,
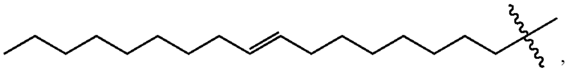,
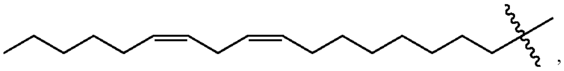,
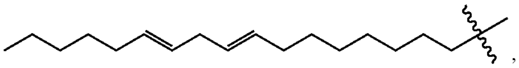, or
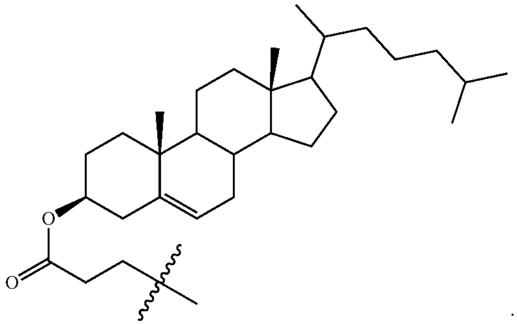.

8. The method according to claim 7, wherein $m_3$ is selected from the group consisting of

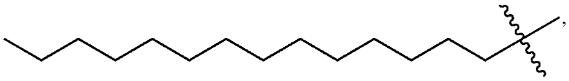,
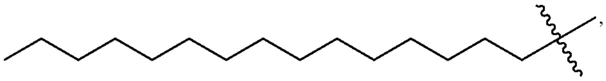,
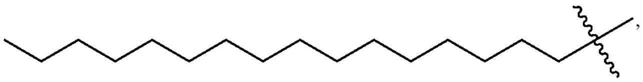,
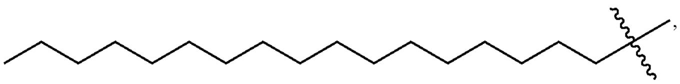,

-continued

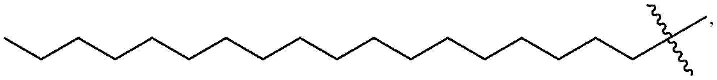

, or

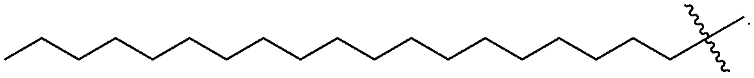

9. The method according to claim 1, wherein $m_4$ is selected from the group consisting of a linear alkyl with 6 carbon atoms, an ether bond-containing linear alkyl with 4 to 8 carbon atoms, or an N-heterocycle-containing alkyl.

10. The method according to claim 9, wherein $m_4$ is selected from the group consisting of

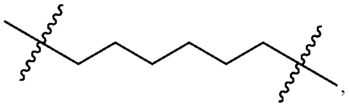

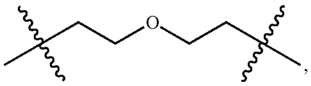

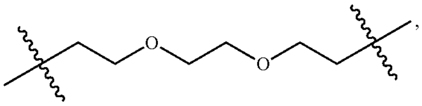

-continued

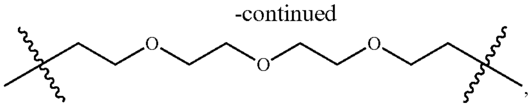

, or

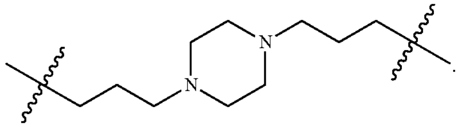

11. The method according to claim 10, wherein $m_4$ is

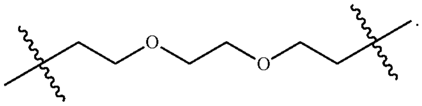 [SMILES: *CCOCCOCC*]

12. The method according to claim 1, wherein the ionizable cationic lipid analog material has a structure selected from the group consisting of the following 72 structures:

I1R1C12A1

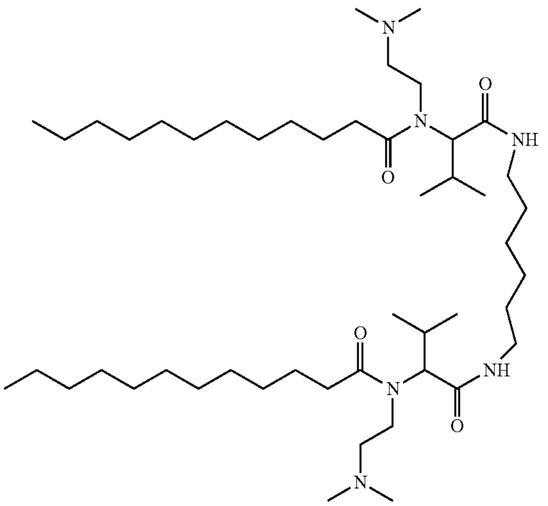

I1R1C14A1

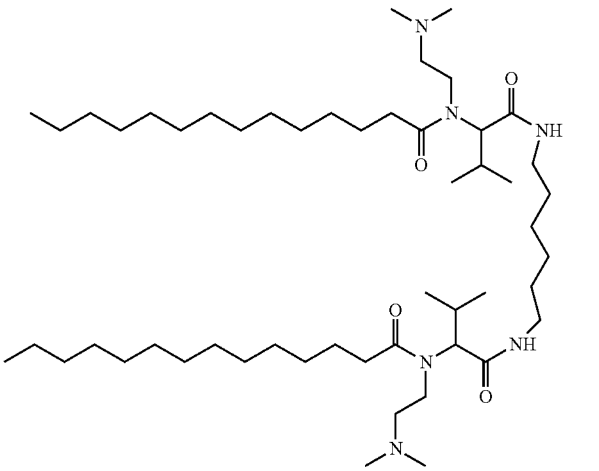

-continued
I1R1C16A1
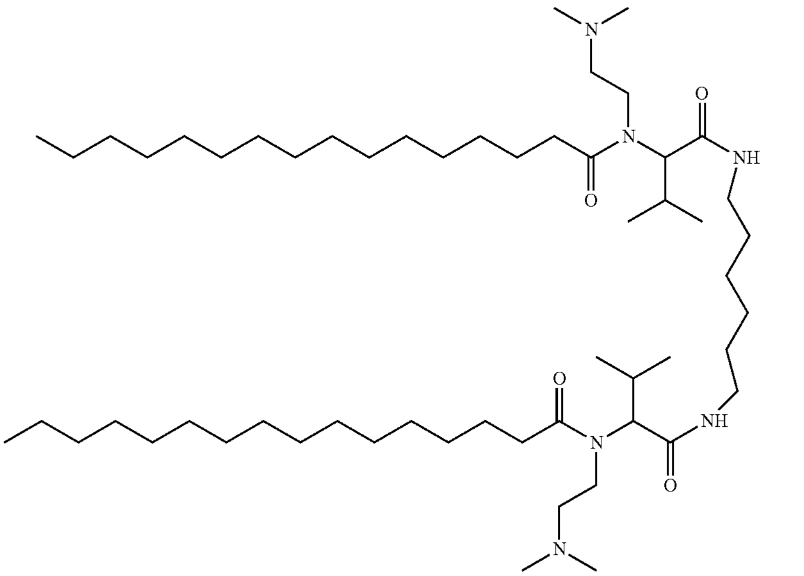
I1R1C18A1
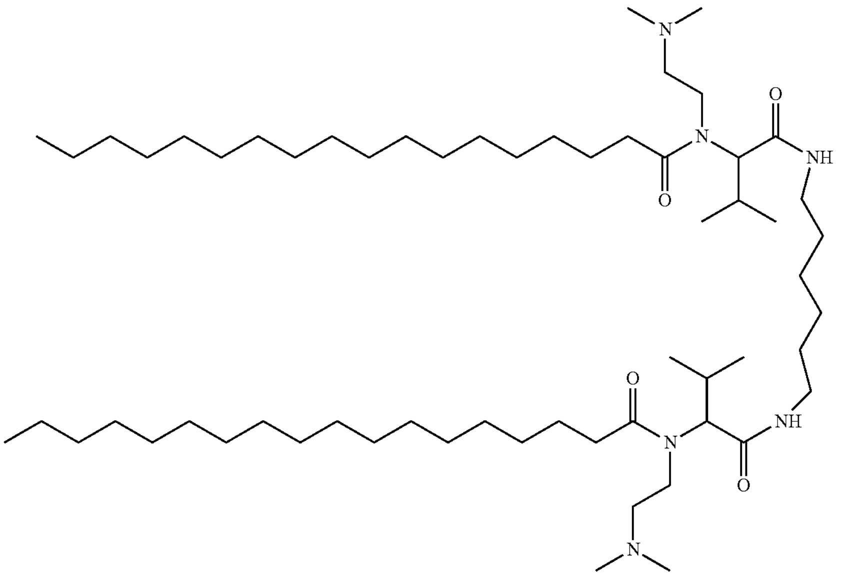

-continued
I1R1C20A1
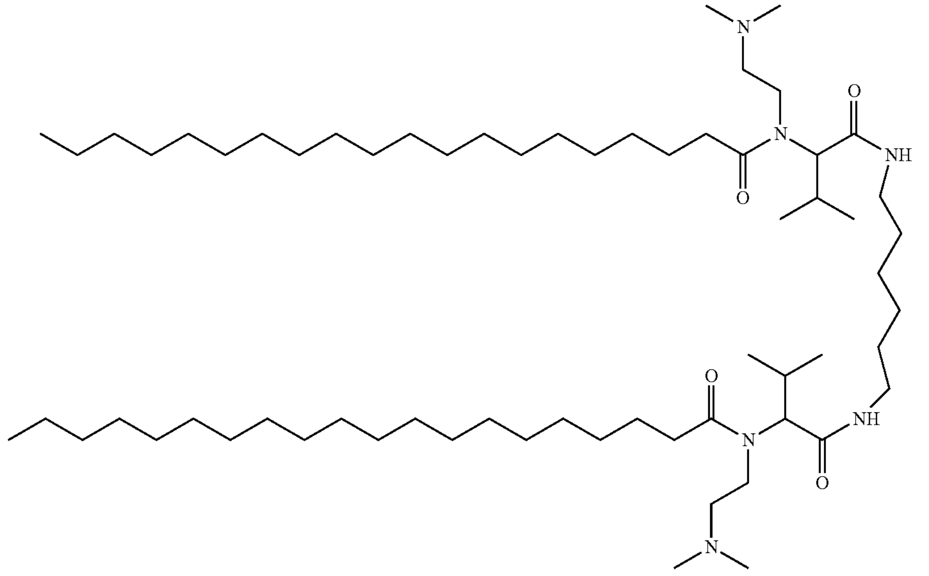
I1R1C18-1A1
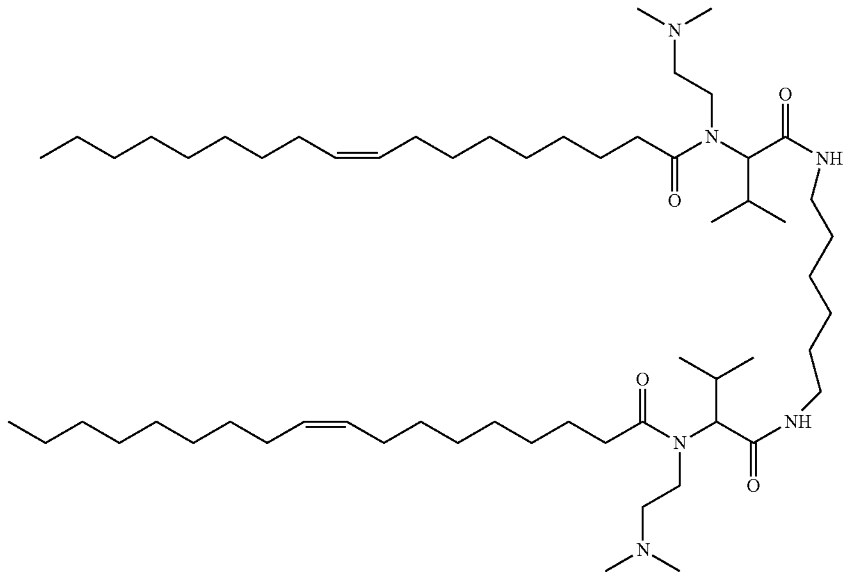

-continued
I1R3C14A1
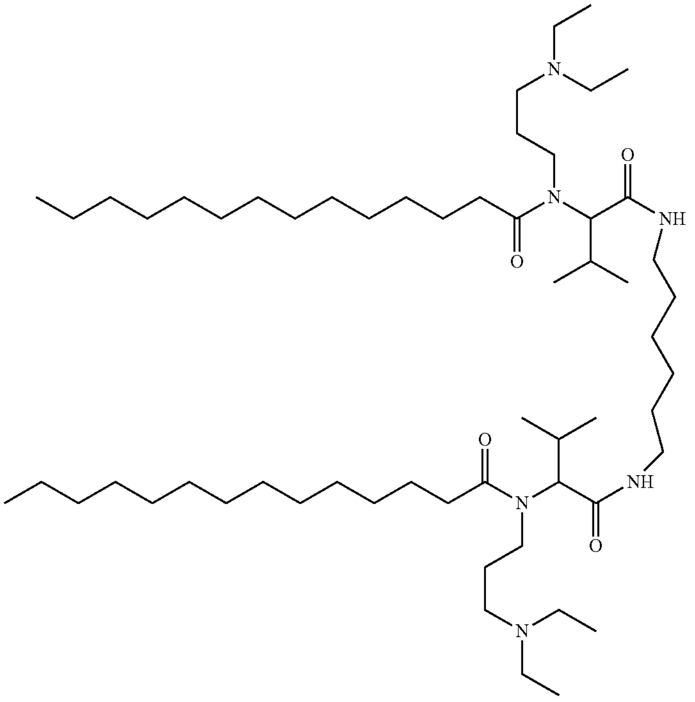
I1R1C18-2A1
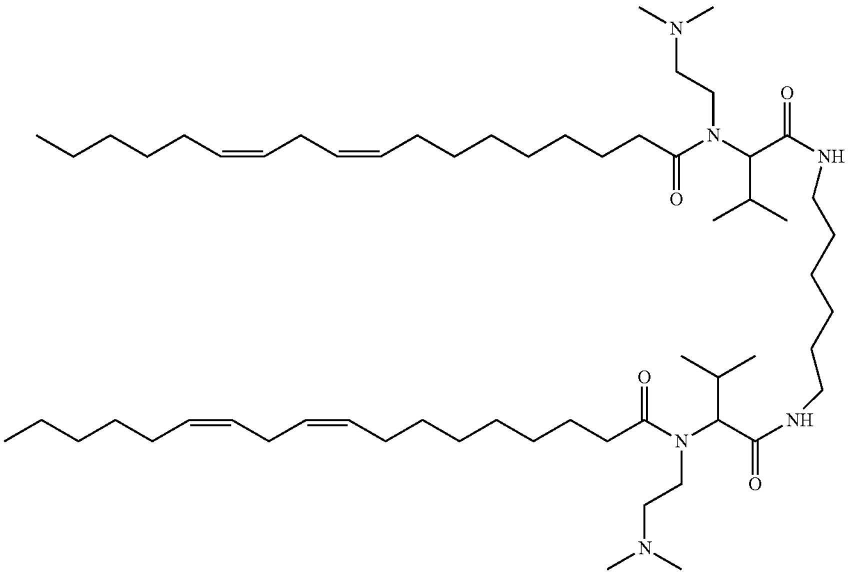

-continued
I1R2C12A1
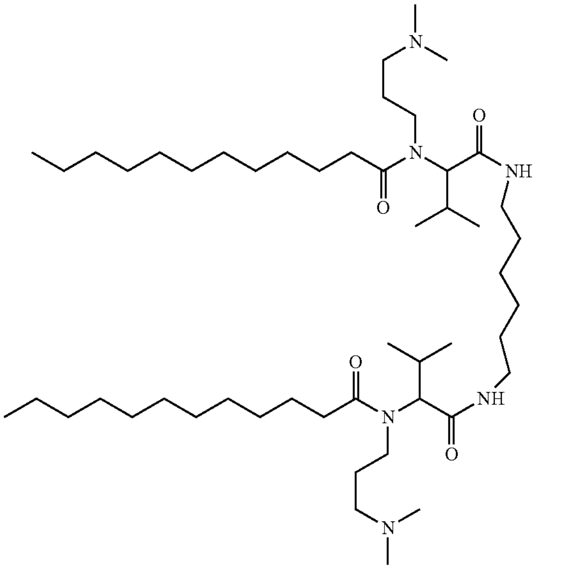
I1R2C14A1
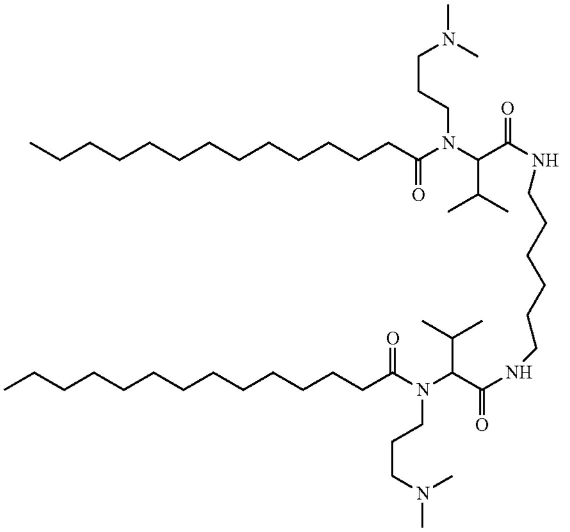
I1R2C16A1
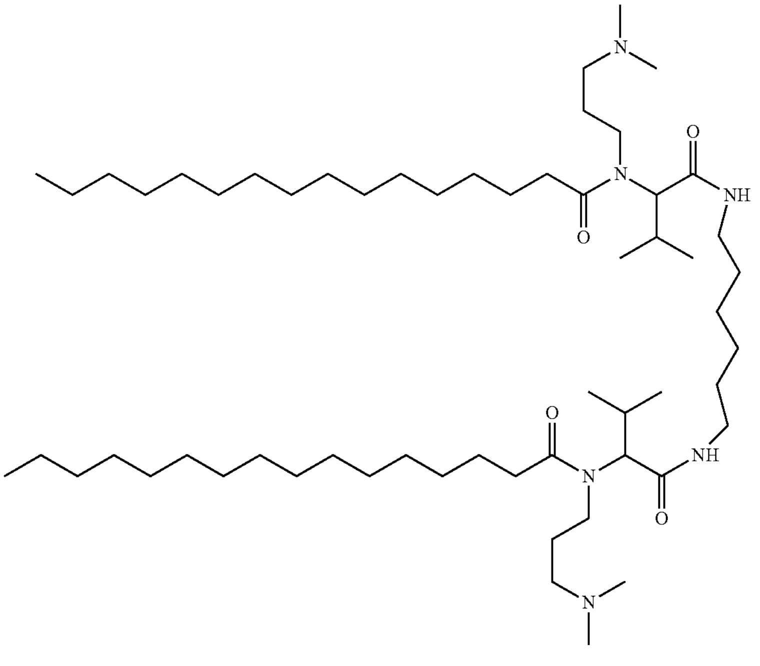

-continued
I1R2C18A1
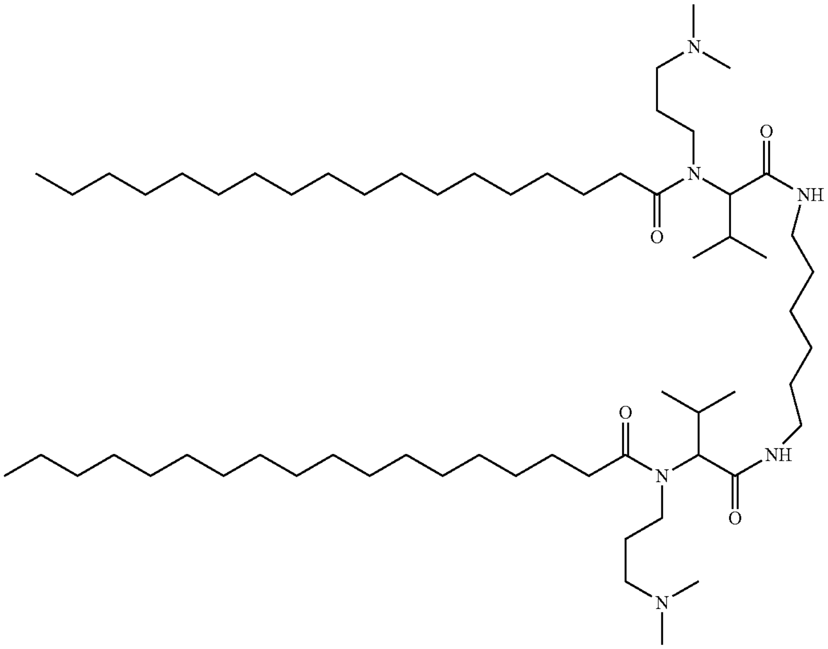
I1R2C20A1
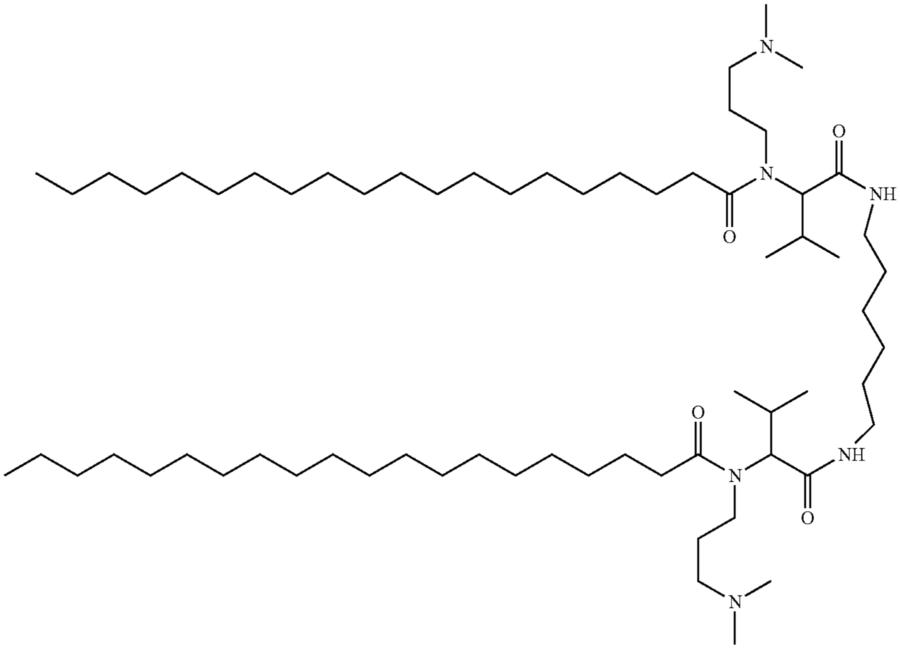

-continued
I1R2C18-1A1
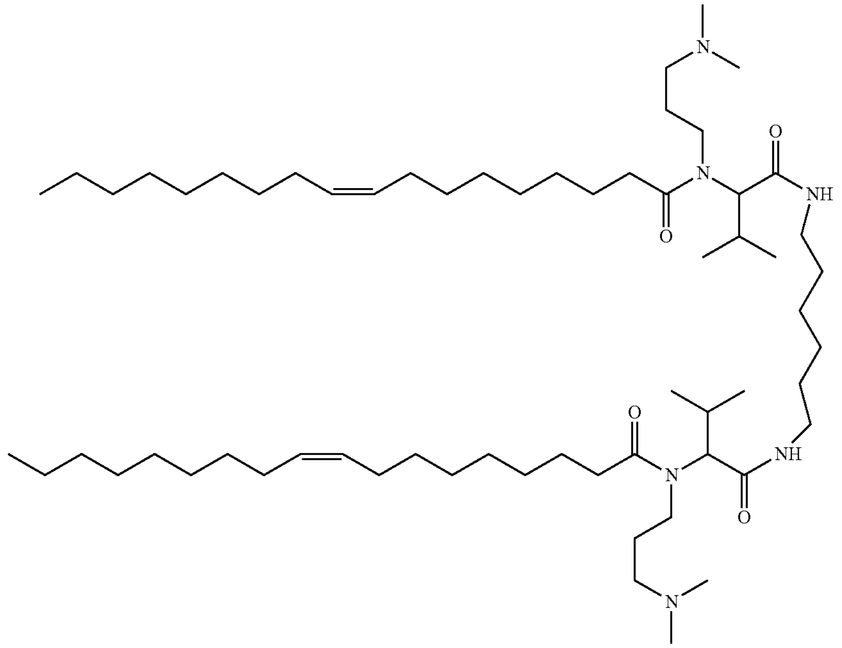
I1R2C18-2A1
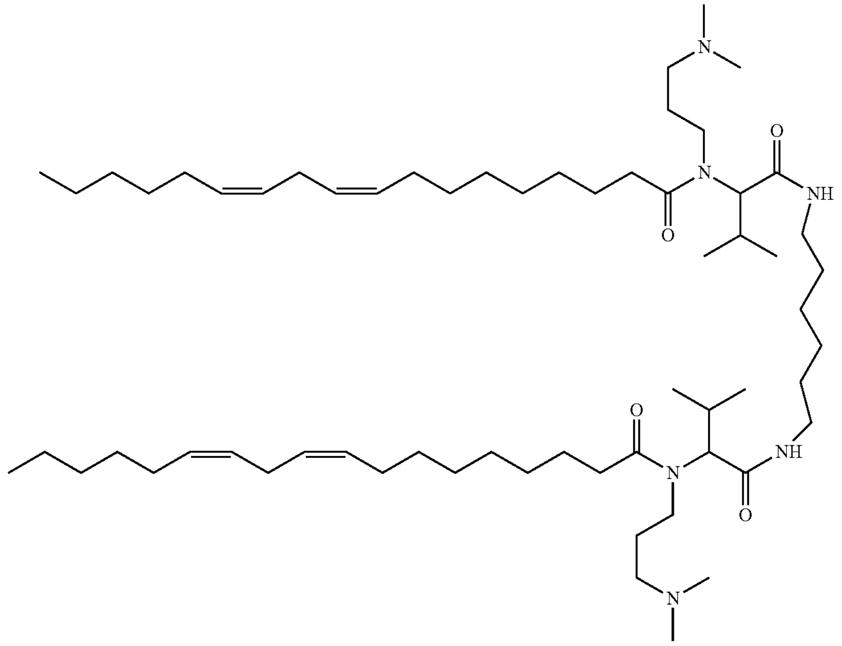

-continued
I1R3C12A1
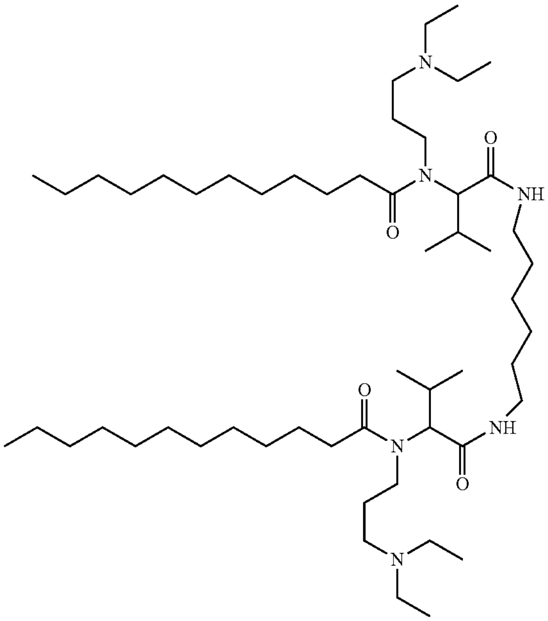
I1R3C16A1
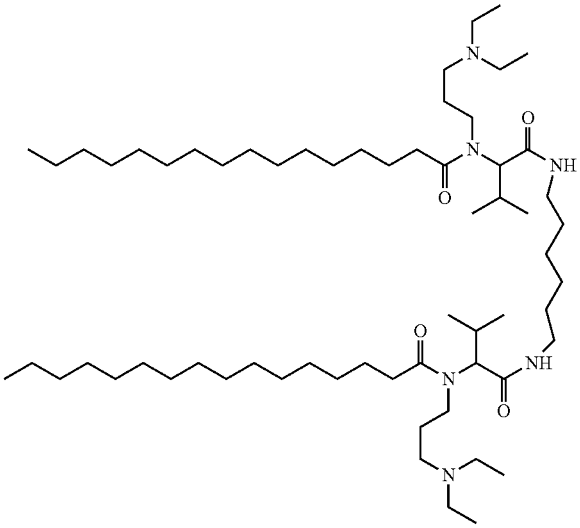
I1R3C18A1
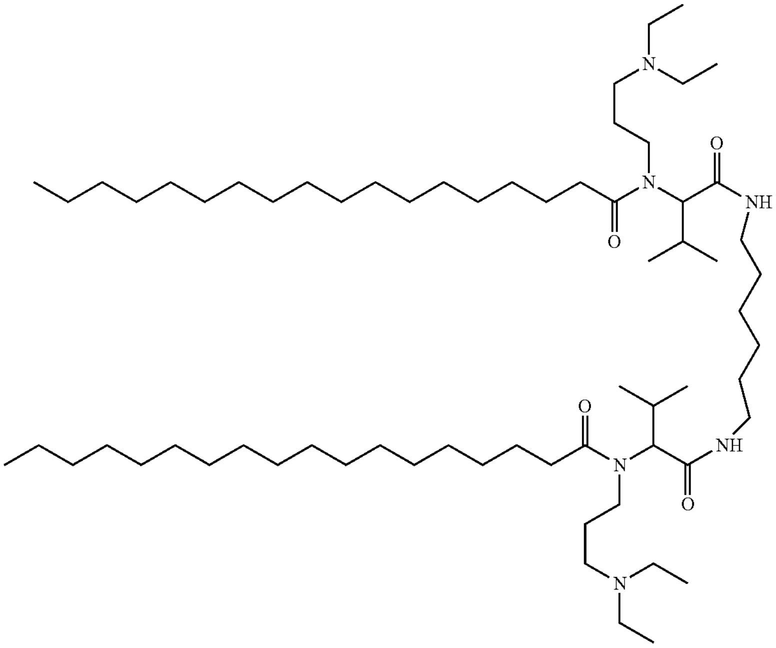

-continued
I1R3C20A1
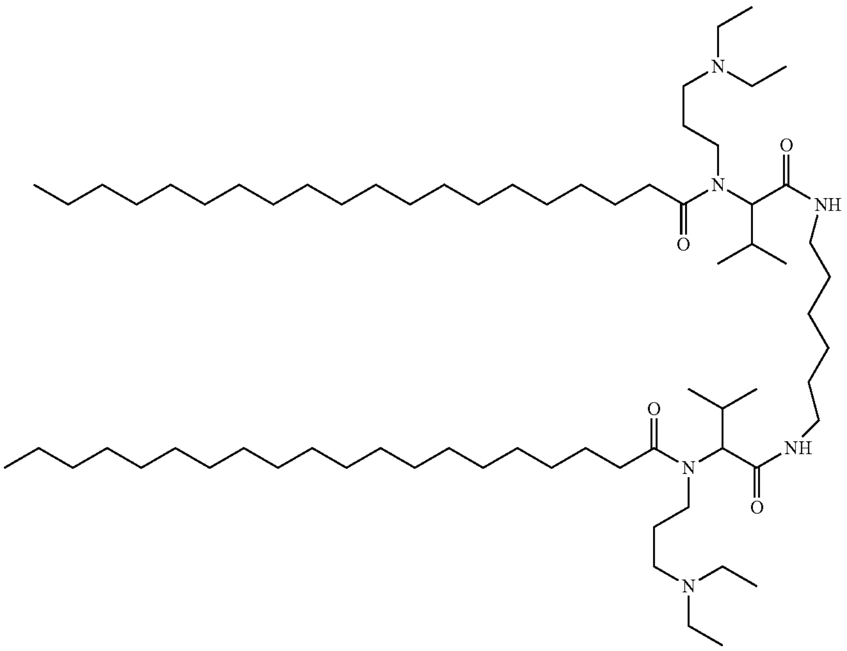
I1R3C18-1A1
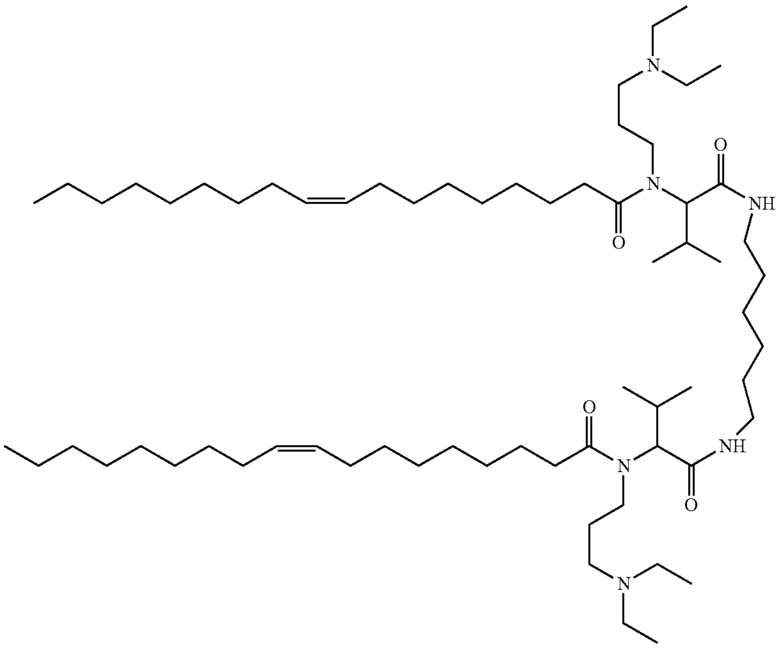

-continued
I1R3C18-2A1
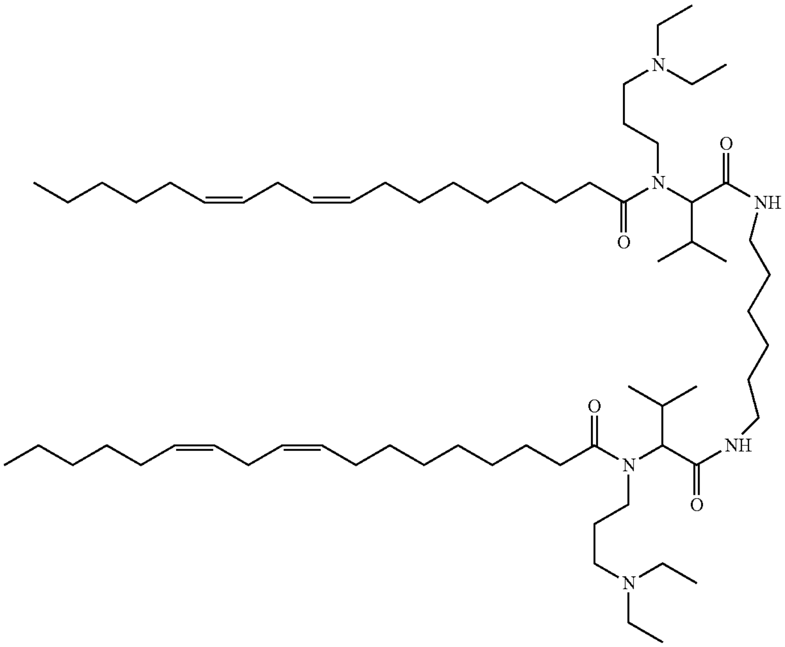
I1R5C12A1
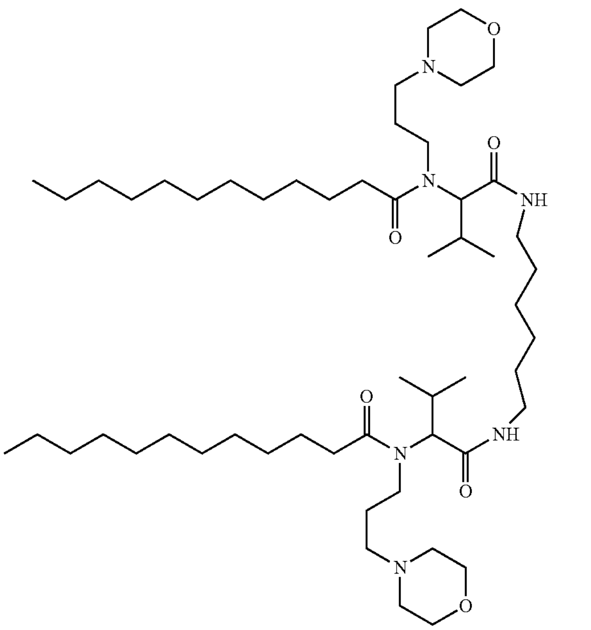
I1R5C14A1
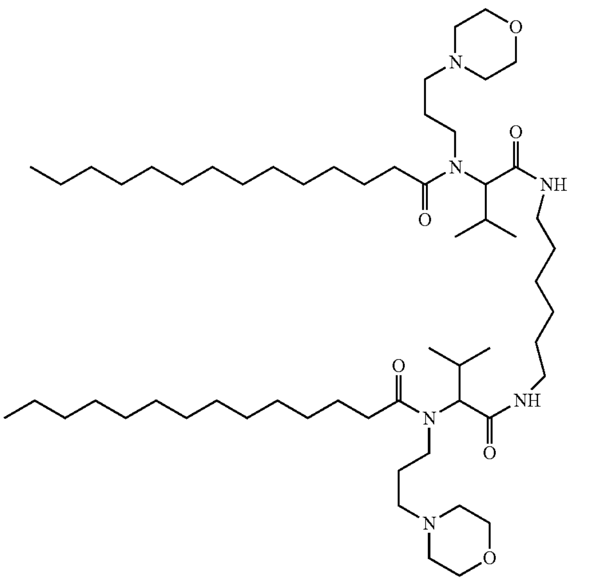

-continued
I1R5C16A1
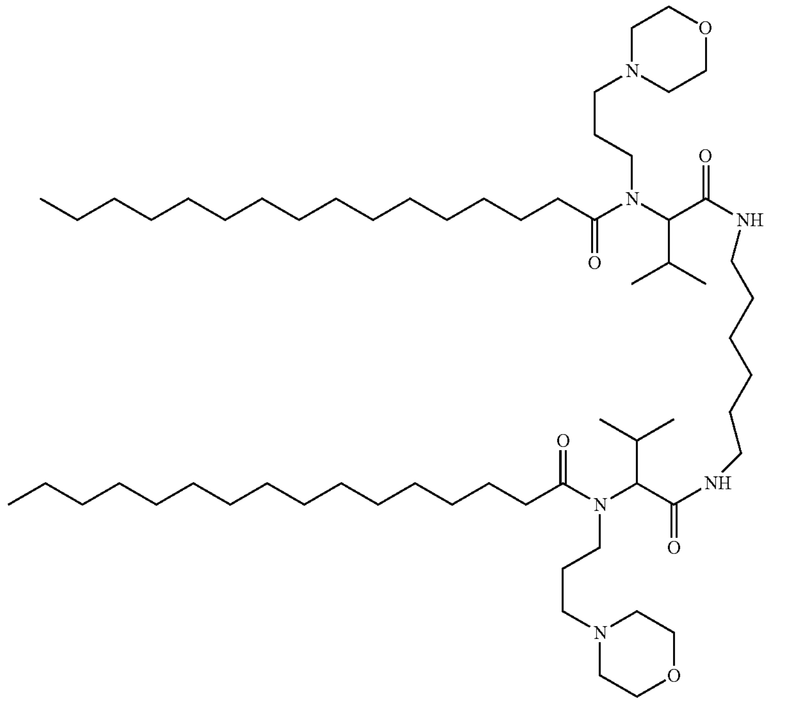
I1R5C18A1
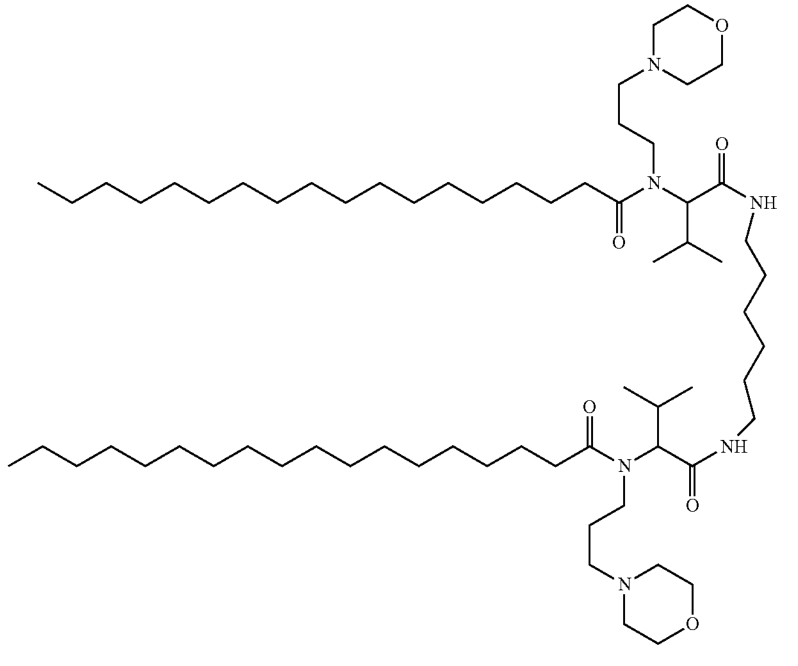

-continued
I1R5C20A1
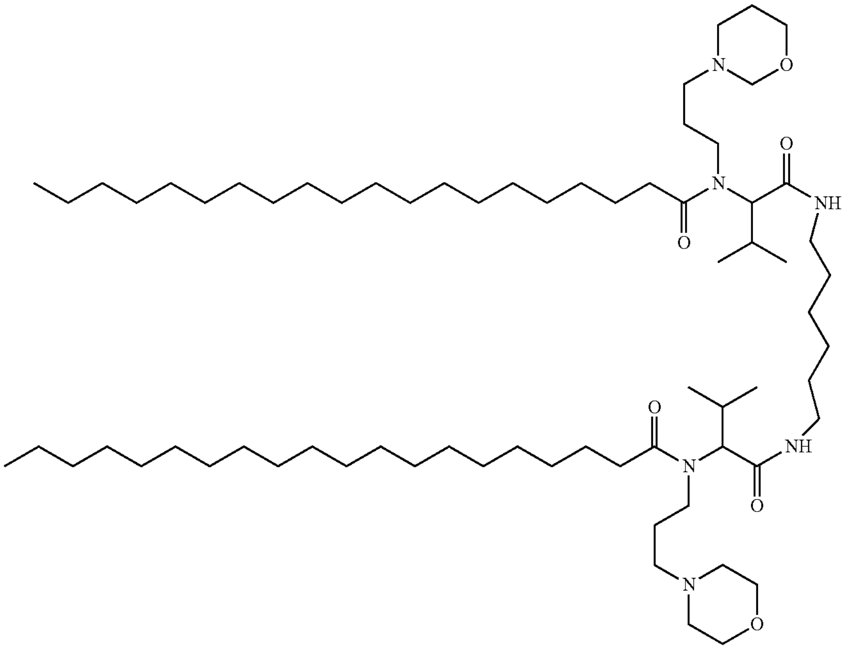
I1R5C18-1A1
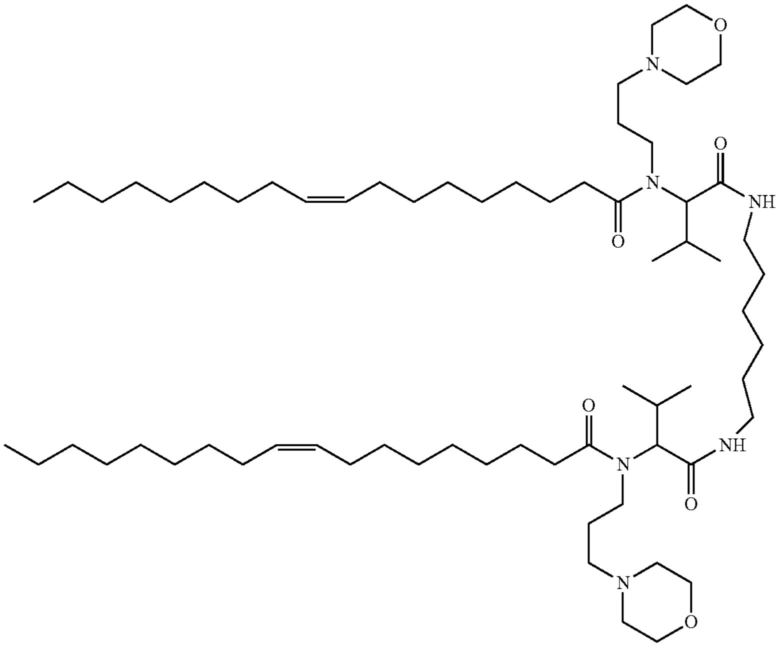

-continued
I1R5C18-2A1
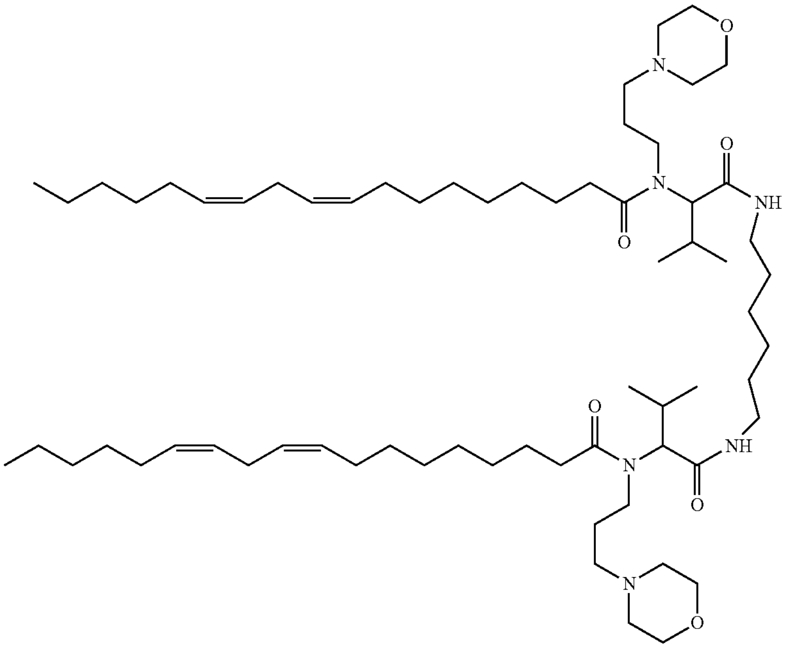
I1R11C12A1
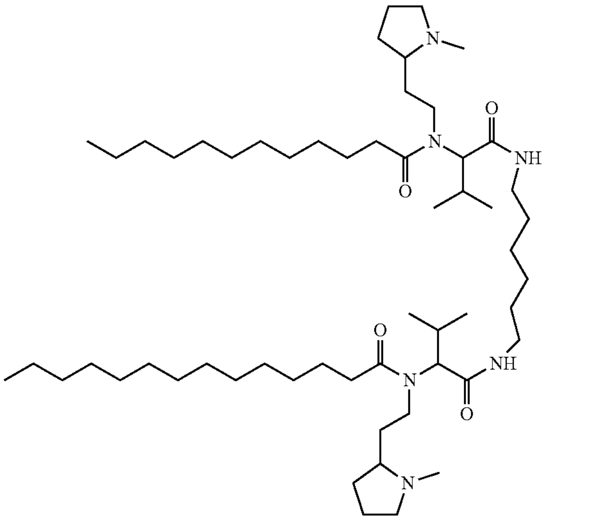
I1R11C14A1
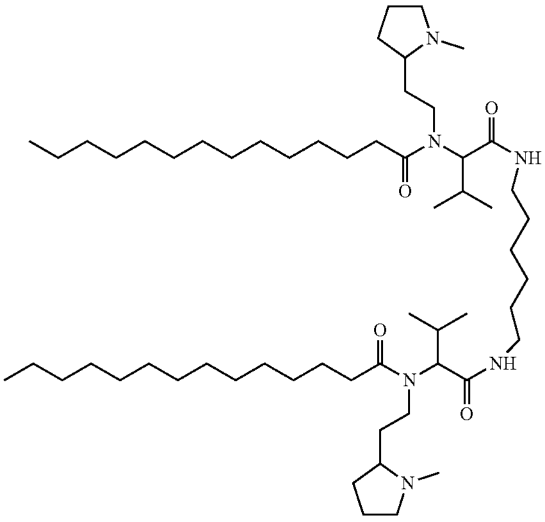

-continued
I1R11C16A1
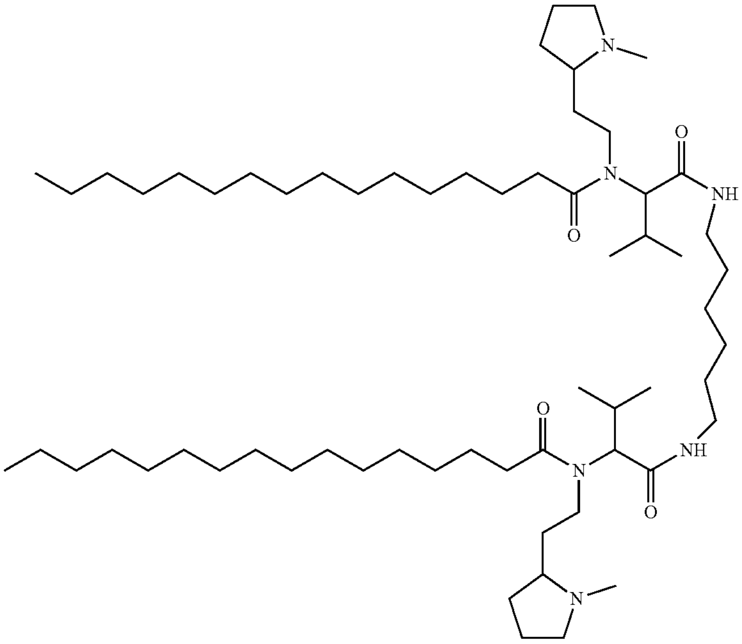
I1R11C18A1
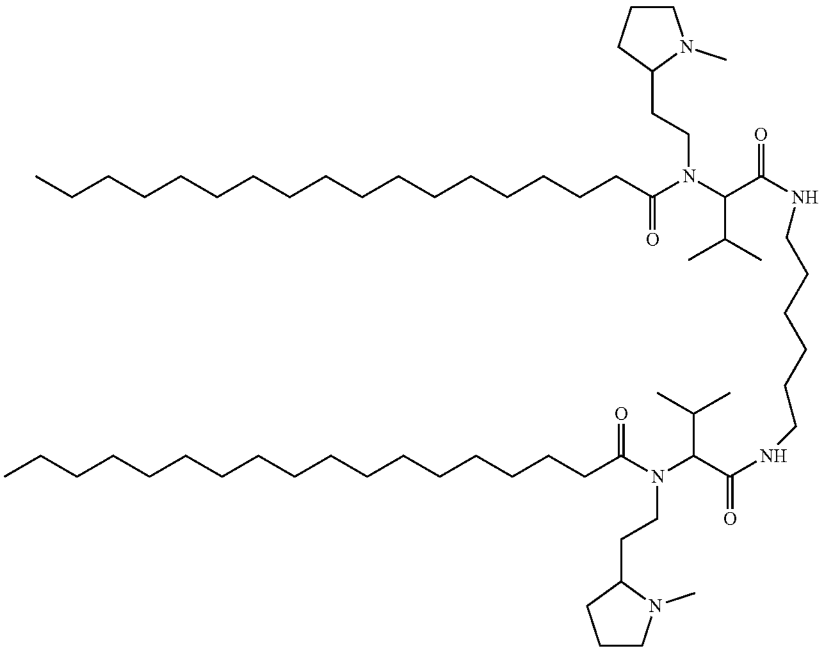

-continued
I1R11C20A1
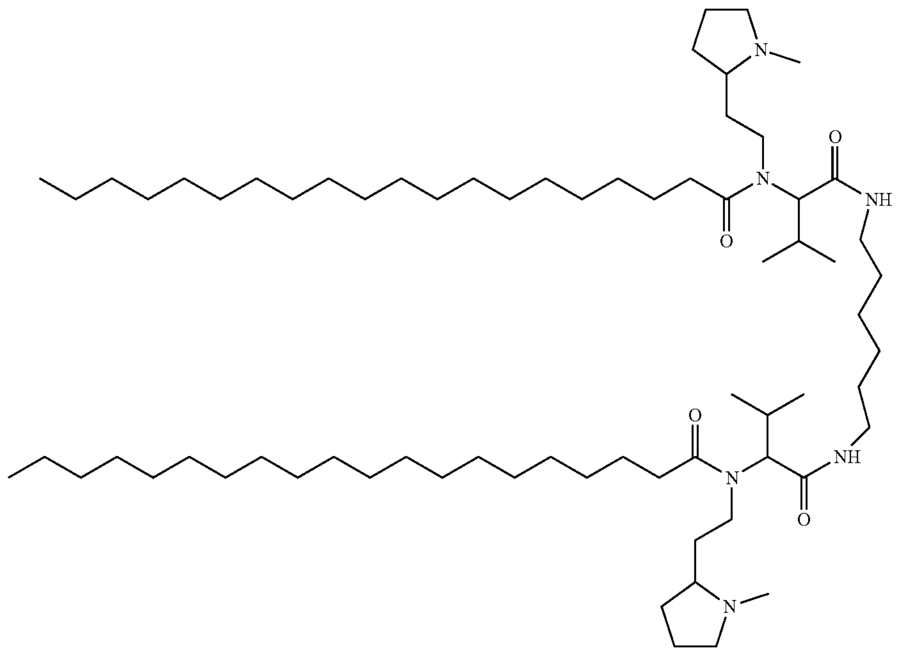
I1R11C18-1A1
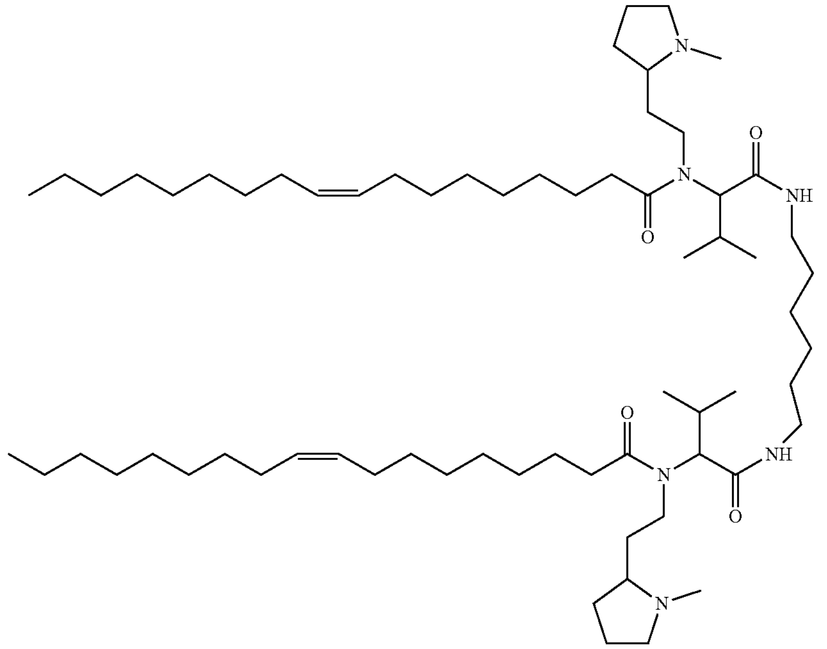

-continued
I1R11C18-2A1
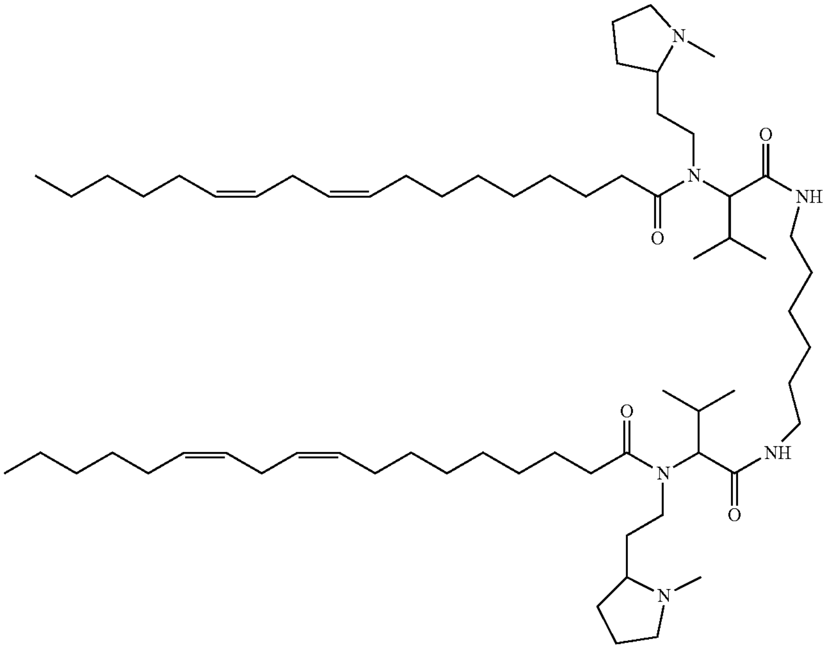
I2R1C12A1
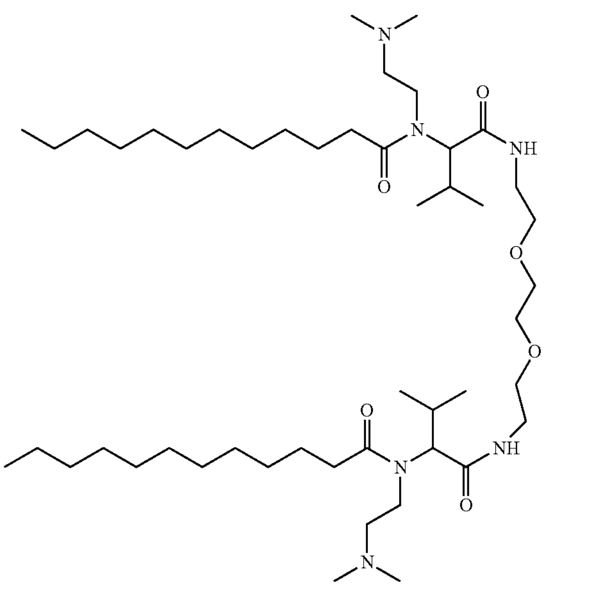
I2R1C14A1
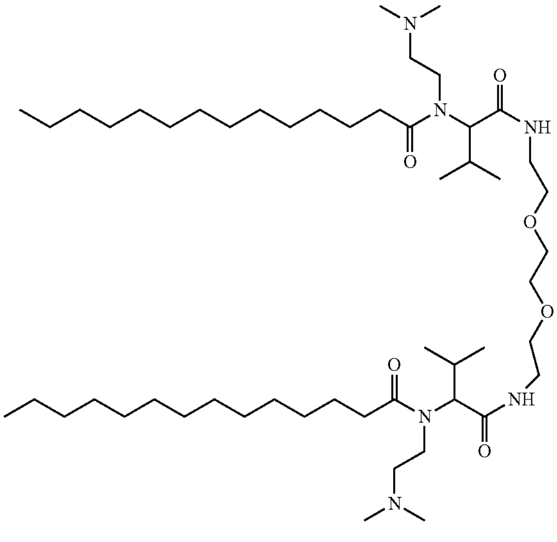

-continued
I2R1C16A1
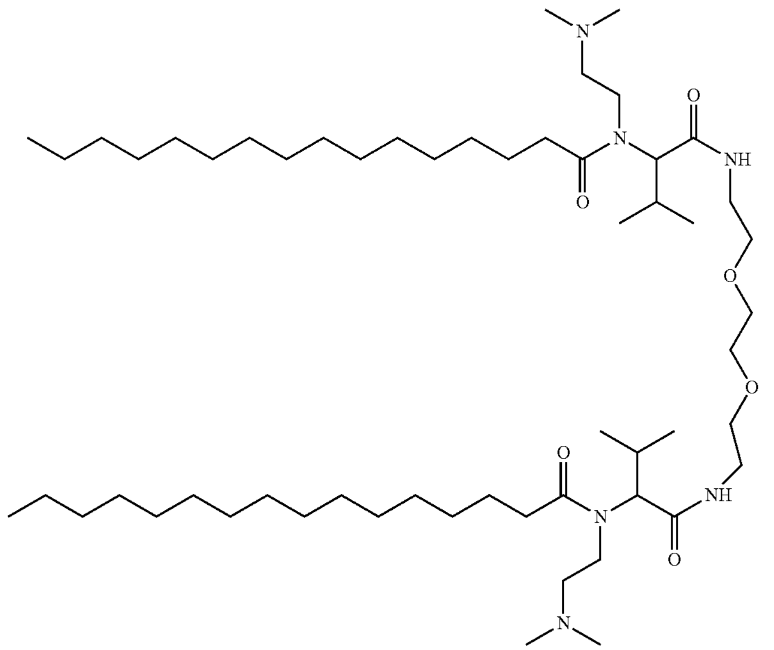
I2R1C18A1
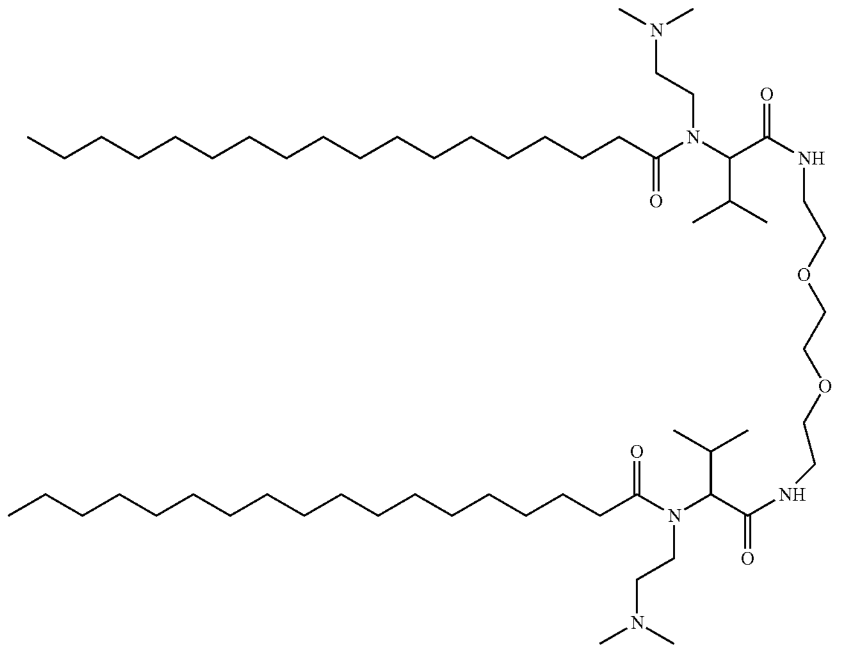

-continued
I2R1C20A1
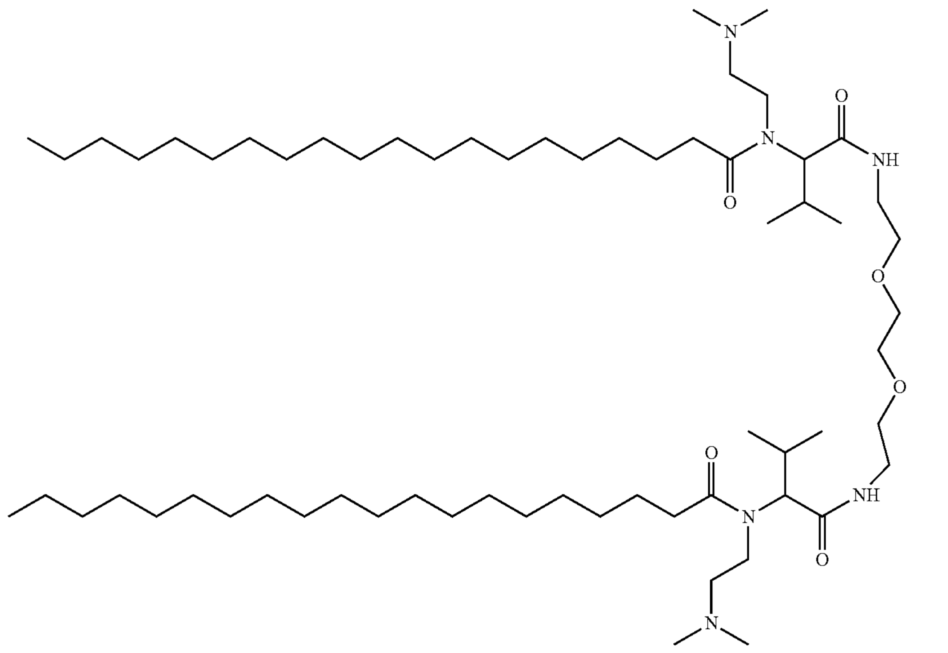
I2R1C18-1A1
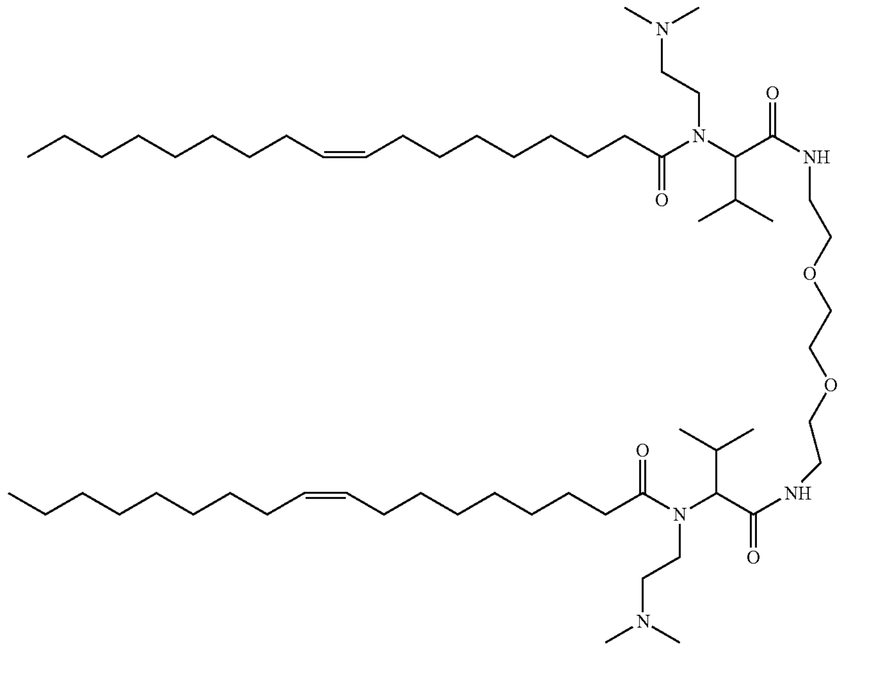

-continued
I2R1C18-2A1
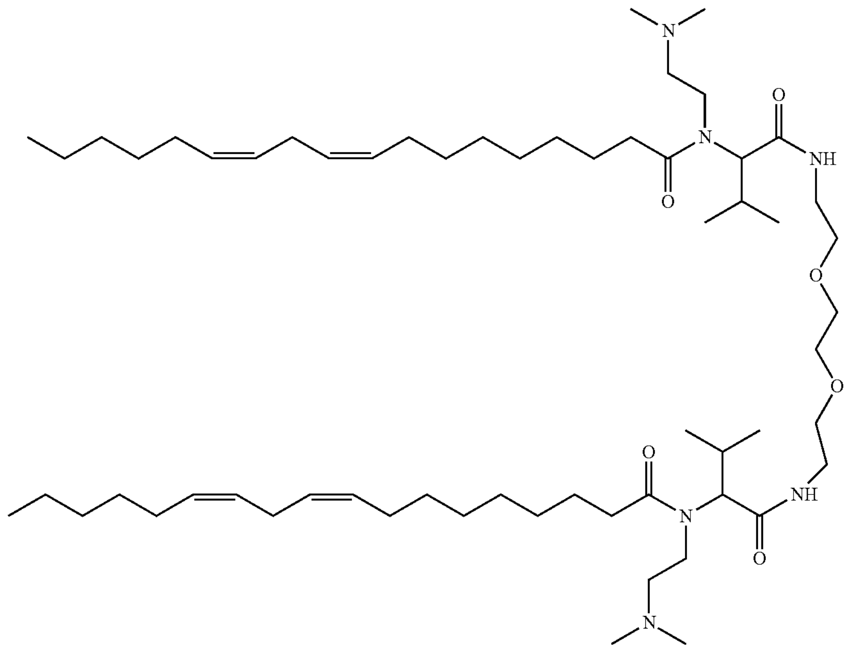
I2R2C12A1
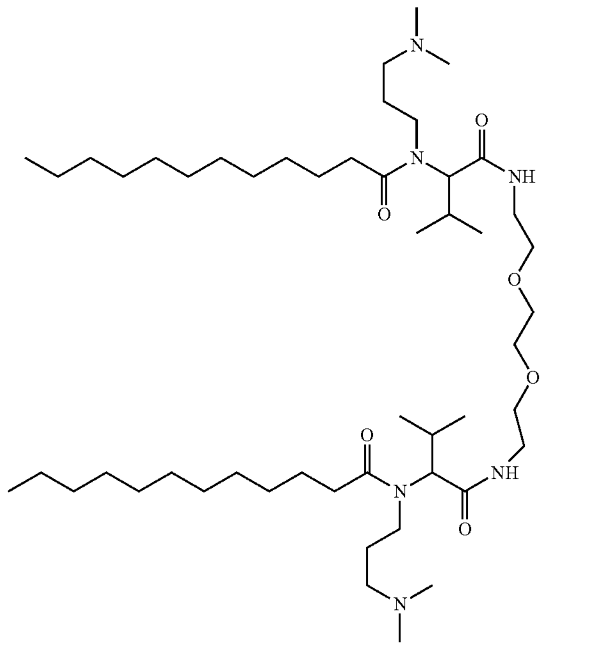
I2R2C14A1
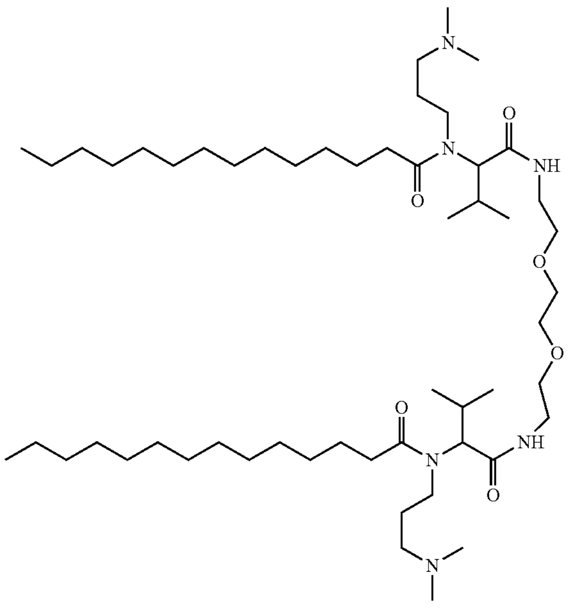

-continued
I2R2C16A1
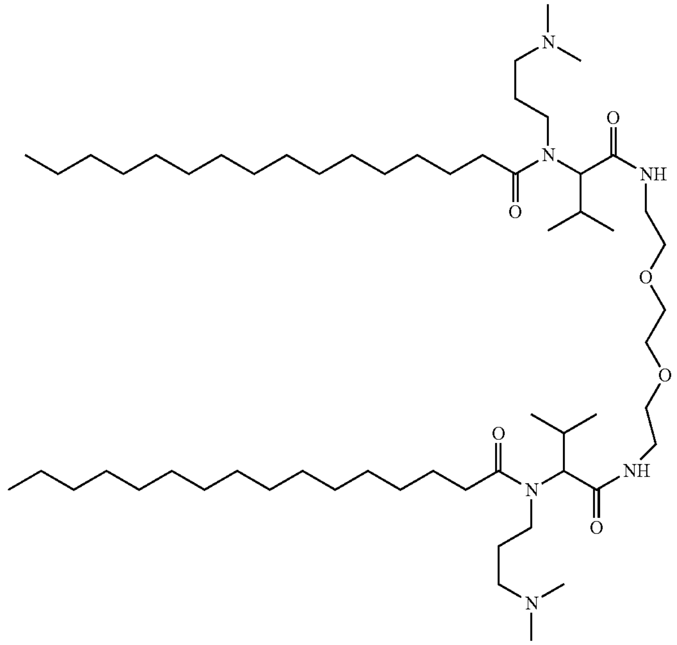
I2R2C18A1
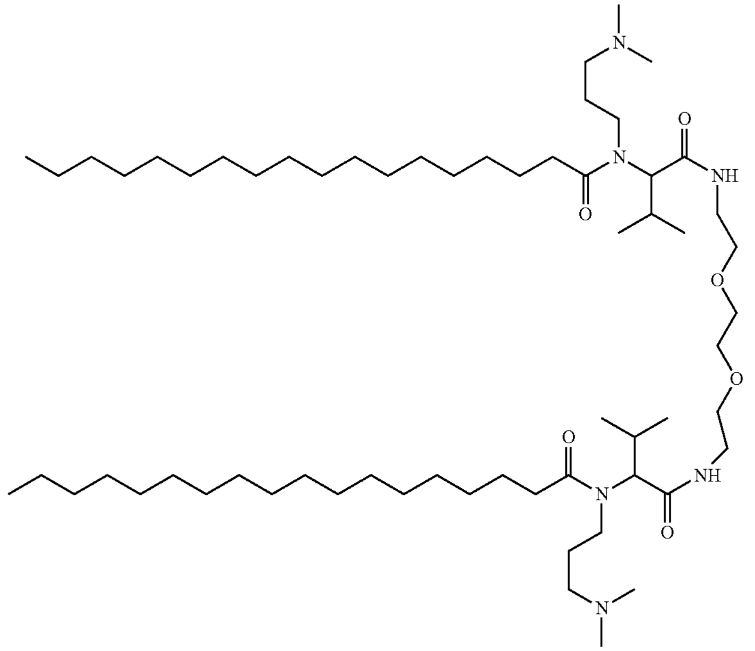

-continued
I2R2C20A1
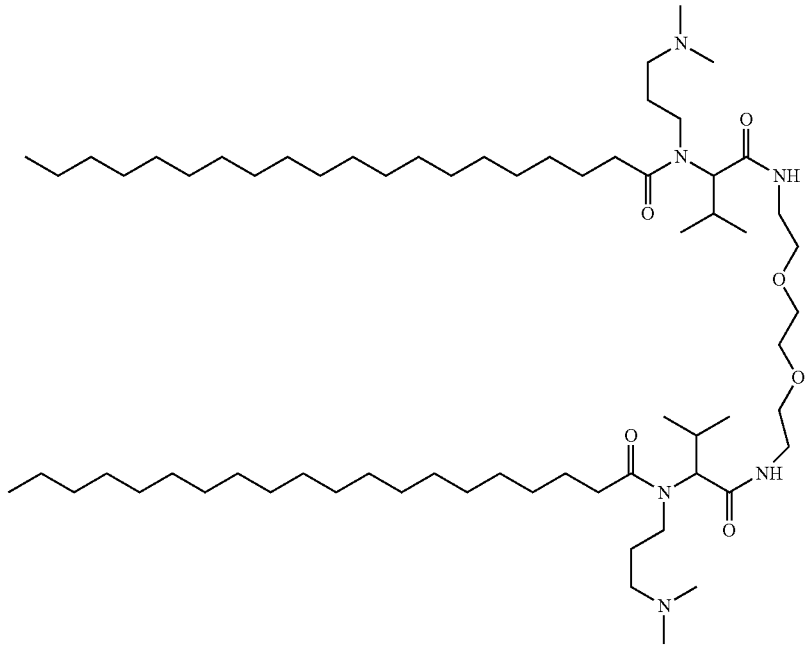
I2R2C18-1A1
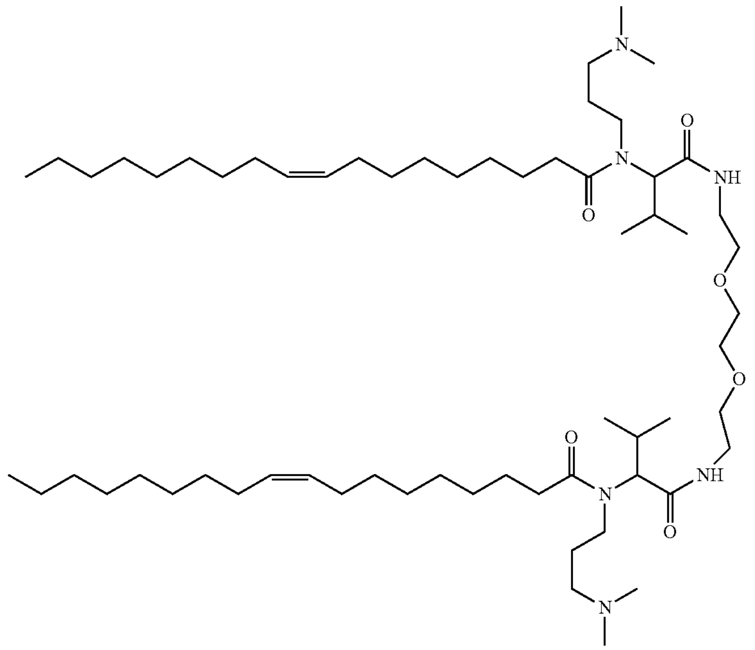

-continued
I2R2C18-2A1
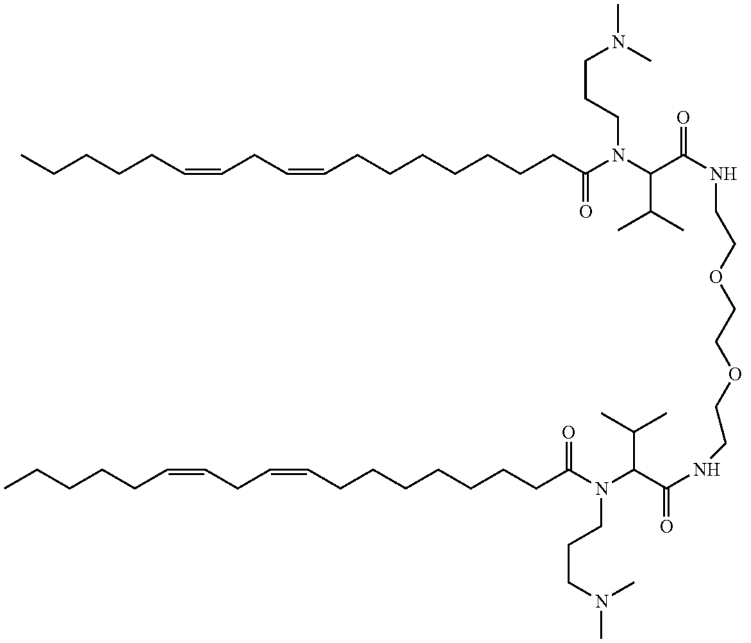
I2R3C12A1
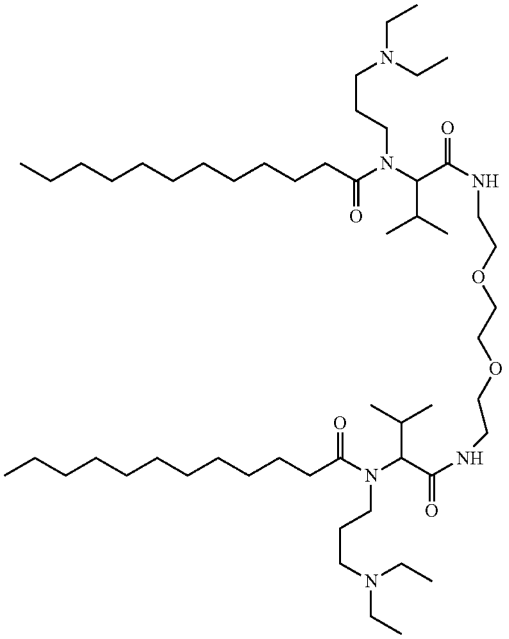
I2R3C14A1
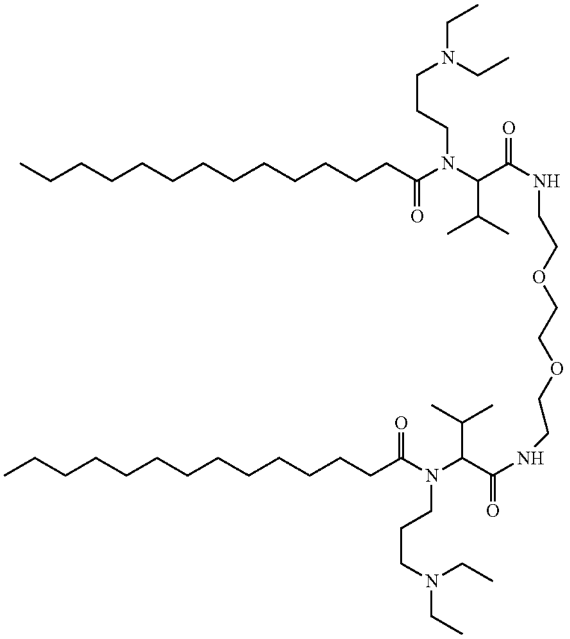

-continued
I2R3C16A1
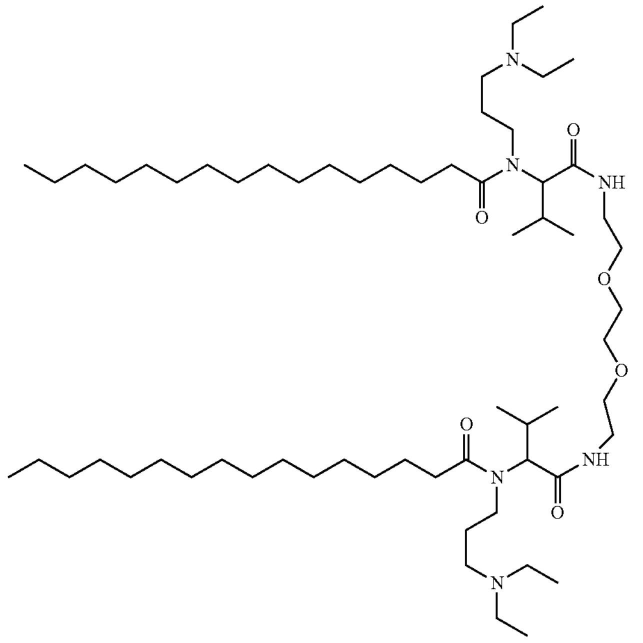
I2R3C18A1
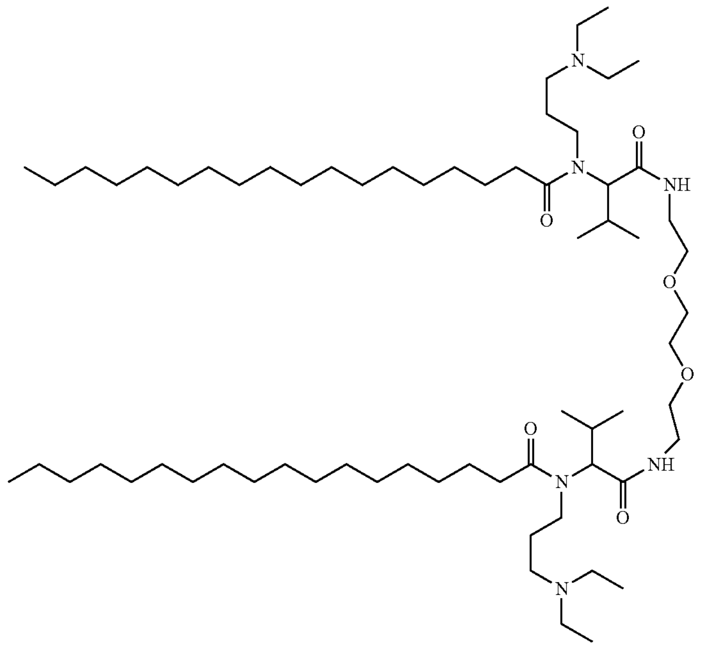

-continued
I2R3C20A1
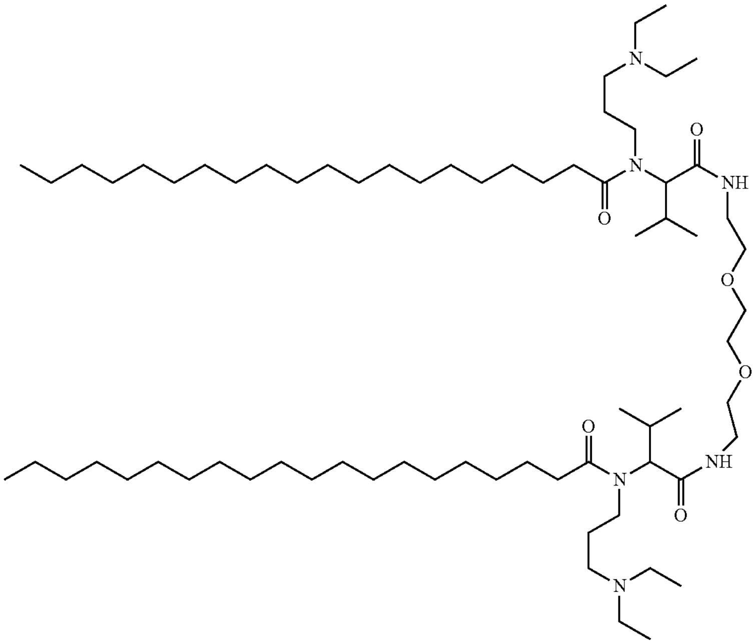
I2R3C18-1A1
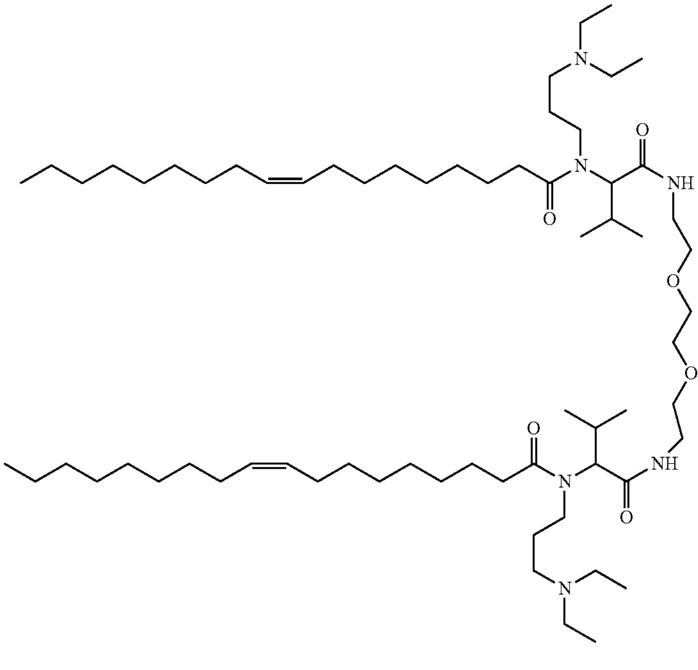

-continued
I2R3C18-2A1
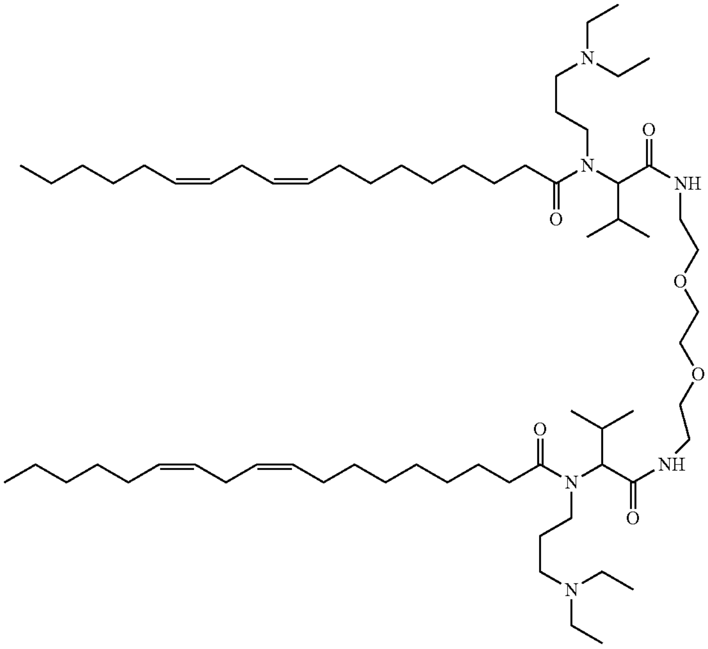
I2R5C12A1
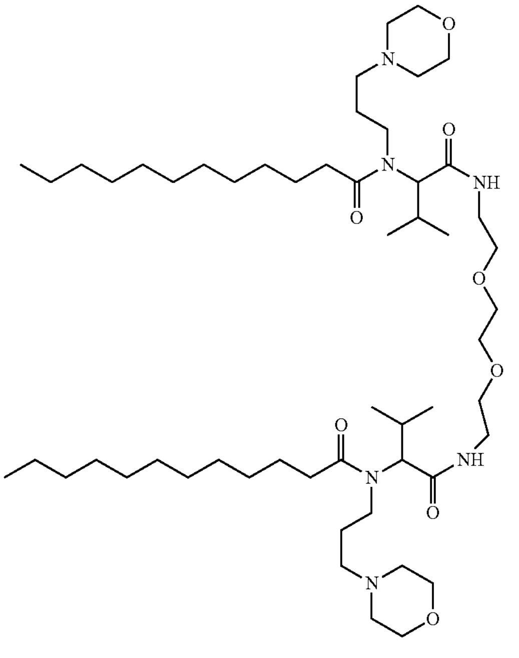
I2R5C14A1
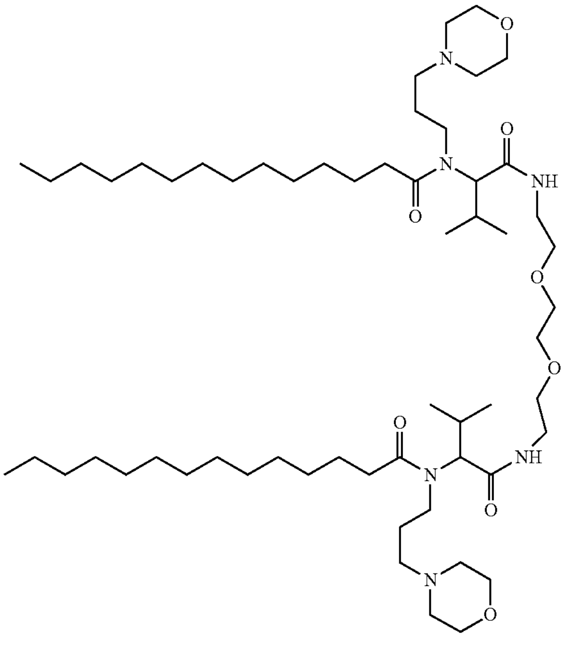

-continued
I2R5C16A1
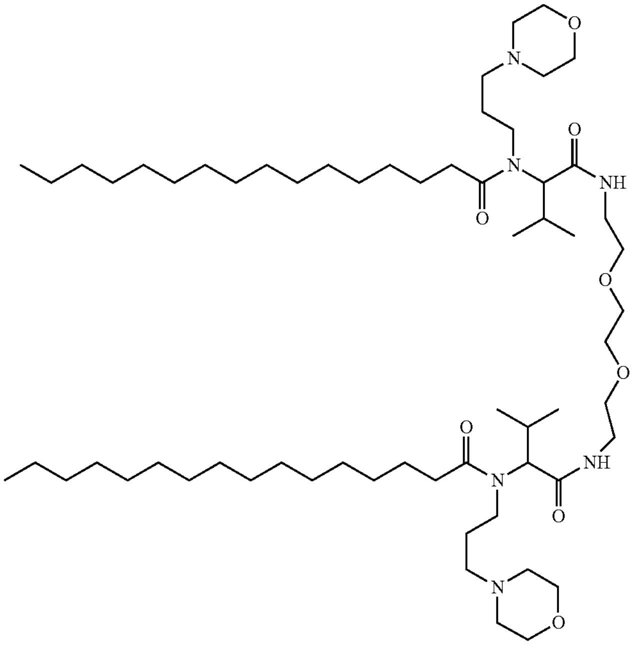
I2R5C18A1
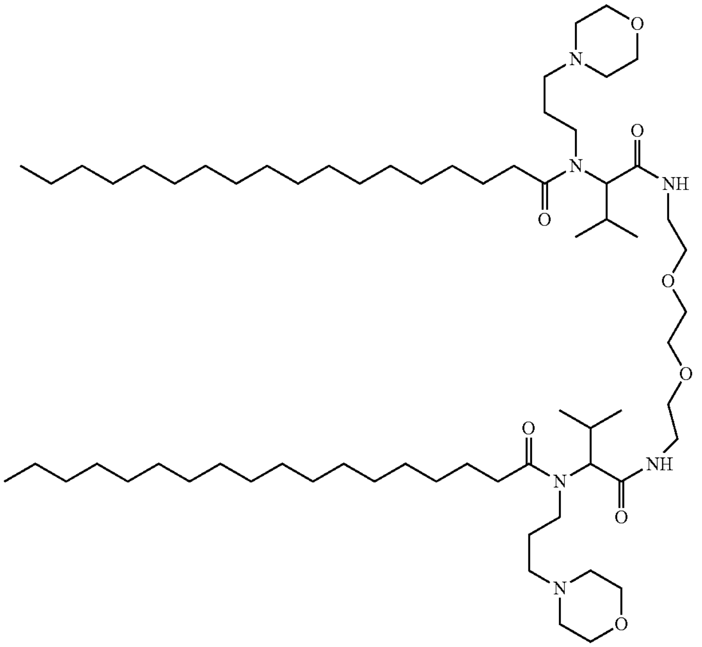

-continued
I2R5C20A1
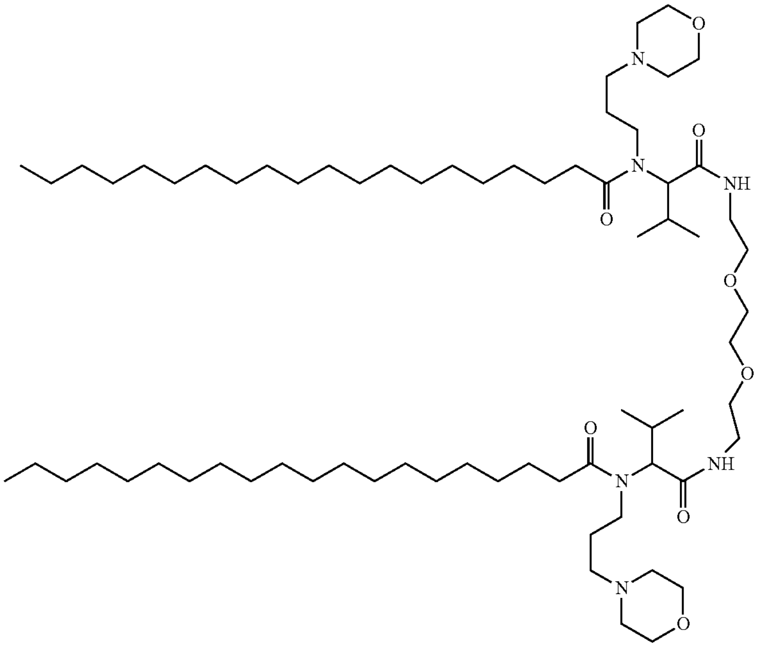
I2R5C18-1A1
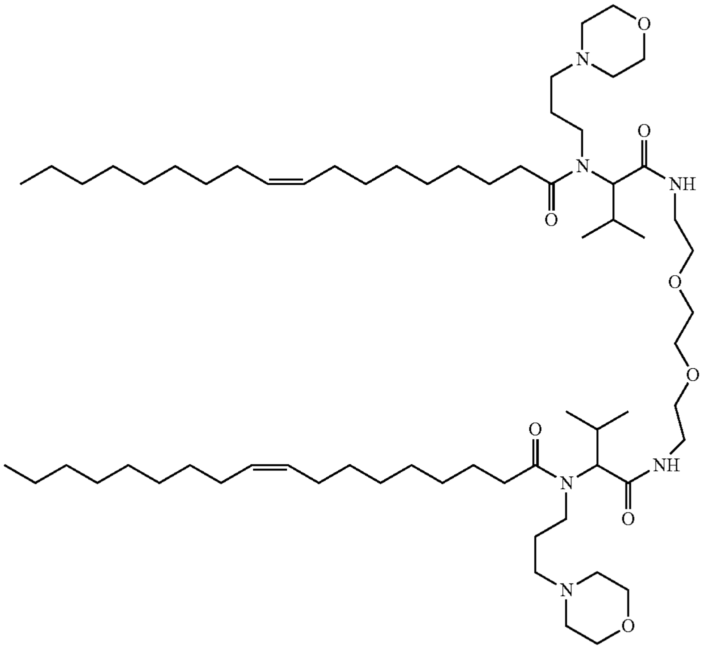

-continued
I2R5C18-2A1
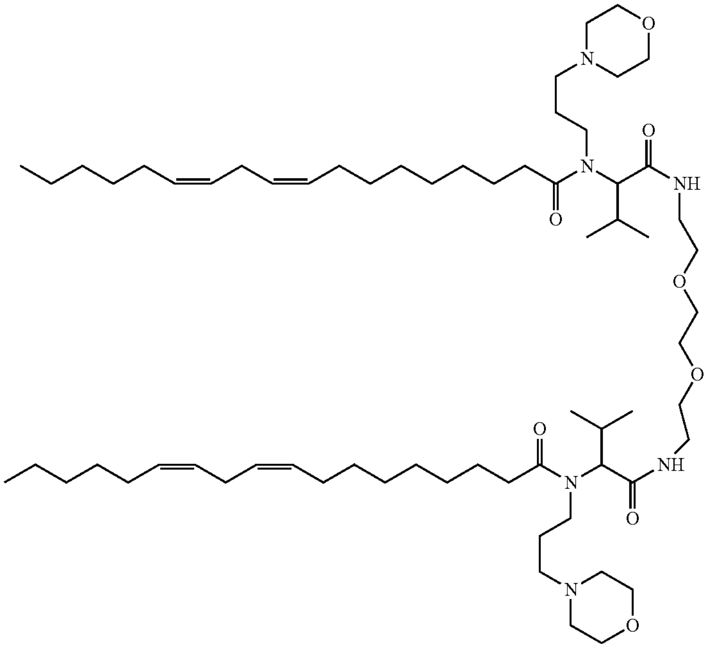
I2R11C12A1
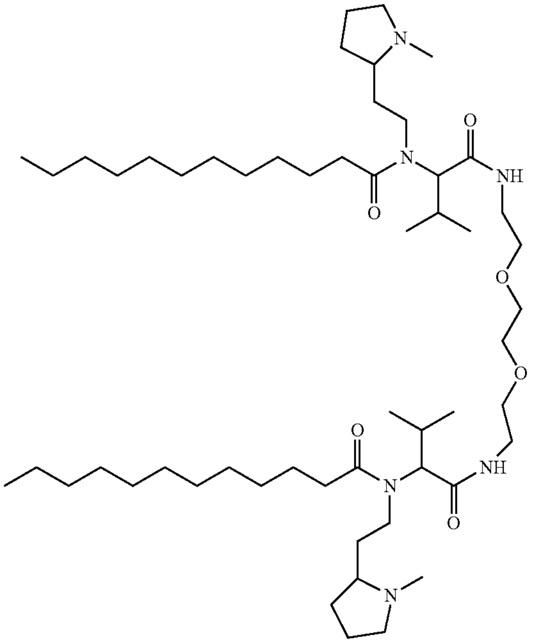
I2R11C14A1
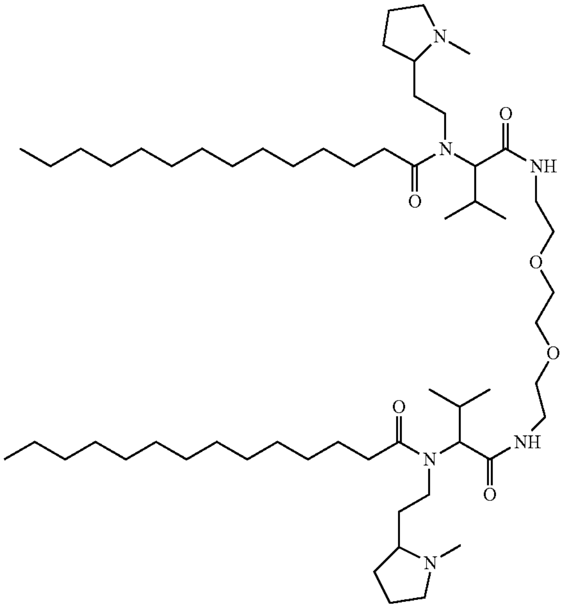

-continued
I2R11C16A1
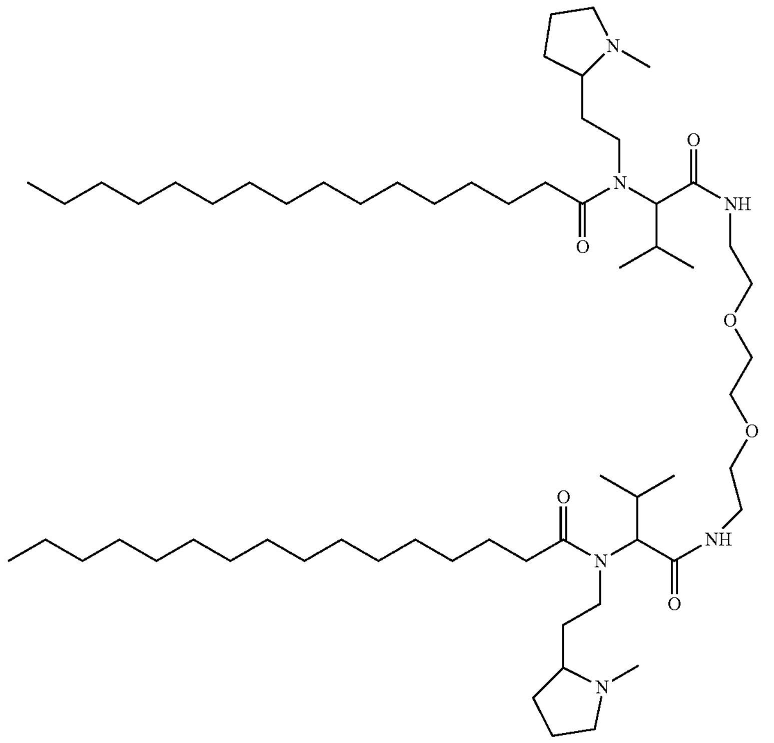
I2R11C18A1
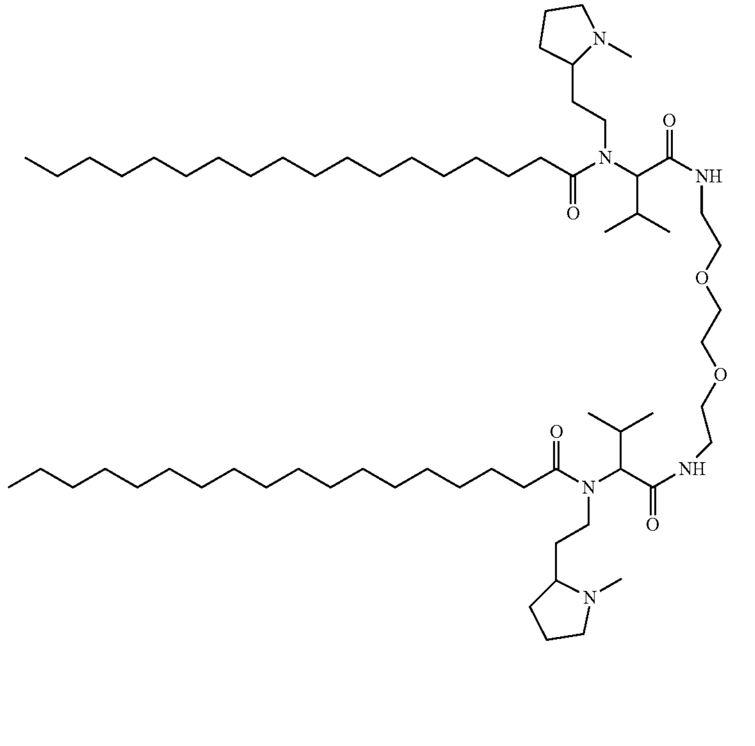

-continued
I2R11C20A1
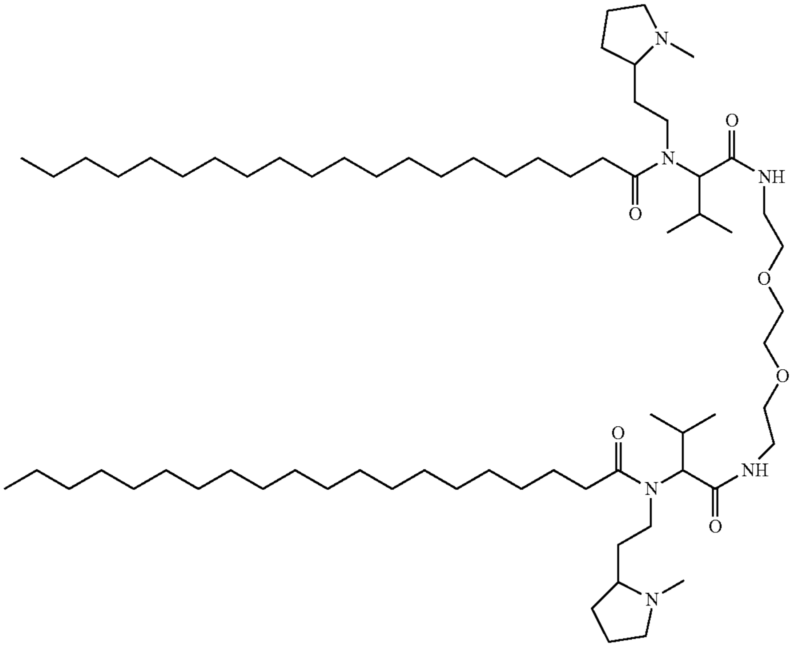
I2R11C18-1A1
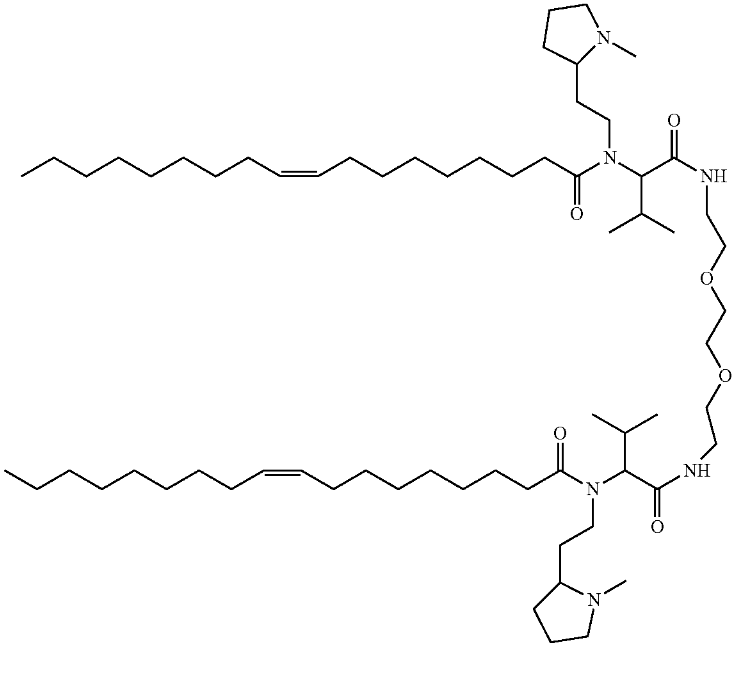

-continued
I2R11C18-2A1
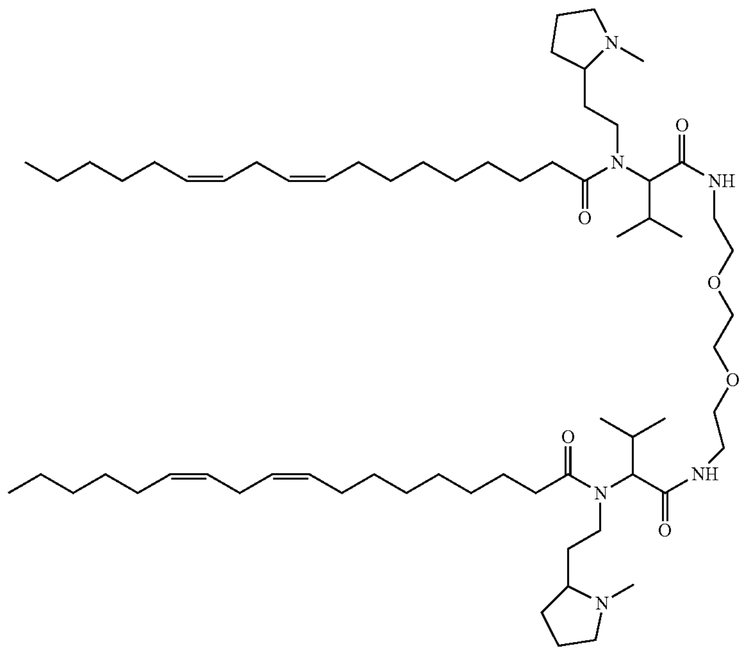
I2-1R2C18A1
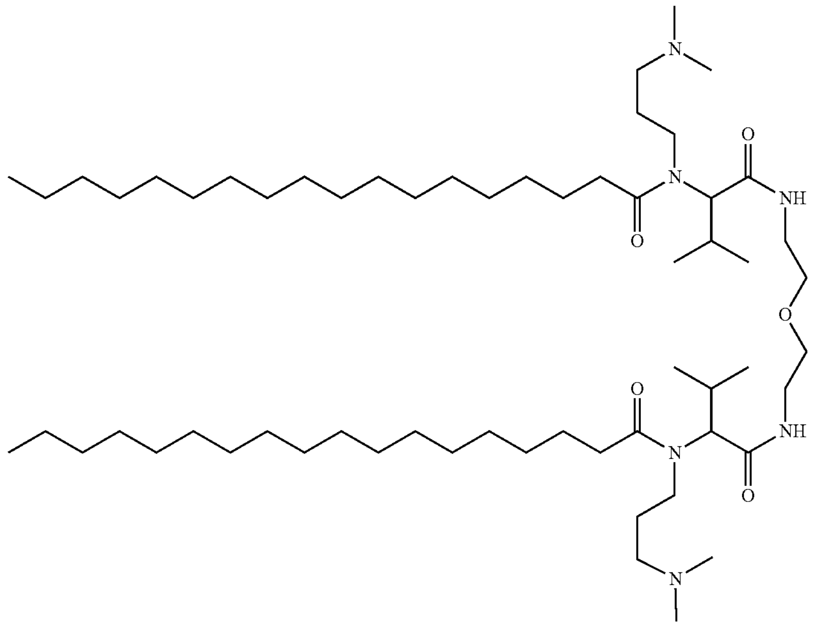

-continued

I2-3R2C18A1

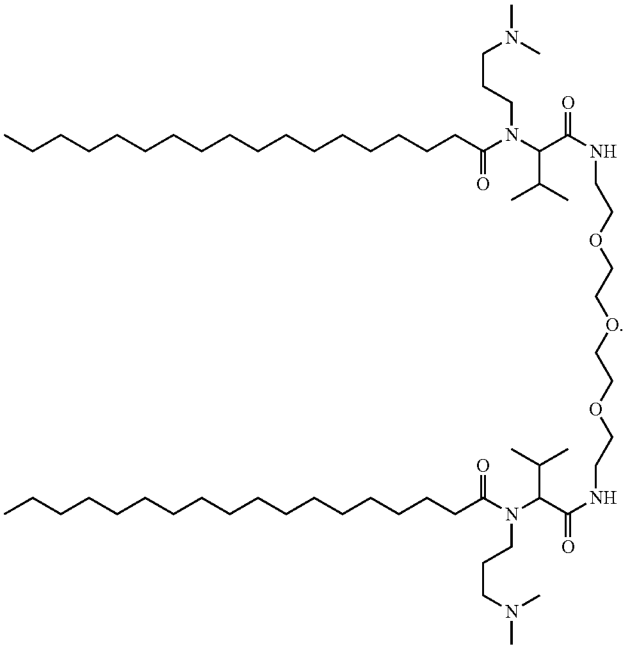

13. The method according to claim 12, wherein the ionizable cationic lipid analog material is at least one selected from the group consisting of I2R2C15A1, I2R2C16A1, I2R2C17A1, I2R2C18A1, I2R2C19A1, I2R2C20A1, I2R3C18A1, I2R3C20A1, I2R11C16A1, I2R11C18A1, I2R11C20A1, I2-1R2C18A1, or I2-3R2C18A1.

14. The method according to claim 1, wherein the protein drug comprises a negatively-charged protein drug and/or a positively-charged protein drug.

15. The method according to claim 14, wherein the protein drug is selected from the group consisting of fluorescein isothiocyanate-labeled bovine serum albumin (BSA-FITC), phycoerythrin (R-PE), superoxide dismutase, ovalbumin, green fluorescent protein, cytochrome C, or lysozyme.

16. The method according to claim 1, wherein the cell is selected from the group consisting of a renal epithelial cell, a pancreatic cancer cell, a macrophage, a dendritic cell, an umbilical vein endothelial cell, a mesenchymal stem cell (MSC), or a cervical cancer cell.

17. The method according to claim 16, wherein the cell is from a human or a mouse.

18. The method according to claim 1, wherein the cell is a Hela cell.

* * * * *